United States Patent
Lindsted et al.

(10) Patent No.: US 12,252,539 B2
(45) Date of Patent: Mar. 18, 2025

(54) ANTI-FLT3 ANTIBODIES AND COMPOSITIONS

(71) Applicant: LES LABORATOIRES SERVIER, Suresnes (FR)

(72) Inventors: Trine Lindsted, Farum (DK); Maria Carlsen Melander, Bunkeflostrand (SE); Matteo Riva, Lund (SE); Mikkel Wandahl Pedersen, Allerød (DK); Randi Westh Hansen, Roskilde (DK)

(73) Assignee: LES LABORATOIRES SERVIER, Suresnes (FR)

( * ) Notice: Subject to any disclaimer, the term of this patent is extended or adjusted under 35 U.S.C. 154(b) by 0 days.

(21) Appl. No.: 17/230,289

(22) Filed: Apr. 14, 2021

(65) Prior Publication Data

US 2021/0317216 A1    Oct. 14, 2021

Related U.S. Application Data

(60) Provisional application No. 63/009,578, filed on Apr. 14, 2020.

(51) Int. Cl.
  *C07K 16/28* (2006.01)
  *A61K 39/00* (2006.01)
  *A61K 39/395* (2006.01)
  *A61K 45/06* (2006.01)

(52) U.S. Cl.
  CPC .......... *C07K 16/2863* (2013.01); *A61K 45/06* (2013.01); *A61K 39/39533* (2013.01); *A61K 2039/505* (2013.01); *C07K 2317/565* (2013.01); *C07K 2317/74* (2013.01); *C07K 2317/92* (2013.01)

(58) Field of Classification Search
  None
  See application file for complete search history.

(56) References Cited

U.S. PATENT DOCUMENTS

| | | | |
|---|---|---|---|
| 5,635,388 A | 6/1997 | Bennett et al. | |
| 8,071,099 B2 * | 12/2011 | Li | A61P 35/02 424/139.1 |
| 10,428,143 B2 * | 10/2019 | Krummel | C07K 16/3053 |
| 2004/0131587 A1 | 7/2004 | Thomas et al. | |
| 2011/0091470 A1 | 4/2011 | Li et al. | |
| 2017/0037149 A1 * | 2/2017 | Raum | C07K 16/2863 |
| 2017/0291946 A1 | 10/2017 | Krummel et al. | |

FOREIGN PATENT DOCUMENTS

| | | |
|---|---|---|
| EP | 1186301 B1 | 8/2006 |
| WO | 2018/119279 A1 | 6/2018 |
| WO | 2018/220584 A1 | 12/2018 |
| WO | 2020/053300 A1 | 3/2020 |
| WO | WO 2021/209495 | * 10/2021 |

OTHER PUBLICATIONS

Verstraete et al., "Structural Insights into the Extracellular Assembly of the Hematopoietic Flt3 Signaling Complex," Blood (2011) 1:60-68.

Zeigler et al., "Cellular and molecular characterization of the role of the FLK-2/FLT-3 receptor tyrosine kinase in hematopoietic stem cells," Blood (1994) 84(8):2422-30.

* cited by examiner

*Primary Examiner* — Marianne P Allen
(74) *Attorney, Agent, or Firm* — Steptoe LLP; Z. Ying Li; Wyan-Ching M. Lee

(57) ABSTRACT

This invention relates to anti-FLT3 antibodies and methods of using them in enhancing immunity in a patient in need thereof and in treating cancer.

14 Claims, 20 Drawing Sheets

Specification includes a Sequence Listing.

ANTI-FLT3 ANTIBODIES AND COMPOSITIONS

CROSS-REFERENCE TO RELATED APPLICATION

This application claims priority from U.S. Provisional Patent Application 63/009,578, filed Apr. 14, 2020. The disclosure of that priority application is incorporated by reference herein in its entirety.

SEQUENCE LISTING

The instant application contains a Sequence Listing which has been submitted electronically in ASCII format and is hereby incorporated by reference in its entirety. The electronic copy of the Sequence Listing, created on Apr. 9, 2021, is named 022675_US047_SL.txt and is 51,577 bytes in size.

BACKGROUND OF THE INVENTION

FMS-like tyrosine kinase 3 (FLT3), or CD135, is a class III receptor tyrosine kinase expressed on the surface of early hematopoietic progenitor cells that plays an important role in the development of the immune system. Upon binding to the cytokine FLT3 ligand (FLT3L), FLT3 dimerizes and activates multiple signaling pathways that control cellular differentiation, proliferation, and survival.

FLT3 has also been found to be expressed by dendritic cells (DC), a class of professional antigen-presenting cells. Upon contact with an antigen, dendritic cells internalize and process the antigen, and present it in association with an MHC class II complex to T cells, leading to T cell activation. FLT3 signaling plays a major role in dendritic cell differentiation and expansion. Mice with a deficiency in FLT3 or FLT3 ligand (FLT3L) exhibit reduced DC numbers, while mice treated with FLT3L exhibit increased DC numbers. These observations indicate an essential role for FLT3 in steady-state DC development.

SUMMARY OF THE INVENTION

The present disclosure provides anti-FTL3 antibodies that can stimulate the activity of dendritic cells. The antibodies can be used to enhance the immune response of a patient in need thereof, for example, a patient having cancer or an immune deficiency. Also provided are pharmaceutical compositions comprising one or more of these antibodies, and use of the antibodies and pharmaceutical compositions for treatment of cancer. The antibodies and compositions described herein may be used in a method for treating cancer in a patient; may be used for the manufacture of a medicament for treating cancer in a patient; or may be for use in treating cancer in a patient. Compared to currently available treatments for such cancers, including antibody treatments, it is contemplated that the antibodies and compositions described herein may provide a superior clinical response either alone or in combination with another cancer therapeutic.

In some embodiments, the present disclosure provides an anti-FLT3 antibody or an antigen-binding portion thereof that competes or cross-competes for binding with or binds to the same epitope of human FLT3 as antibody 17566, 17526, 17667, 17667-0, 17679, 17494, 17543, or 17497. In certain embodiments, the anti-FLT3 antibody or antigen-binding portion is defined by the amino acid sequences of the six CDRs, heavy and light chain variable domains, or heavy and light chains of said antibody.

In some embodiments, the present disclosure provides an anti-FLT3 antibody or an antigen-binding portion thereof, wherein:
  a) the heavy chain of said antibody comprises:
    i) heavy chain complementarity determining regions (H-CDR)-1-3 comprising the amino acid sequences of SEQ ID NOs: 5-7, respectively;
    ii) a heavy chain variable domain (VH) comprising an amino acid sequence at least 90% identical to the amino acid sequence of SEQ ID NO: 3;
    iii) a VH comprising the amino acid sequence of SEQ ID NO: 3; or
    iv) a heavy chain (HC) comprising the amino acid sequences of SEQ ID NOs: 3 and 75; and
  b) the light chain of said antibody comprises:
    i) light chain complementarity determining regions (L-CDR)-1-3 comprising the amino acid sequences of SEQ ID NOs: 8-10, respectively;
    ii) a light chain variable domain (VL) comprising an amino acid sequence at least 90% identical to the amino acid sequence of SEQ ID NO: 4;
    iii) a VL comprising the amino acid sequence of SEQ ID NO: 4; or
    iv) a light chain (LC) comprising the amino acid sequences of SEQ ID NOs: 4 and 76.

In some embodiments, the present disclosure provides an anti-FLT3 antibody or an antigen-binding portion thereof, wherein:
  a) the heavy chain of said antibody comprises:
    i) H-CDR-1-3 comprising the amino acid sequences of SEQ ID NOs: 15-17, respectively;
    ii) a VH comprising an amino acid sequence at least 90% identical to the amino acid sequence of SEQ ID NO: 13;
    iii) a VH comprising the amino acid sequence of SEQ ID NO: 13; or
    iv) an HC comprising the amino acid sequences of SEQ ID NOs: 13 and 75; and
  b) the light chain of said antibody comprises:
    i) L-CDR-1-3 comprising the amino acid sequences of SEQ ID NOs: 18-20, respectively;
    ii) a VL comprising an amino acid sequence at least 90% identical to the amino acid sequence of SEQ ID NO: 14;
    iii) a VL comprising the amino acid sequence of SEQ ID NO: 14; or
    iv) an LC comprising the amino acid sequences of SEQ ID NOs: 14 and 76.

In some embodiments, the present disclosure provides an anti-FLT3 antibody or an antigen-binding portion thereof, wherein:
  a) the heavy chain of said antibody comprises:
    i) H-CDR-1-3 comprising the amino acid sequences of SEQ ID NOs: 25-27, respectively;
    ii) a VH comprising an amino acid sequence at least 90% identical to the amino acid sequence of SEQ ID NO: 23;
    iii) a VH comprising the amino acid sequence of SEQ ID NO: 23; or
    iv) an HC comprising the amino acid sequences of SEQ ID NOs: 23 and 75; and
  b) the light chain of said antibody comprises:
    i) L-CDR-1-3 comprising the amino acid sequences of SEQ ID NOs: 28-30, respectively;

ii) a VL comprising an amino acid sequence at least 90% identical to the amino acid sequence of SEQ ID NO: 24;
iii) a VL comprising the amino acid sequence of SEQ ID NO: 24; or
iv) an LC comprising the amino acid sequences of SEQ ID NOs: 24 and 76.

In some embodiments, the present disclosure provides an anti-FLT3 antibody or an antigen-binding portion thereof, wherein:
a) the heavy chain of said antibody comprises:
i) H-CDR-1-3 comprising the amino acid sequences of SEQ ID NOs: 35-37, respectively;
ii) a VH comprising an amino acid sequence at least 90% identical to the amino acid sequence of SEQ ID NO: 33;
iii) a VH comprising the amino acid sequence of SEQ ID NO: 33; or
iv) an HC comprising the amino acid sequences of SEQ ID NOs: 33 and 75; and
b) the light chain of said antibody comprises:
i) L-CDR-1-3 comprising the amino acid sequences of SEQ ID NOs: 38-40, respectively;
ii) a VL comprising an amino acid sequence at least 90% identical to the amino acid sequence of SEQ ID NO: 34;
iii) a VL comprising the amino acid sequence of SEQ ID NO: 34; or
iv) an LC comprising the amino acid sequences of SEQ ID NOs: 34 and 76.

In some embodiments, the present disclosure provides an anti-FLT3 antibody or an antigen-binding portion thereof, wherein:
a) the heavy chain of said antibody comprises:
i) H-CDR-1-3 comprising the amino acid sequences of SEQ ID NOs: 45-47, respectively;
ii) a VH comprising an amino acid sequence at least 90% identical to the amino acid sequence of SEQ ID NO: 43;
iii) a VH comprising the amino acid sequence of SEQ ID NO: 43; or
iv) an HC comprising the amino acid sequences of SEQ ID NOs: 43 and 75; and
b) the light chain of said antibody comprises:
i) L-CDR-1-3 comprising the amino acid sequences of SEQ ID NOs: 48-50, respectively;
ii) a VL comprising an amino acid sequence at least 90% identical to the amino acid sequence of SEQ ID NO: 44;
iii) a VL comprising the amino acid sequence of SEQ ID NO: 44; or
iv) an LC comprising the amino acid sequences of SEQ ID NOs: 44 and 76.

In some embodiments, the present disclosure provides an anti-FLT3 antibody or an antigen-binding portion thereof, wherein:
a) the heavy chain of said antibody comprises:
i) H-CDR-1-3 comprising the amino acid sequences of SEQ ID NOs: 55-57, respectively;
ii) a VH comprising an amino acid sequence at least 90% identical to the amino acid sequence of SEQ ID NO: 53;
iii) a VH comprising the amino acid sequence of SEQ ID NO: 53; or
iv) an HC comprising the amino acid sequences of SEQ ID NOs: 53 and 75; and
b) the light chain of said antibody comprises:
i) L-CDR-1-3 comprising the amino acid sequences of SEQ ID NOs: 58-60, respectively;
ii) a VL comprising an amino acid sequence at least 90% identical to the amino acid sequence of SEQ ID NO: 54;
iii) a VL comprising the amino acid sequence of SEQ ID NO: 54; or
iv) an LC comprising the amino acid sequences of SEQ ID NOs: 54 and 76.

In some embodiments, the present disclosure provides an anti-FLT3 antibody or an antigen-binding portion thereof, wherein:
a) the heavy chain of said antibody comprises:
i) H-CDR-1-3 comprising the amino acid sequences of SEQ ID NOs: 65-67, respectively;
ii) a VH comprising an amino acid sequence at least 90% identical to the amino acid sequence of SEQ ID NO: 63;
iii) a VH comprising the amino acid sequence of SEQ ID NO: 63; or
iv) an HC comprising the amino acid sequences of SEQ ID NOs: 63 and 75; and
b) the light chain of said antibody comprises:
i) L-CDR-1-3 comprising the amino acid sequences of SEQ ID NOs: 68-70, respectively;
ii) a VL comprising an amino acid sequence at least 90% identical to the amino acid sequence of SEQ ID NO: 64;
iii) a VL comprising the amino acid sequence of SEQ ID NO: 64; or
iv) an LC comprising the amino acid sequences of SEQ ID NOs: 64 and 76.

In some embodiments, the present disclosure provides an anti-FLT3 antibody or an antigen-binding portion thereof, wherein:
a) the heavy chain of said antibody comprises:
i) H-CDR-1-3 comprising the amino acid sequences of SEQ ID NOs: 25-27, respectively;
ii) a VH comprising an amino acid sequence at least 90% identical to the amino acid sequence of SEQ ID NO: 73;
iii) a VH comprising the amino acid sequence of SEQ ID NO: 73; or
iv) an HC comprising the amino acid sequences of SEQ ID NOs: 73 and 75; and
b) the light chain of said antibody comprises:
i) L-CDR-1-3 comprising the amino acid sequences of SEQ ID NOs: 28-30, respectively;
ii) a VL comprising an amino acid sequence at least 90% identical to the amino acid sequence of SEQ ID NO: 74;
iii) a VL comprising the amino acid sequence of SEQ ID NO: 74; or
iv) an LC comprising the amino acid sequences of SEQ ID NOs: 74 and 76.

The present disclosure also provides isolated nucleic acid molecules, vectors, and host cells comprising nucleotide sequences that encode the heavy chain or an antigen-binding portion thereof, the light chain or an antigen-binding portion thereof, or both, of an anti-FLT3 antibody or antigen-binding portion described herein. Further, the present disclosure provides methods for producing an anti-FLT3 antibody or antigen-binding portion described herein by culturing said host cells, as well as methods for producing an antibody composition by admixing antibodies or antigen-binding portions described herein.

Other features, objectives, and advantages of the invention are apparent in the detailed description that follows. It should be understood, however, that the detailed description, while indicating embodiments and aspects of the invention, is given by way of illustration only, not limitation. Various changes and modifications within the scope of the invention will become apparent to those skilled in the art from the detailed description.

BRIEF DESCRIPTION OF THE DRAWINGS

FIG. 9A, left panel: cDC; right panel: cDC1. FIG. 9B, left panel: cDC2; right panel: pDC. The antibody treatments were administered at a dose of 0.1 mg/kg, 1 mg/kg, or 10 mg/kg for each antibody (n=5/group). Kruskal-Wallis with Dunn's multiple comparison test was applied. Data are presented as mean±SEM, * p<0.05.

DETAILED DESCRIPTION OF THE INVENTION

Figure 1:
FIG. 1 is a graph showing proliferation of EOL-1 cells after treatment with the indicated anti-FLT3 antibodies. Data are normalized to untreated control and each bar represents mean±SEM (n=3).

The present disclosure provides new agonistic anti-human FLT3 antibodies that can be used to stimulate FLT3 activity in a patient, such as a cancer patient. Unless otherwise stated, as used herein, "FLT3" refers to human FLT3. A human FLT3 polypeptide sequence is available under UniProt Accession No. P36888 (FLT3_HUMAN) (SEQ ID NO: 77), as shown below:

```
         10         20         30         40
MPALARDGGQ LPLLVVFSAM IFGTITNQDL PVIKCVLINH 50         60         70         80
KNNDSSVGKS SSYPMVSESP EDLGCALRPQ SSGTVYEAAA 90        100        110        120
VEVDVSASIT LQVLVDAPGN ISCLWVFKHS SLNCQPHFDL 130        140        150        160
QNRGVVSMVI LKMTETQAGE YLLFIQSEAT NYTILFTVSI 170        180        190        200
RNTLLYTLRR PYFRKMENQD ALVCISESVP EPIVEWVLCD 210        220        230        240
SQGESCKEES PAVVKKEEKV LHELFGTDIR CCARNELGRE 250        260        270        280
CTRLFTIDLN QTPQTTLPQL FLKVGEPLWI RCKAVHVNHG 290        300        310        320
FGLTWELENK ALEEGNYFEM STYSTNRTMI RILFAFVSSV 330        340        350        360
ARNDTGYYTC SSSKHPSQSA LVTIVEKGFI NATNSSEDYE
```

-continued

```
            370        380        390        400
     IDQYEEFCFS VRFKAYPQIR CTWTFSRKSF PCEQKGLDNG 410        420        430        440
     YSISKFCNHK HQPGEYIFHA ENDDAQFTKM FTLNIRRKPQ 450        460        470        480
     VLAEASASQA SCFSDGYPLP SWTWKKCSDK SPNCTEEITE 490        500        510        520
     GVWNRKANRK VFGQWVSSST LNMSEAIKGF LVKCCAYNSL 530        540        550        560
     GTSCETILLN SPGPFPFIQD NISFYATIGV CLLFIVVLTL 570        580        590        600
     LICHKYKKQF RYESQLQMVQ VTGSSDNEYF YVDFREYEYD 610        620        630        640
     LKWEFPRENL EFGKVLGSGA FGKVMNATAY GISKTGVSIQ 650        660        670        680
     VAVKMLKEKA DSSEREALMS ELKMMTQLGS HENIVNLLGA 690        700        710        720
     CTLSGPIYLI FEYCCYGDLL NYLRSKREKF HRTWTEIFKE 730        740        750        760
     HNFSFYPTFQ SHPNSSMPGS REVQIHPDSD QISGLHGNSF 770        780        790        800
     HSEDEIEYEN QKRLEEEEDL NVLTFEDLLC FAYQVAKGME 810        820        830        840
     FLEFKSCVHR DLAARNVLVT HGKVVKICDF GLARDIMSDS 850        860        870        880
     NYVVRGNARL PVKWMAPESL FEGIYTIKSD VWSYGILLWE 890        900        910        920
     IFSLGVNPYP GIPVDANFYK LIQNGFKMDQ PFYATEEIYI 930        940        950        960
     IMQSCWAFDS RKRPSFPNLT SFLGCQLADA EEAMYQNVDG 970        980        990
     RVSECPHTYQ NRRPFSREMD LGLLSPQAQV EDS
```

The term "antibody" (Ab) or "immunoglobulin" (Ig), as used herein, refers to a tetramer comprising two heavy (H) chains (about 50-70 kDa) and two light (L) chains (about 25 kDa) inter-connected by disulfide bonds. Each heavy chain is comprised of a heavy chain variable domain (VH) and a heavy chain constant region (CH). Each light chain is composed of a light chain variable domain (VL) and a light chain constant region (CL). The VH and VL domains can be subdivided further into regions of hypervariability, termed "complementarity determining regions" (CDRs), interspersed with regions that are more conserved, termed "framework regions" (FRs). Each VH and VL is composed of three CDRs (H-CDR herein designates a CDR from the heavy chain; and L-CDR herein designates a CDR from the light chain) and four FRs, arranged from amino-terminus to carboxyl-terminus in the following order: FR1, CDR1, FR2, CDR2, FR3, CDR3, FR4. The assignment of amino acid numbers, and of FR and CDR regions, in the heavy or light chain may be in accordance with IMGT® definitions (Eu numbering; Lefranc et al., *Dev Comp Immunol* (2003) 27(1):55-77); or the definitions of Kabat, *Sequences of Proteins of Immunological Interest* (National Institutes of Health, Bethesda, MD (1987 and 1991)); Chothia & Lesk, *J. Mol. Biol.* (1987) 196:901-17; Chothia et al., *Nature* (1989) 342:878-83; MacCallum et al., *J. Mol. Biol.* (1996) 262: 732-45; or Honegger and Plückthun, *J. Mol. Biol.* (2001) 309(3):657-70.

The term "recombinant antibody" refers to an antibody that is expressed from a cell or cell line comprising the nucleotide sequence(s) that encode the antibody, wherein said nucleotide sequence(s) are not naturally associated with the cell.

The term "isolated protein," "isolated polypeptide," or "isolated antibody" refers to a protein, polypeptide or antibody that by virtue of its origin or source of derivation (1) is not associated with naturally associated components that accompany it in its native state, (2) is free of other proteins from the same species, (3) is expressed by a cell from a different species, and/or (4) does not occur in nature. Thus, a polypeptide that is chemically synthesized or synthesized in a cellular system different from the cell from which it naturally originates will be "isolated" from its naturally associated components. A protein may also be rendered substantially free of naturally associated components by isolation, using protein purification techniques well known in the art.

The term "affinity" refers to a measure of the attraction between an antigen and an antibody. The intrinsic attractiveness of the antibody for the antigen is typically expressed as the binding affinity equilibrium constant ($K_D$) of a particular antibody-antigen interaction. An antibody is said to specifically bind to an antigen when the $K_D$ is ≤1 mM, e.g., ≤1 µM, ≤100 nM, or ≤10 nM. A $K_D$ binding affinity constant can be measured, e.g., by surface plasmon resonance (e.g., BIAcore™) using, for example, the IBIS MX96 SPR system from IBIS Technologies or the Carterra LSA SPR platform, or by Bio-Layer Interferometry, for example using the Octet™ system from ForteBio.

The term "epitope" as used herein refers to a portion (determinant) of an antigen that specifically binds to an antibody or a related molecule such as a bi-specific binding molecule. Epitopic determinants generally consist of chemically active surface groupings of molecules such as amino acids or carbohydrate or sugar side chains and generally have specific three-dimensional structural characteristics, as well as specific charge characteristics. An epitope may be "linear" or "conformational." In a linear epitope, all of the points of interaction between a protein (e.g., an antigen) and an interacting molecule (such as an antibody) occur linearly along the primary amino acid sequence of the protein. In a conformational epitope, the points of interaction occur across amino acid residues on the protein that are separated from one another in the primary amino acid sequence. Once a desired epitope on an antigen is determined, it is possible to generate antibodies to that epitope using techniques well known in the art. For example, an antibody to a linear epitope may be generated, e.g., by immunizing an animal with a peptide having the amino acid residues of the linear epitope. An antibody to a conformational epitope may be generated, e.g., by immunizing an animal with a mini-domain containing the relevant amino acid residues of the conformational epitope. An antibody to a particular epitope can also be generated, e.g., by immunizing an animal with the target molecule of interest (e.g., FLT3) or a relevant portion thereof, then screening for binding to the epitope.

One can determine whether an antibody binds to the same epitope as or competes for binding with an anti-FLT3 antibody of the present disclosure by using methods known in the art, including, without limitation, competition assays, epitope binning, and alanine scanning. In some embodiments, one allows the anti-FLT3 antibody of the present disclosure to bind to FLT3 under saturating conditions, and then measures the ability of the test antibody to bind to FLT3. If the test antibody is able to bind to FLT3 at the same time as the reference anti-FLT3 antibody, then the test antibody binds to a different epitope than the reference anti-FLT3 antibody. However, if the test antibody is not able to bind to FLT3 at the same time, then the test antibody binds to the same epitope, an overlapping epitope, or an epitope that is in close proximity to the epitope bound by the anti-FLT3 antibody of the present disclosure. This experiment can be performed using, e.g., ELISA, RIA, BIA-CORE™ SPR, Bio-Layer Interferometry or flow cytometry. To test whether an anti-FLT3 antibody cross-competes with another anti-FLT3 antibody, one may use the competition method described above in two directions, i.e., determining if the known antibody blocks the test antibody and vice versa. Such cross-competition experiments may be performed, e.g., using an IBIS MX96 or Carterra LSA SPR instrument or the Octet™ system.

The term "human antibody" refers to an antibody in which the variable domain and constant region sequences are derived from human sequences. The term encompasses antibodies with sequences that are derived from human genes but have been modified, e.g., to decrease immunogenicity, increase affinity, and/or increase stability. Further, the term encompasses antibodies produced recombinantly in nonhuman cells, which may impart glycosylation not typical of human cells. The term also encompasses antibodies produced in transgenic nonhuman organisms with human antibody genes (e.g., OmniRat® rats).

The term "antigen-binding portion" of an antibody (or simply "antibody portion"), as used herein, refers to one or more portions or fragments of an antibody that retain the ability to specifically bind to an antigen (e.g., human FLT3, or a portion thereof). It has been shown that certain fragments of a full-length antibody can perform the antigen-binding function of the antibody. Examples of binding fragments encompassed within the term "antigen-binding portion" include (i) a Fab fragment: a monovalent fragment consisting of the VL, VH, CL and CH1 domains; (ii) a F(ab')2 fragment: a bivalent fragment comprising two Fab fragments linked by a disulfide bridge at the hinge region; (iii) an Fd fragment consisting of the VH and CH1 domains; (iv) an Fv fragment consisting of the VL and VH domains of a single arm of an antibody, (v) a dAb fragment, which consists of a VH domain; and (vi) an isolated complementarity determining region (CDR) capable of specifically binding to an antigen. Furthermore, although the two domains of the Fv fragment, VL and VH, are encoded by separate genes, they can be joined, using recombinant methods, by a synthetic linker that enables them to be made as a single protein chain in which the VL and VH domains pair to form monovalent molecules (known as single chain Fv (scFv)). Also within the present disclosure are antigen-binding molecules comprising a VH and/or a VL. In the case of a VH, the molecule may also comprise one or more of a CH1, hinge, CH2, or CH3 region. Such single chain antibodies are also intended to be encompassed within the term "antigen-binding portion" of an antibody. Other forms of single chain antibodies, such as diabodies, are also encompassed. Diabodies are bivalent, bi-specific antibodies in which VH and VL domains are expressed on a single polypeptide chain, but using a linker that is too short to allow for pairing between the two domains on the same chain, thereby forcing the domains to pair with complementary domains of another chain and creating two antigen-binding sites.

Antibody portions, such as Fab and F(ab')$_2$ fragments, can be prepared from whole antibodies using conventional techniques, such as papain or pepsin digestion of whole antibodies. Moreover, antibodies, antibody portions and immunoadhesin molecules can be obtained using standard recombinant DNA techniques, e.g., as described herein.

The class (isotype) and subclass of anti-FLT3 antibodies may be determined by any method known in the art. In general, the class and subclass of an antibody may be determined using antibodies that are specific for a particular class and subclass of antibody. Such antibodies are available commercially. The class and subclass can be determined by ELISA or Western blot as well as other techniques. Alternatively, the class and subclass may be determined by sequencing all or a portion of the constant region of the heavy and/or light chains of the antibodies, comparing their amino acid sequences to the known amino acid sequences of various classes and subclasses of immunoglobulins, and determining the class and subclass of the antibodies.

Unless otherwise indicated, all antibody amino acid residue numbers referred to in this disclosure are those under the IMGT® numbering scheme (Eu numbering).

Anti-FLT3 Antibodies

The present disclosure provides antibodies directed against FLT3, and antigen-binding portions thereof. In a particular embodiment, the antibodies disclosed herein are *human antibodies* generated from transgenic animals (e.g., rats) that are able to produce antibodies encoded by rearranged human antibody genes. In certain embodiments, the human antibodies may contain certain mutations, e.g., to change primer-derived mutations back to the germline sequence (see, e.g., the "Symplex-corrected" variant sequences in Table 1).

In some embodiments, the anti-FLT3 antibodies of the present disclosure have the "LALA" mutations (L234A/L235A) in the Fc region. These mutations hinder the antibodies' binding to human FcγR (Fc gamma receptors). Such antibodies are advantageous because they have a low level of secondary effector functions and hence do not deplete effector T cells or target other non-malignant cells.

In some embodiments, the anti-FLT3 antibody or antigen-binding portion competes or cross-competes for binding to human FLT3 with, or binds to the same epitope of human FLT3 as, an antibody comprising:

a) a heavy chain (HC) comprising the amino acid sequences of SEQ ID NOs: 3 and 75 and a light chain (LC) comprising the amino acid sequences of SEQ ID NOs: 4 and 76;

b) an HC comprising the amino acid sequences of SEQ ID NOs: 13 and 75 and an LC comprising the amino acid sequences of SEQ ID NOs: 14 and 76;

c) an HC comprising the amino acid sequences of SEQ ID NOs: 23 and 75 and an LC comprising the amino acid sequences of SEQ ID NOs: 24 and 76;

d) an HC comprising the amino acid sequences of SEQ ID NOs: 33 and 75 and an LC comprising the amino acid sequences of SEQ ID NOs: 34 and 76;

e) an HC comprising the amino acid sequences of SEQ ID NOs: 43 and 75 and an LC comprising the amino acid sequences of SEQ ID NOs: 44 and 76;

f) an HC comprising the amino acid sequences of SEQ ID NOs: 53 and 75 and an LC comprising the amino acid sequences of SEQ ID NOs: 54 and 76;

g) an HC comprising the amino acid sequences of SEQ ID NOs: 63 and 75 and an LC comprising the amino acid sequences of SEQ ID NOs: 64 and 76; or h) an HC comprising the amino acid sequences of SEQ ID NOs: 73 and 75 and an LC comprising the amino acid sequences of SEQ ID NOs: 74 and 76.

In some embodiments, the anti-FLT3 antibody or antigen-binding portion has a heavy chain CDR3 (H-CDR3) amino acid sequence of SEQ ID NO: 7, 17, 27, 37, 47, 57, or 67.

In some embodiments, the anti-FLT3 antibody or antigen-binding portion has heavy chain CDR1-3 (H-CDR1-3) comprising the amino acid sequences of SEQ ID NOs: 5-7, 15-17, 25-27, 35-37, 45-47, 55-57, or 65-67, respectively.

In some embodiments, the anti-FLT3 antibody or antigen-binding portion has a heavy chain variable domain (VH) amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 3, 13, 23, 33, 43, 53, 63, or 73.

In some embodiments, the anti-FLT3 antibody or antigen-binding portion has a VH comprising the amino acid sequence of SEQ ID NO: 3, 13, 23, 33, 43, 53, 63, or 73.

In some embodiments, the anti-FLT3 antibody has a VH amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 3, 13, 23, 33, 43, 53, 63, or 73; and a heavy chain constant region amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 75.

In some embodiments, the anti-FLT3 antibody comprises a VH amino acid sequence of SEQ ID NO: 3, 13, 23, 33, 43, 53, 63, or 73 and a heavy chain constant region amino acid sequence of SEQ ID NO: 75.

In some embodiments, the anti-FLT3 antibody or antigen-binding portion has a light chain CDR3 (L-CDR3) amino acid sequence of SEQ ID NO: 10, 20, 30, 40, 50, 60, or 70.

In some embodiments, the anti-FLT3 antibody or antigen-binding portion has light chain CDR1-3 (L-CDR1-3) comprising the amino acid sequences of SEQ ID NOs: 8-10, 18-20, 28-30, 38-40, 48-50, 58-60, or 68-70, respectively.

In some embodiments, the anti-FLT3 antibody or antigen-binding portion has a light chain variable domain (VL) amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 4, 14, 24, 34, 44, 54, 64, or 74.

In some embodiments, the anti-FLT3 antibody or antigen-binding portion has a VL comprising the amino acid sequence of SEQ ID NO: 4, 14, 24, 34, 44, 54, 64, or 74.

In some embodiments, the anti-FLT3 antibody has a VL amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 4, 14, 24, 34, 44, 54, 64, or 74; and a light chain constant region amino acid sequence that is at least 80%, 85%, 90%, 91%, 92%, 93%, 94%, 95%, 96%, 97%, 98%, or 99% identical (e.g., at least 90% identical) to the amino acid sequence of SEQ ID NO: 76.

In some embodiments, the anti-FLT3 antibody comprises a VL amino acid sequence of SEQ ID NO: 4, 14, 24, 34, 44, 54, 64, or 74 and a light chain constant region amino acid sequence of SEQ ID NO: 76.

In certain embodiments, the anti-FLT3 antibody comprises any one of the above-described heavy chains and any one of the above-described light chains.

In some embodiments, the anti-FLT3 antibody or antigen-binding portion of the present disclosure comprises the H-CDR1-3 and L-CDR1-3 amino acid sequences of:
  a) SEQ ID NOs: 5-10, respectively;
  b) SEQ ID NOs: 15-20, respectively;
  c) SEQ ID NOs: 25-30, respectively;
  d) SEQ ID NOs: 35-40, respectively;
  e) SEQ ID NOs: 45-50, respectively;
  f) SEQ ID NOs: 55-60, respectively; or
  g) SEQ ID NOs: 65-70, respectively.

In some embodiments, the anti-FLT3 antibody or antigen-binding portion of the present disclosure comprises a VH and a VL that are at least 80%, 85%, 90%, 91%, 92%, 93%, 94%, 95%, 96%, 97%, 98%, or 99% identical (e.g., at least 90% identical) to the amino acid sequences of:
  a) SEQ ID NOs: 3 and 4, respectively;
  b) SEQ ID NOs: 13 and 14, respectively;
  c) SEQ ID NOs: 23 and 24, respectively;
  d) SEQ ID NOs: 33 and 34, respectively;
  e) SEQ ID NOs: 43 and 44, respectively;
  f) SEQ ID NOs: 53 and 54, respectively;
  g) SEQ ID NOs: 63 and 64, respectively; or
  h) SEQ ID NOs: 73 and 74, respectively.

In some embodiments, the anti-FLT3 antibody or antigen-binding portion of the present disclosure comprises a VH and a VL that comprise the amino acid sequences of:
  a) SEQ ID NOs: 3 and 4, respectively;
  b) SEQ ID NOs: 13 and 14, respectively;
  c) SEQ ID NOs: 23 and 24, respectively;
  d) SEQ ID NOs: 33 and 34, respectively;
  e) SEQ ID NOs: 43 and 44, respectively;
  f) SEQ ID NOs: 53 and 54, respectively;
  g) SEQ ID NOs: 63 and 64, respectively; or
  h) SEQ ID NOs: 73 and 74, respectively.

In some embodiments, the anti-FLT3 antibody of the present disclosure comprises:
  a) an HC comprising the amino acid sequences of SEQ ID NOs: 3 and 75 and an LC comprising the amino acid sequences of SEQ ID NOs: 4 and 76;
  b) an HC comprising the amino acid sequences of SEQ ID NOs: 13 and 75 and an LC comprising the amino acid sequences of SEQ ID NOs: 14 and 76;
  c) an HC comprising the amino acid sequences of SEQ ID NOs: 23 and 75 and an LC comprising the amino acid sequences of SEQ ID NOs: 24 and 76;
  d) an HC comprising the amino acid sequences of SEQ ID NOs: 33 and 75 and an LC comprising the amino acid sequences of SEQ ID NOs: 34 and 76;
  e) an HC comprising the amino acid sequences of SEQ ID NOs: 43 and 75 and an LC comprising the amino acid sequences of SEQ ID NOs: 44 and 76;
  f) an HC comprising the amino acid sequences of SEQ ID NOs: 53 and 75 and an LC comprising the amino acid sequences of SEQ ID NOs: 54 and 76;
  g) an HC comprising the amino acid sequences of SEQ ID NOs: 63 and 75 and an LC comprising the amino acid sequences of SEQ ID NOs: 64 and 76; or
  h) an HC comprising the amino acid sequences of SEQ ID NOs: 73 and 75 and an LC comprising the amino acid sequences of SEQ ID NOs: 74 and 76.

The present disclosure also provides an anti-FLT3 antibody or an antigen-binding portion thereof that competes or cross-competes for binding with, or binds to the same epitope as, antibody 17566, 17526, 17667, 17667-0, 17679, 17494, 17543, or 17497.

In some embodiments, the anti-FLT3 antibody or antigen-binding portion of the present disclosure comprises the H-CDR1-3 and L-CDR1-3 amino acid sequences of antibody 17566, 17526, 17667, 17667-0, 17679, 17494, 17543, or 17497.

In some embodiments, the anti-FLT3 antibody or antigen-binding portion of the present disclosure comprises a VH and a VL that are at least 80%, 85%, 90%, 91%, 92%, 93%, 94%, 95%, 96%, 97%, 98%, or 99% identical (e.g., at least 90% identical) in amino acid sequence to the VH and VL, respectively, of antibody 17566, 17526, 17667, 17667-0, 17679, 17494, 17543, or 17497.

In some embodiments, the anti-FLT3 antibody or antigen-binding portion of the present disclosure comprises a VH and a VL that are the VH and VL, respectively, of antibody 17566, 17526, 17667, 17667-0, 17679, 17494, 17543, or 17497.

In some embodiments, the anti-FLT3 antibody of the present disclosure is antibody 17566, 17526, 17667, 17667-0, 17679, 17494, 17543, or 17497, or an antibody with the same amino acid sequences as said antibody.

The class of an anti-FLT3 antibody obtained by the methods described herein may be changed or switched with another class or subclass. In some embodiments of the present disclosure, a nucleic acid molecule encoding VL or VH is isolated using methods well known in the art such that it does not include nucleic acid sequences encoding CL or CH, respectively. The nucleic acid molecules encoding VL or VH then are operatively linked to a nucleic acid sequence encoding a CL or CH, respectively, from a different class of immunoglobulin molecule. This may be achieved using a vector or nucleic acid molecule that comprises a CL or CH sequence, as described above. For example, an anti-FLT3 antibody that was originally IgM may be class switched to IgG. Further, the class switching may be used to convert one IgG subclass to another, e.g., from $IgG_1$ to $IgG_2$. A κ light chain constant region can be changed, e.g., to a λ light chain constant region, or vice-versa. An exemplary method for producing an antibody of the present disclosure with a desired Ig isotype comprises the steps of isolating a nucleic acid molecule encoding the heavy chain of an anti-FLT3 antibody and a nucleic acid molecule encoding the light chain of an anti-FLT3 antibody, obtaining the variable domain of the heavy chain, ligating a coding sequence for the variable domain of the heavy chain with a coding sequence for the constant region of a heavy chain of the desired isotype, expressing the light chain and the heavy chain encoded by the ligated sequence in a cell, and collecting the anti-FLT3 antibody with the desired isotype.

The anti-FLT3 antibody of the present disclosure can be an IgG, an IgM, an IgE, an IgA, or an IgD molecule, but is typically of the IgG isotype, e.g., of IgG subclass $IgG_1$, $IgG_{2a}$ or $IgG_{2b}$, $IgG_3$ or $IgG_4$. In some embodiments, the antibody is of the isotype subclass $IgG_1$.

In some embodiments, the anti-FLT3 antibody may comprise at least one mutation in the Fc region. A number of different Fc mutations are known, where these mutations alter the antibody's effector function. For example, in some embodiments, the anti-FLT3 antibody comprises at least one mutation in the Fc region that reduces effector function, e.g., mutations at one or more of positions 228, 233, 234 and 235, where amino acid positions are numbered according to the IMGT® numbering scheme.

In some embodiments, e.g., where the antibody is of the IgG, subclass, one or both of the amino acid residues at positions 234 and 235 may be mutated, for example from Leu to Ala (L234A/L235A). These mutations reduce effector function of the Fc region of $IgG_1$ antibodies. The amino acid positions are numbered according to the IMGT® numbering scheme.

In some embodiments, e.g., where the antibody is of the $IgG_4$ subclass, it may comprise the mutation S228P, where the amino acid position is numbered according to the IMGT® numbering scheme. This mutation is known to reduce undesired Fab arm exchange.

In some embodiments, the anti-FLT3 antibody or antigen-binding portion of the present disclosure is agonistic.

In some embodiments, the anti-FLT3 antibody or antigen-binding portion stimulates proliferation of EOL-1 cells in vitro (e.g., at a concentration of 5, 10, 15, 20, 25, 30, 35, 40, 45, or 50 µg/mL or less, such as at a concentration of 25 µg/mL or less).

In some embodiments, the anti-FLT3 antibody or antigen-binding portion stimulates proliferation of OCI-AML5 cells in vitro (e.g., at a concentration of 5, 10, 15, 20, 25, 30, 35, 40, 45, or 50 µg/mL or less, such as at a concentration of 25 µg/mL or less).

In some embodiments, the anti-FLT3 antibody or antigen-binding portion specifically binds to human FLT3 and to cynomolgus FLT3 (e.g., expressed on CHO-S cells). In some embodiments, the anti-FLT3 antibody or antigen-binding portion specifically binds to human FLT3, cynomolgus FLT3, and mouse FLT3 (e.g., expressed on CHO-S cells).

In some embodiments, the anti-FLT3 antibody or antigen-binding portion does not block FLT3L binding to human FLT3 in vitro. In certain embodiments, the anti-FLT3 antibody or antigen-binding portion does not block FLT3L binding to immobilized FLT3 at saturating conditions.

In some embodiments, the anti-FLT3 antibody or antigen-binding portion does not block binding of FLT3L-Fc to cell-displayed human, cynomolgus, and/or mouse FLT3 protein in vitro (e.g., at a concentration of at least 0.1, 0.5, 1, 5, 10, 30, 50, or 100 µg/mL, such as at a concentration of at least 30 µg/mL).

In some embodiments, the anti-FLT3 antibody or antigen-binding portion stimulates proliferation of primary human CD34$^+$ stem cells (e.g., at a concentration of 5, 10, 15, 20, 25, 30, 35, 40, 45, or 50 µg/mL or less, such as at a concentration of 25 µg/mL or less).

In some embodiments, the anti-FLT3 antibody or antigen-binding portion stimulates differentiation of primary human CD34$^+$ stem cells (e.g., at a concentration of 5, 10, 15, 20, 25, 30, 35, 40, 45, or 50 µg/mL or less, such as at a concentration of 25 µg/mL or less).

In some embodiments, the anti-FLT3 antibody or antigen-binding portion increases dendritic cell subpopulations such as CD14$^+$, CD1c$^+$, pDC, cDC, cDC1, or cDC2 cells, or any combination thereof (e.g., at a concentration of 5, 10, 15, 20, 25, 30, 35, 40, 45, or 50 µg/mL or less, such as at a concentration of 25 µg/mL or less).

In some embodiments, the anti-FLT3 antibody or antigen-binding portion induces dendritic cell expansion and/or mobilization in immunocompetent mice such as Balb/c mice (e.g., at a dose of 0.1, 1, or 10 mg/kg or less twice weekly).

In some embodiments, the anti-FLT3 antibody or antigen-binding portion induces dendritic cell expansion and/or mobilization in immunocompromised mice reconstituted with human CD34$^+$ stem cells (e.g., at a dose of 1 or 10 mg/kg or less twice weekly). In certain embodiments, dendritic cell expansion and/or mobilization is induced in the spleen, bone marrow, or both, of the mice.

In some embodiments, the anti-FLT3 antibody or antigen-binding portion binds to human FLT3 with a $K_D$ of about 20, 15, 10, 9, 8, 7, 6, 5, 4, or 3 nM or less (e.g., 9 nM or less).

In some embodiments, the anti-FLT3 antibody or antigen-binding portion binds to domain 1 (D1) of the extracellular domain (ECD) of human FLT3. In certain embodiments, the antibody or portion binds to residues at the C-terminal end of D1 (e.g., on the inner surface of D1 relative to the FLT3 ligand). In certain embodiments, the antibody or portion binds to residues on the outer surface of D1 relative to the FLT3 ligand. In particular embodiments, the distance between the two epitopes on each D1 in the FLT3 ligand/receptor complex is 90-120 Å.

In some embodiments, the anti-FLT3 antibody or antigen-binding portion binds to a linear epitope comprising residues 78-87, 78-97, or 138-147 of the human FLT3 amino acid sequence. In some embodiments, the anti-FLT3 antibody or antigen-binding portion binds to an epitope that comprises residue A79, in combination with residues A80 and/or V81, of the human FLT3 amino acid sequence. In particular embodiments, the anti-FLT3 antibody or antigen-binding portion binds to an epitope comprising the following residues of the human FLT3 amino acid sequence:
  a) A79, A80, V81, T157, R161;
  b) A79, A80, V81, I89, T90, R161,
  c) A79, V81;
  d) A79, V81, V83, A87, I89, V125, T157; or
  e) N100, L104-V106, H109-S111, E140, L142, N151, T153.

The antibody or antigen-binding portion may bind, for example, to an epitope as shown for antibody 17566, 17526, 17667, 17667-0, 17679, 17494, 17543, or 17497 in Table 8. In certain embodiments, the antibody or antigen-binding portion does not bind to the same epitope as antibody IMC-EB10.

The present disclosure also contemplates an anti-FLT3 antibody or antigen-binding portion described herein with any combination of the above properties.

In some embodiments, an anti-FLT3 antibody or antigen-binding portion described herein has at least one (e.g., 1, 2, 3, 4, 5, 6, 7, 8, 9, 10, or all 11) of the following properties:
  a) stimulates proliferation of EOL-1 cells in vitro;
  b) stimulates proliferation of OCI-AML5 cells in vitro;
  c) binds to human FLT3 with a $K_D$ of 20 nM or less;
  d) specifically binds to cynomolgus FLT3;
  e) specifically binds to mouse FLT3;
  f) does not block FLT3 ligand binding to human FLT3 in vitro;
  g) does not block binding of FLT3L-Fc to cell-displayed human, cynomolgus, or mouse FLT3 protein in vitro;
  h) stimulates proliferation of primary human $CD34^+$ stem cells;
  i) stimulates differentiation of primary human $CD34^+$ stem cells;
  j) induces dendritic cell mobilization in vivo in Balb/c mice; and
  k) induces dendritic cell mobilization in vivo in immunocompromised mice reconstituted with human $CD34^+$ stem cells.

For example, in certain embodiments, an anti-FLT3 antibody or antigen-binding portion described herein may have properties a) and c)-h); a), c), d), and f)-i); a), c), d), and f)-h); a), c), and f)-h); a)-c), h), i), and k); a)-c), h), and i); or a)-c) and j).

In some embodiments, an anti-FLT3 antibody or antigen-binding portion described herein may increase dendritic cell proliferation and/or activation in a patient. In some embodiments, an anti-FLT3 antibody or antigen-binding portion described herein enhances the ability of dendritic cells to take up tumor antigens.

In some embodiments, an anti-FLT3 antibody or antigen-binding portion described herein may inhibit tumor growth and/or induce tumor growth regression in vivo. In some embodiments, an anti-FLT3 antibody or antigen-binding portion described herein may slow down or reverse metastasis in a cancer patient. In some embodiments, an anti-FLT3 antibody or antigen-binding portion described herein may prolong survival of a cancer patient. Any combination of the above properties is also contemplated.

In certain embodiments, an antibody or antigen-binding portion thereof of the present disclosure may be part of a larger immunoadhesin molecule, formed by covalent or noncovalent association of the antibody or antibody portion with one or more other proteins or peptides. Examples of such immunoadhesin molecules include use of the streptavidin core region to make a tetrameric scFv molecule (Kipriyanov et al., *Human Antibodies and Hybridomas* (1995) 6:93-101) and use of a cysteine residue, a marker peptide and a C-terminal polyhistidine tag to make bivalent and biotinylated scFv molecules (Kipriyanov et al., *Mol. Immunol.* (1994) 31:1047-58). Other examples include where one or more CDRs from an antibody are incorporated into a molecule either covalently or noncovalently to make it an immunoadhesin that specifically binds to an antigen of interest. In such embodiments, the CDR(s) may be incorporated as part of a larger polypeptide chain, may be covalently linked to another polypeptide chain, or may be incorporated noncovalently.

In another embodiment, a fusion antibody or immunoadhesin may be made that comprises all or a portion of an anti-FLT3 antibody of the present disclosure linked to another polypeptide. In certain embodiments, only the variable domains of the anti-FLT3 antibody are linked to the polypeptide. In certain embodiments, the VH domain of an anti-FLT3 antibody is linked to a first polypeptide, while the VL domain of an anti-FLT3 antibody is linked to a second polypeptide that associates with the first polypeptide in a manner such that the VH and VL domains can interact with one another to form an antigen-binding site. In some embodiments, the VH domain is separated from the VL domain by a linker such that the VH and VL domains can interact with one another (e.g., single-chain antibodies). The VH-linker-VL antibody is then linked to the polypeptide of interest. In addition, fusion antibodies can be created in which two (or more) single-chain antibodies are linked to one another. This is useful if one wants to create a divalent or polyvalent antibody on a single polypeptide chain, or if one wants to create a bi-specific antibody.

To create a single chain antibody (scFv), the VH- and VL-encoding DNA fragments are operatively linked to another fragment encoding a flexible linker, e.g., encoding the amino acid sequence $(Gly_4\text{-}Ser)_3$ (SEQ ID NO: 78), such that the VH and VL sequences can be expressed as a contiguous single-chain protein, with the VL and VH domains joined by the flexible linker. See, e.g., Bird et al., *Science* (1988) 242:423-6; Huston et al., *Proc. Natl. Acad. Sci. USA* (1988) 85:5879-83; and McCafferty et al., *Nature* (1990) 348:552-4. The single chain antibody may be monovalent, if only a single VH and VL are used; bivalent, if two VH and VL are used; or polyvalent, if more than two VH and VL are used. Bi-specific or polyvalent antibodies may be generated that bind specifically to human FLT3 and to another molecule, for instance.

In other embodiments, other modified antibodies may be prepared using anti-FLT3 antibody-encoding nucleic acid molecules. For instance, "kappa bodies" (Ill et al., *Protein Eng.* (1997) 10:949-57), "minibodies" (Martin et al., *EMBO J.* (1994) 13:5303-9), "diabodies" (Holliger et al., *Proc. Natl. Acad. Sci. USA* (1993) 90:6444-8), or "Janusins" (Traunecker et al., *EMBO J.* (1991) 10:3655-9 and Traunecker et al., *Int. J. Cancer* (Suppl.) (1992) 7:51-2) may be prepared using standard molecular biological techniques following the teachings of the specification.

An anti-FLT3 antibody or antigen-binding portion of the present disclosure can be derivatized or linked to another molecule (e.g., another peptide or protein). In general, the antibodies or portions thereof are derivatized such that FLT3 binding is not affected adversely by the derivatization or labeling. Accordingly, the antibodies and antibody portions of the present disclosure are intended to include both intact and modified forms of the human anti-FLT3 antibodies described herein. For example, an antibody or antibody portion of the present disclosure can be functionally linked (by chemical coupling, genetic fusion, noncovalent association or otherwise) to one or more other molecular entities, such as another antibody (e.g., a bi-specific antibody or a diabody), a detection agent, a pharmaceutical agent, and/or a protein or peptide that can mediate association of the antibody or antibody portion with another molecule (such as a streptavidin core region or a polyhistidine tag).

One type of derivatized antibody is produced by crosslinking two or more antibodies (of the same type or of different types, e.g., to create bi-specific antibodies). Suitable crosslinkers include those that are heterobifunctional, having two distinctly reactive groups separated by an appropriate spacer (e.g., m-maleimidobenzoyl-N-hydroxysuccinimide ester) or homobifunctional (e.g., disuccinimidyl suberate). Such linkers are available, e.g., from Pierce Chemical Company, Rockford, IL.

An anti-FLT3 antibody or antigen-binding portion can also be derivatized with a chemical group such as polyethylene glycol (PEG), a methyl or ethyl group, or a carbohydrate group. These groups may be useful to improve the biological characteristics of the antibody, e.g., to increase serum half-life.

An antibody or antigen-binding portion according to the present disclosure may also be labeled. As used herein, the terms "label" or "labeled" refer to incorporation of another molecule in the antibody. In some embodiments, the label is a detectable marker, e.g., incorporation of a radiolabeled amino acid or attachment to a polypeptide of biotinyl moieties that can be detected by marked avidin (e.g., streptavidin containing a fluorescent marker or enzymatic activity that can be detected by optical or colorimetric methods). In some embodiments, the label or marker can be therapeutic, e.g., a drug conjugate or toxin. Various methods of labeling polypeptides and glycoproteins are known in the art and may be used. Examples of labels for polypeptides include, but are not limited to, the following: radioisotopes or radionuclides (e.g., 3H, 14C, 15N, 35S, 90Y, 99Tc, 111In, 125I, 131I), fluorescent labels (e.g., FITC, rhodamine, lanthanide phosphors), enzymatic labels (e.g., horseradish peroxidase, β-galactosidase, luciferase, alkaline phosphatase), chemiluminescent markers, biotinyl groups, predetermined polypeptide epitopes recognized by a secondary reporter (e.g., leucine zipper pair sequences, binding sites for secondary antibodies, metal binding domains, epitope tags), magnetic agents such as gadolinium chelates, toxins such as pertussis toxin, taxol, cytochalasin B, gramicidin D, ethidium bromide, emetine, mitomycin, etoposide, tenoposide, vincristine, vinblastine, colchicine, doxorubicin, daunorubicin, dihydroxy anthracin dione, mitoxantrone, mithramycin, actinomycin D, 1-dehydrotestosterone, glucocorticoids, procaine, tetracaine, lidocaine, propranolol, and puromycin and analogs or homologs thereof. In some embodiments, labels are attached by spacer arms of various lengths to reduce potential steric hindrance.

In some embodiments, an antibody or antigen-binding portion according to the present disclosure may be conjugated to a cytotoxic agent to form an immunoconjugate. In some embodiments, an antibody or antigen-binding portion according to the present disclosure may be conjugated to a radioisotope.

In certain embodiments, the antibodies of the present disclosure may be present in a neutral form (including zwitterionic forms) or as a positively or negatively-charged species. In some embodiments, the antibodies may be complexed with a counterion to form a pharmaceutically acceptable salt.

Anti-FLT3 Antibody Compositions

The present disclosure also provides a combination therapy (e.g., a composition) that comprises one, two, three, four, or more of the anti-FLT3 antibodies or antigen-binding portions thereof described herein. In certain embodiments, the combination therapy (e.g., composition) comprises two of the anti-FLT3 antibodies or antigen-binding portions. The combination therapy may take the form of, e.g., a method of treatment using said antibodies or antigen-binding portions or a pharmaceutical composition comprising said antibodies or antigen-binding portions.

In some embodiments, the present disclosure provides a composition comprising a first anti-FLT3 antibody or an antigen-binding portion thereof and a second anti-FLT3 antibody or an antigen-binding portion thereof, wherein the first and second antibodies are:
  antibodies 17566 and 17526, respectively;
  antibodies 17566 and 17667 (or 17667-0), respectively;
  antibodies 17566 and 17679, respectively;
  antibodies 17566 and 17494, respectively;
  antibodies 17566 and 17543, respectively;
  antibodies 17566 and 17497, respectively;
  antibodies 17526 and 17667 (or 17667-0), respectively;
  antibodies 17526 and 17679, respectively;
  antibodies 17526 and 17494, respectively;
  antibodies 17526 and 17543, respectively;
  antibodies 17526 and 17497, respectively;
  antibodies 17667 (or 17667-0) and 17679, respectively;
  antibodies 17667 (or 17667-0) and 17494, respectively;
  antibodies 17667 (or 17667-0) and 17543, respectively;
  antibodies 17667 (or 17667-0) and 17497, respectively;
  antibodies 17679 and 17494, respectively;
  antibodies 17679 and 17543, respectively;
  antibodies 17679 and 17497, respectively;
  antibodies 17494 and 17543, respectively;
  antibodies 17494 and 17497, respectively;
  antibodies 17543 and 17497, respectively; or
  antibodies 17667 and 17667-0, respectively.

In some embodiments, the composition comprises antibodies or antigen-binding portions thereof that bind to the same epitope as, or compete for binding with, said first and second antibodies.

In some embodiments, the composition comprises an antibody or an antigen-binding portion thereof that comprises the H-CDR1-3 and L-CDR1-3 amino acid sequences of said first antibody, and an antibody or an antigen-binding portion thereof that comprises the H-CDR1-3 and L-CDR1-3 amino acid sequences of said second antibody.

In some embodiments, the composition comprises an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical (e.g., at least 90% identical) to the VH and VL amino acid sequences, respectively, of said first antibody, and an antibody or an antigen-binding portion thereof that comprises a VH and a VL with amino acid sequences that are at least 80%, 85%, 90%, 91%, 92%, 93%, 94%, 95%, 96%, 97%, 98%, or 99% identical (e.g., at least 90% identical) to the VH and VL amino acid sequences, respectively, of said second antibody.

In some embodiments, the composition comprises an antibody or an antigen-binding portion thereof that comprises the VH and VL amino acid sequences of said first antibody, and an antibody or an antigen-binding portion thereof that comprises the VH and VL amino acid sequences of said second antibody.

In some embodiments, the composition comprises an antibody or an antigen-binding portion thereof that comprises the HC and LC amino acid sequences of said first antibody, and an antibody or an antigen-binding portion thereof that comprises the HC and LC amino acid sequences of said second antibody.

In certain embodiments, said composition may comprise one, two, or more antibodies or antigen-binding portions thereof selected from the group consisting of:
a) an antibody comprising H-CDR1-3 that comprise the amino acid sequences of SEQ ID NOs: 5-7, 15-17, 25-27, 35-37, 45-47, 55-57, or 65-67, respectively;
b) an antibody whose VH is at least 90% identical in sequence to the amino acid sequence of SEQ ID NO: 3, 13, 23, 33, 43, 53, 63, or 73;
c) an antibody whose VH comprises the amino acid sequence of SEQ ID NO: 3, 13, 23, 33, 43, 53, 63, or 73;
d) an antibody whose HC comprises the amino acid sequences of SEQ ID NOs: 3 and 75, 13 and 75, 23 and 75, 33 and 75, 43 and 75, 53 and 75, 63 and 75, or 73 and 75;
e) an antibody comprising L-CDR1-3 that comprise the amino acid sequences of SEQ ID NOs: 8-10, 18-20, 28-30, 38-40, 48-50, 58-60, or 68-70, respectively;
f) an antibody whose VL is at least 90% identical in sequence to the amino acid sequence of SEQ ID NO: 4, 14, 24, 34, 44, 54, 64, or 74;
g) an antibody whose VL comprises the amino acid sequence of SEQ ID NO: 4, 14, 24, 34, 44, 54, 64, or 74;
h) an antibody whose LC comprises the amino acid sequences of SEQ ID NOs: 4 and 76, 14 and 76, 24 and 76, 34 and 76, 44 and 76, 54 and 76, 64 and 76, or 74 and 76;
i) an antibody whose H-CDR1-3 and L-CDR1-3 comprise the amino acid sequences of SEQ ID NOs: 5-10, 15-20, 25-30, 35-40, 45-50, 55-60, or 65-70, respectively;
j) an antibody comprising VH and VL that comprise amino acid sequences at least 90% identical to the amino acid sequences of SEQ ID NOs: 3 and 4, 13 and 14, 23 and 24, 33 and 34, 43 and 44, 53 and 54, 63 and 64, or 73 and 74, respectively;
k) an antibody comprising VH and VL that comprise the amino acid sequences of SEQ ID NOs: 3 and 4, 13 and 14, 23 and 24, 33 and 34, 43 and 44, 53 and 54, 63 and 64, or 73 and 74, respectively; and
l) an antibody comprising HC and LC that comprise the amino acid sequences of 3 and 75, and 4 and 76; 13 and 75, and 14 and 76; 23 and 75, and 24 and 76; 33 and 75, and 34 and 76; 43 and 75, and 44 and 76; 53 and 75, and 54 and 76; 63 and 75, and 64 and 76; or 73 and 75, and 74 and 76; respectively.

In some embodiments, an anti-FLT3 antibody composition described herein may inhibit tumor growth and/or induce tumor growth regression in vivo. In some embodiments, an anti-FLT3 antibody composition described herein may slow down or reverse metastasis in a cancer patient. In some embodiments, an anti-FLT3 antibody composition described herein may prolong survival of a cancer patient.

The present disclosure also provides a method for producing an anti-FLT3 antibody composition described herein, comprising providing a first anti-FLT3 antibody or antigen-binding portion and a second anti-FLT3 antibody or antigen-binding portion, and admixing the two antibodies or portions.

Bi-Specific Binding Molecules

The present disclosure also provides a bi-specific binding molecule having the binding specificity (e.g., comprising the antigen-binding portions, such as the six CDRs or the VH and VL) of an anti-FLT3 antibody described herein. In some embodiments, the bi-specific binding molecule additionally has the binding specificity of another, distinct anti-FLT3 antibody (e.g., another anti-FLT3 antibody described herein) or an antibody that targets a different protein, such as a cancer antigen or another cell surface molecule whose activity mediates a disease condition such as cancer. Such bi-specific binding molecules are known in the art, and examples of different types of bi-specific binding molecules are given elsewhere herein.

Nucleic Acid Molecules and Vectors

The present disclosure also provides nucleic acid molecules and sequences encoding anti-FLT3 antibodies or antigen-binding portions thereof described herein. In some embodiments, different nucleic acid molecules encode the heavy chain and light chain amino acid sequences of the anti-FLT3 antibody or antigen-binding portion. In other embodiments, the same nucleic acid molecule encodes the heavy chain and light chain amino acid sequences of the anti-FLT3 antibody or antigen-binding portion.

A reference to a nucleotide sequence encompasses its complement unless otherwise specified. Thus, a reference to a nucleic acid having a particular sequence should be understood to encompass its complementary strand, with its complementary sequence. The term "polynucleotide" as referred to herein means a polymeric form of nucleotides of at least 10 bases in length, either ribonucleotides or deoxynucleotides or a modified form of either type of nucleotide. The term includes single- and double-stranded forms.

In some embodiments, the present disclosure provides a nucleic acid molecule comprising a nucleotide sequence that encodes the heavy chain or an antigen-binding portion thereof, or a nucleotide sequence that encodes the light chain or an antigen-binding portion thereof, or both, of an anti-FLT3 antibody or antigen-binding portion thereof described herein.

The present disclosure also provides nucleotide sequences that are at least 70%, 75%, 80%, 85%, 90%, 95%, 97%, 98% or 99% identical (e.g., at least 90% identical) to one or more nucleotide sequences recited herein, e.g., to a nucleotide sequence selected from the group consisting of SEQ ID NOs: 1, 2, 11, 12, 21, 22, 31, 32, 41, 42, 51, 52, 61, 62, 71, and 72, or to a nucleotide sequence encoding an amino acid sequence selected from the group consisting of SEQ ID NOs: 3, 4, 13, 14, 23, 24, 33, 34, 43, 44, 53, 54, 63, 64, 73, and 74. The term "percent sequence identity" in the context of nucleic acid sequences refers to the residues in two sequences that are the same when aligned for maximum correspondence. The length of sequence identity comparison may be over a stretch of at least about nine nucleotides, usually at least about 18 nucleotides, more usually at least about 24 nucleotides, typically at least about 28 nucleotides, more typically at least about 32 nucleotides, and preferably at least about 36, 48 or more nucleotides. There are a number of different algorithms known in the art which can be used to measure nucleotide sequence identity. For instance, polynucleotide sequences can be compared using FASTA, Gap or Bestfit, which are programs in Wisconsin Package Version 10.0, Genetics Computer Group (GCG), Madison, Wisconsin. FASTA, which includes, e.g., the programs FASTA2 and FASTA3, provides alignments and percent sequence identity of the regions of the best overlap between the query and search sequences (see, e.g., Pearson, *Methods Enzymol.* (1990) 183:63-98; Pearson, *Methods Mol. Biol.* (2000) 132:185-219; Pearson, *Methods Enzymol.* (1996) 266:227-58; and Pearson, *J. Mol. Biol.* (1998) 276:71-84; incorporated herein by reference). Unless otherwise specified, default parameters for a particular program or algorithm are used. For instance, percent sequence identity between nucleic acid sequences can be determined using FASTA with its default parameters (a word size of 6 and the NOPAM factor for the scoring matrix) or using Gap with its default parameters as provided in GCG Version 6.1, incorporated herein by reference.

In some embodiments, the present disclosure provides a nucleic acid molecule comprising a nucleotide sequence selected from the group consisting of SEQ ID NOs: 1, 2, 11, 12, 21, 22, 31, 32, 41, 42, 51, 52, 61, 62, 71, and 72. In certain embodiments, the nucleic acid molecule comprises the nucleotide sequences of SEQ ID NOs: 1 and 2, 11 and 12, 21 and 22, 31 and 32, 41 and 42, 51 and 52, 61 and 62, or 71 and 72.

In any of the above embodiments, the nucleic acid molecules may be isolated. Nucleic acid molecules referred to herein as "isolated" or "purified" are nucleic acids which (1) have been separated away from the nucleic acids of the genomic DNA or cellular RNA of their source of origin; and/or (2) do not occur in nature.

In a further embodiment, the present disclosure provides a vector suitable for expressing one or both of the chains of an antibody or antigen-binding portion thereof as described herein. The term "vector", as used herein, means a nucleic acid molecule capable of transporting another nucleic acid to which it has been linked. In some embodiments, the vector is a plasmid, i.e., a circular double stranded piece of DNA into which additional DNA segments may be ligated. Moreover, certain vectors are capable of directing the expression of genes to which they are operatively linked. Such vectors are referred to herein as "recombinant expression vectors" (or simply, "expression vectors").

The present disclosure provides vectors comprising nucleic acid molecules that encode the heavy chain, the light chain, or both the heavy and light chains of an anti-FLT3 antibody as described herein or an antigen-binding portion thereof. In certain embodiments, a vector of the present disclosure comprises a nucleic acid molecule described herein. The present disclosure further provides vectors comprising nucleic acid molecules encoding fusion proteins, modified antibodies, antibody fragments, and probes thereof. The vector may further comprise an expression control sequence.

The term "expression control sequence" as used herein means polynucleotide sequences that are necessary to effect the expression and processing of coding sequences to which they are ligated. Expression control sequences include appropriate transcription initiation, termination, promoter and enhancer sequences; efficient RNA processing signals such as splicing and polyadenylation signals; sequences that stabilize cytoplasmic mRNA; sequences that enhance translation efficiency (i.e., Kozak consensus sequence); sequences that enhance protein stability; and when desired, sequences that enhance protein secretion. The nature of such control sequences differs depending upon the host organism; in prokaryotes, such control sequences generally include promoter, ribosomal binding site, and transcription termination sequence; in eukaryotes, generally, such control sequences include promoters and transcription termination sequence. The term "control sequences" is intended to include, at a minimum, all components whose presence is essential for expression and processing, and can also include additional components whose presence is advantageous, for example, leader sequences and fusion partner sequences.

In some embodiments, a nucleic acid molecule as described herein comprises a nucleotide sequence encoding a VH domain from an anti-FLT3 antibody or antigen-binding portion as described herein joined in-frame to a nucleotide sequence encoding a heavy chain constant region from any source. Similarly, a nucleic acid molecule as described herein can comprise a nucleotide sequence encoding a VL domain from an anti-FLT3 antibody or antigen-binding portion as described herein joined in-frame to a nucleotide sequence encoding a light chain constant region from any source.

In a further embodiment of the present disclosure, nucleic acid molecules encoding the VH and/or VL may be "converted" to full-length antibody genes. In some embodiments, nucleic acid molecules encoding the VH or VL domains are converted to full-length antibody genes by insertion into an expression vector already encoding heavy chain constant (CH) or light chain constant (CL) regions, respectively, such that the VH segment is operatively linked to the CH segment(s) within the vector, and/or the VL segment is operatively linked to the CL segment within the vector. In another embodiment, nucleic acid molecules encoding the VH and/or VL domains are converted into full-length antibody genes by linking, e.g., ligating, a nucleic acid molecule encoding a VH and/or VL domain to a nucleic acid molecule encoding a CH and/or CL region using standard molecular biological techniques. Nucleic acid molecules encoding the full-length heavy and/or light chains may then be expressed from a cell into which they have been introduced and the anti-FLT3 antibody isolated.

In some embodiments, the framework region(s) are mutated so that the resulting framework region(s) have the amino acid sequence of the corresponding germline gene. A mutation may be made in a framework region or constant region, e.g., to increase the half-life of the anti-FLT3 antibody. See, e.g., PCT Publication WO 00/09560. A mutation in a framework region or constant region also can be made to alter the immunogenicity of the antibody, and/or to provide a site for covalent or non-covalent binding to another molecule. According to the present disclosure, an antibody may have mutations in any one or more of the CDRs or framework regions of the variable domain or in the constant region.

Host Cells and Methods of Antibody and Antibody Composition Production

The present disclosure also provides methods for producing the antibody compositions and antibodies and antigen-binding portions thereof described herein. In some embodiments, the present disclosure relates to a method for producing an anti-FLT3 antibody or antigen-binding portion as described herein, comprising providing a host cell (e.g., a recombinant host cell) comprising a nucleotide sequence that encodes the heavy chain or an antigen-binding portion thereof, and a nucleotide sequence that encodes the light chain or an antigen-binding portion thereof, of an anti-FLT3 antibody or antigen-binding portion described herein; cultivating said host cell under conditions suitable for expression of the antibody or antigen-binding portion; and isolating the resulting antibody or antigen-binding portion. Antibodies or antigen-binding portions produced by such expression in such recombinant host cells are referred to herein as "recombinant" antibodies or antigen-binding portions. The present disclosure also provides progeny cells of such host cells, and antibodies or antigen-binding portions produced by same.

The term "recombinant host cell" (or simply "host cell"), as used herein, means a cell into which a recombinant expression vector has been introduced. By definition, a recombinant host cell does not occur in nature. The present disclosure provides host cells that may comprise, e.g., a vector as described herein. The present disclosure also provides host cells that comprise, e.g., a nucleotide sequence encoding the heavy chain or an antigen-binding portion thereof, a nucleotide sequence encoding the light chain or an antigen-binding portion thereof, or both, of an anti-FLT3 antibody or antigen-binding portion thereof described herein. It should be understood that "recombinant host cell" and "host cell" mean not only the particular subject cell but also the progeny of such a cell. Because certain modifications may occur in succeeding generations due to either mutation or environmental influences, such progeny may not, in fact, be identical to the parent cell, but are still included within the scope of the term "host cell" as used herein.

Nucleic acid molecules encoding anti-FLT3 antibodies and antigen-binding portions thereof and vectors comprising these nucleic acid molecules can be used for transfection of a suitable mammalian, plant, bacterial or yeast host cell. Transformation can be by any known method for introducing polynucleotides into a host cell. Methods for introduction of heterologous polynucleotides into mammalian cells are well known in the art and include dextran-mediated transfection, calcium phosphate precipitation, polybrene-mediated transfection, protoplast fusion, electroporation, encapsulation of the polynucleotide(s) in liposomes, and direct microinjection of the DNA into nuclei. In addition, nucleic acid molecules may be introduced into mammalian cells by viral vectors.

It is likely that antibodies expressed by different cell lines or in transgenic animals will have different glycosylation patterns from each other. However, all antibodies encoded by the nucleic acid molecules provided herein, or comprising the amino acid sequences provided herein are part of the present disclosure, regardless of the glycosylation state of the antibodies, and more generally, regardless of the presence or absence of post-translational modification(s).

Pharmaceutical Compositions

Another embodiment of the present disclosure is a pharmaceutical composition comprising as an active ingredient (or as the sole active ingredient) an anti-FLT3 antibody or antigen-binding portion thereof, antibody composition, or bi-specific binding molecule of the present disclosure. The pharmaceutical composition may additionally comprise a pharmaceutically acceptable excipient. In some embodiments, the pharmaceutical compositions are intended for amelioration, prevention, and/or treatment of cancer, e.g., a cancer described herein. In certain embodiments, the cancer is in a tissue such as skin, lung, intestine, colon, ovary, brain, prostate, kidney, soft tissues, the hematopoietic system, head and neck, liver, bone, bladder, breast, stomach, uterus, cervix, and pancreas.

Pharmaceutical compositions of the present disclosure will comprise one or more anti-FLT3 antibodies, antigen-binding portions, antibody compositions, or bi-specific binding molecules of the present disclosure, e.g., one or two anti-FLT3 antibodies, antigen-binding portions, or bi-specific binding molecules. In some embodiments, the composition comprises a single anti-FLT3 antibody of the present disclosure or an antigen-binding portion thereof. In another embodiment, the composition comprises two distinct anti-FLT3 antibodies of the present disclosure or antigen-binding portions thereof.

In some embodiments, the pharmaceutical composition may comprise at least one anti-FLT3 antibody or antigen-binding portion thereof of the present disclosure, e.g., one anti-FLT3 antibody or portion, and one or more additional antibodies that target one or more relevant cell surface receptors, e.g., one or more cancer-relevant receptors.

In some embodiments, the pharmaceutical composition may comprise at least one anti-FLT3 antibody or antigen-binding portion thereof of the present disclosure, e.g., one anti-FLT3 antibody or portion, and one or more additional agents selected from, e.g., an immunostimulatory agent, a vaccine, a chemotherapeutic agent, an anti-neoplastic agent, an anti-angiogenic agent, and a tyrosine kinase inhibitor.

Generally, the antibodies, antigen-binding portions, and bi-specific binding molecules of the present disclosure are suitable to be administered as a formulation in association with one or more pharmaceutically acceptable excipient(s), e.g., as described below.

The term "excipient" is used herein to describe any ingredient other than the compound(s) of the present disclosure. The choice of excipient(s) will to a large extent depend on factors such as the particular mode of administration, the effect of the excipient on solubility and stability, and the nature of the dosage form. As used herein, "pharmaceutically acceptable excipient" includes any and all solvents, dispersion media, coatings, antibacterial and antifungal agents, isotonic and absorption delaying agents, and the like that are physiologically compatible. Some examples of pharmaceutically acceptable excipients are water, saline, phosphate buffered saline, dextrose, glycerol, ethanol and the like, as well as combinations thereof. In many cases, it will be preferable to include isotonic agents, for example, sugars, polyalcohols such as mannitol, sorbitol, or sodium chloride in the composition. Additional examples of pharmaceutically acceptable substances are wetting agents or minor amounts of auxiliary substances such as wetting or emulsifying agents, preservatives or buffers, which enhance the shelf life or effectiveness of the antibody.

Pharmaceutical compositions of the present disclosure and methods for their preparation will be readily apparent to those skilled in the art. Such compositions and methods for their preparation may be found, for example, in Remington's Pharmaceutical Sciences, 19th Edition (Mack Publishing Company, 1995). Pharmaceutical compositions are preferably manufactured under GMP (good manufacturing practices) conditions.

A pharmaceutical composition of the present disclosure may be prepared, packaged, or sold in bulk, as a single unit dose, or as a plurality of single unit doses. As used herein, a "unit dose" is a discrete amount of the pharmaceutical composition comprising a predetermined amount of the active ingredient. The amount of the active ingredient is generally equal to the dosage of the active ingredient which would be administered to a subject or a convenient fraction of such a dosage such as, for example, one-half or one-third of such a dosage.

Formulations of a pharmaceutical composition suitable for parenteral administration typically comprise the active ingredient combined with a pharmaceutically acceptable carrier, such as sterile water or sterile isotonic saline. Such formulations may be prepared, packaged, or sold in a form suitable for bolus administration or for continuous administration. Injectable formulations may be prepared, packaged, or sold in unit dosage form, such as in ampoules or in multi-dose containers containing a preservative. Formulations for parenteral administration include, but are not limited to, suspensions, solutions, emulsions in oily or aqueous vehicles, pastes, and the like. Such formulations may further comprise one or more additional ingredients including, but not limited to, suspending, stabilizing, or dispersing agents. In some embodiments of a formulation for parenteral administration, the active ingredient is provided in dry (i.e., powder or granular) form for reconstitution with a suitable vehicle (e.g., sterile pyrogen-free water) prior to parenteral administration of the reconstituted composition. Parenteral formulations also include aqueous solutions which may contain excipients such as salts, carbohydrates and buffering agents (preferably to a pH of from 3 to 9), but, for some applications, they may be more suitably formulated as a sterile non-aqueous solution or as a dried form to be used in conjunction with a suitable vehicle such as sterile, pyrogen-free water. Exemplary parenteral administration forms include solutions or suspensions in sterile aqueous solutions, for example, aqueous propylene glycol or dextrose solutions. Such dosage forms can be suitably buffered, if desired. Other parentally-administrable formulations which are useful include those which comprise the active ingredient in microcrystalline form, or in a liposomal preparation.

Therapeutic Uses of Antibodies and Compositions of the Present Disclosure

In some embodiments, the anti-FLT3 antibodies and antigen-binding portions thereof, anti-FLT3 antibody compositions, and bi-specific binding molecules of the present disclosure are used to enhance or activate the immune system in a patient (e.g., a mammal such as a human) in need thereof, e.g., by stimulating FLT3 activity. In certain embodiments, the patient is immune-suppressed. In certain embodiments, a physician can boost the anti-cancer activity of a patient's own immune system by administering an anti-FLT3 antibody or antigen-binding portion thereof, composition, or bi-specific binding molecule as described herein. For example, a physician can boost anti-tumor activity in a patient by administering an anti-FLT3 antibody or antigen-binding portion, antibody composition, or bi-specific binding molecule of the present disclosure, alone or in combination with other therapeutic agents (sequentially or concurrently).

In certain embodiments, the antibodies or antigen-binding portions thereof, compositions, and bi-specific binding molecules of the present disclosure are for use in the treatment of cancer, e.g., an FLT3-positive cancer. The cancer may be in one or more tissues such as skin, lung, intestine, colon, ovary, brain, prostate, kidney, soft tissues, the hematopoietic system, head and neck, liver, bone, bladder, breast, stomach, uterus, cervix, and pancreas. In some embodiments, the antibodies or antigen-binding portions thereof, compositions, or bi-specific binding molecules of the present disclosure are for use in treating tumors with low immune cell infiltration (e.g., dendritic cell infiltration).

In some embodiments, cancers treated by the anti-FLT3 antibodies, antigen-binding portions, compositions, and bi-specific binding molecules of the present disclosure may include, e.g., melanoma (e.g., cutaneous, mucosal, or ocular melanoma; advanced or metastatic melanoma), skin basal cell cancer, glioblastoma, glioma, gliosarcoma, astrocytoma, meningioma, neuroblastoma, adrenocortical cancer, head and neck squamous cell cancer, oral cancer, salivary gland cancer, nasopharyngeal cancer, breast cancer, lung cancer (e.g., non-small cell lung cancer (NSCLC), small cell lung cancer, and squamous cell lung cancer), esophageal cancer, gastroesophageal junction cancer, gastric cancer, gastrointestinal cancer, primary peritoneal cancer, liver cancer, hepatocellular carcinoma, biliary tract cancer, colon cancer, rectal cancer, colorectal carcinoma, ovarian cancer, fallopian tube cancer, bladder cancer, upper urinary tract cancer, urothelial cancer, renal cell carcinoma, kidney cancer, genitourinary cancer, cervical cancer, prostate cancer, fibrosarcoma, liposarcoma, rhabdomyosarcoma, osteosarcoma, histiocytoma, pancreatic cancer, endometrial cancer, cancer of the appendix, advanced Merkel cell cancer, multiple myeloma, sarcomas, choriocarcinoma, erythroleukemia, acute lymphoblastic leukemia, acute monocytic leukemia, acute promyelocytic leukemia, acute myeloid leukemia, chronic myeloid leukemia, chronic lymphocytic leukemia, acute lymphoblastic leukemia, mast cell leukemia, small lymphocytic lymphoma, Burkitt's lymphoma, Hodgkin's lymphoma, non-Hodgkin's lymphoma, diffuse large B cell lymphoma, follicular lymphoma, monocytic lymphoma, HTLV-associated T cell leukemia/lymphoma, mesothelioma, and solid tumors. The cancer may be, e.g., at an early, intermediate, late, locally advanced, or metastatic stage, and may be relapsed or refractory to other therapeutics (e.g., other anti-FLT3 therapeutics, or checkpoint inhibitors) or there may be no standard therapy available.

In some embodiments, conditions treated by the anti-FLT3 antibodies, antigen-binding portions, compositions, and bi-specific binding molecules of the present disclosure may include, e.g., melanoma (e.g., cutaneous, mucosal, or ocular melanoma), glioma, glioblastoma multiforme, head and neck squamous cell cancer, breast cancer, non-small cell lung cancer, colorectal cancer, renal cell cancer, kidney cancer, lymphoma (e.g., B cell lymphoma or non-Hodgkin's lymphoma), leukemia (e.g., acute myeloid leukemia), multiple myeloma, plasma cell neoplasm, and myelodysplastic and/or myeloproliferative diseases.

In some embodiments, the antibodies or antigen-binding portions thereof, compositions, or bi-specific binding molecules of the present disclosure are for use in the treatment of an immune disorder.

In some embodiments, the antibody or antigen-binding portion, composition, or bi-specific binding molecule may be used to treat a patient who is, or is at risk of being, immunocompromised (e.g., due to chemotherapeutic or radiation therapy). In some embodiments, the antibody or antigen-binding portion, composition, or bi-specific binding molecule may be used to expand stem cells in a patient after stem cell transplantation.

In some embodiments, the antibody or antigen-binding portion, composition, or bi-specific binding molecule is for use in treating viral and/or parasitic infections, e.g., where the pathogens inhibit the host immune response. The pathogen may be, e.g., HIV, hepatitis (A, B, or C), human papilloma virus (HPV), lymphocytic choriomeningitis virus (LCMV), adenovirus, flavivirus, echovirus, rhinovirus, coxsackie virus, coronavirus, respiratory syncytial virus, mumps virus, rotavirus, measles virus, rubella virus, parvovirus, vaccinia virus, human T-cell lymphotrophic virus (HTLV), human cytomegalovirus (HCMV), dengue virus, molluscum virus, poliovirus, rabies virus, John Cunningham (JC) virus, arboviral encephalitis virus, simian immunodeficiency virus (SIV), influenza, herpes, Giardia, malaria, *Leishmania, Staphylococcus aureus, Mycobacterium tuberculosis,* or *Pseudomonas aeruginosa*.

"Treat," "treating," and "treatment" refer to a method of alleviating or abrogating a biological disorder and/or at least one of its attendant symptoms. As used herein, to "alleviate" a disease, disorder or condition means reducing the severity and/or occurrence frequency of the symptoms of the disease, disorder, or condition. Further, references herein to "treatment" include references to curative, palliative and prophylactic treatment.

"Therapeutically effective amount" refers to the amount of the therapeutic agent being administered that will relieve to some extent one or more of the symptoms of the disorder being treated. A therapeutically effective amount of an anti-cancer therapeutic may, for example, result in delayed tumor growth, tumor shrinkage, increased survival, elimination of cancer cells, slowed or decreased disease progression, reversal of metastasis, or other clinical endpoints desired by healthcare professionals.

The anti-FLT3 antibodies or antigen-binding portions thereof, antibody compositions, or bi-specific binding molecules described herein may be administered alone or in combination with one or more other drugs or antibodies (or as any combination thereof). The pharmaceutical compositions, methods and uses described herein thus also encompass embodiments of combinations (co-administration) with other active agents, as detailed below.

As used herein, the terms "co-administration," "co-administered" and "in combination with," referring to the anti-FLT3 antibodies and antigen-binding portions thereof, antibody compositions, and bi-specific binding molecules of the present disclosure with one or more other therapeutic agents, is intended to mean, and does refer to and include the following:
  a) simultaneous administration of such combination of antibody/antigen-binding portion/antibody composition/bi-specific binding molecule of the present disclosure and therapeutic agent(s) to a patient in need of treatment, when such components are formulated together into a single dosage form which releases said components at substantially the same time to said patient,
  b) substantially simultaneous administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at substantially the same time by said patient, whereupon said components are released at substantially the same time to said patient,
  c) sequential administration of such combination of antibody/antigen-binding portion/antibody composition/bi-specific binding molecule of the present disclosure and therapeutic agent(s) to a patient in need of treatment, when such components are formulated apart from each other into separate dosage forms which are taken at consecutive times by said patient with a significant time interval between each administration, whereupon said components are released at substantially different times to said patient; and
  d) sequential administration of such combination of antibody/antigen-binding portion/antibody composition/bi-specific binding molecule of the present disclosure and therapeutic agent(s) to a patient in need of treatment, when such components are formulated together into a single dosage form which releases said components in a controlled manner whereupon they are concurrently, consecutively, and/or overlappingly released at the same and/or different times to said patient, where each part may be administered by either the same or a different route.

The anti-FLT3 antibodies or antigen-binding portions thereof, antibody compositions, or bi-specific binding molecules of the present disclosure may be administered without additional therapeutic treatments, i.e., as a stand-alone therapy (monotherapy). Alternatively, treatment with the anti-FLT3 antibodies or antigen-binding portions thereof, antibody compositions, or bi-specific binding molecules of the present disclosure may include at least one additional therapeutic treatment (combination therapy), e.g., another immunostimulatory agent, an anti-cancer agent (e.g., a chemotherapeutic agent, an anti-neoplastic agent, an anti-angiogenic agent, or a tyrosine kinase inhibitor), or a vaccine (e.g., a tumor vaccine).

In some embodiments, the antibody or antigen-binding portion thereof, antibody composition, or bi-specific binding molecule may be co-administered or formulated with another medication/drug for the treatment of cancer. The additional therapeutic treatment may comprise, e.g., an immunostimulatory agent, a vaccine, a chemotherapeutic, anti-neoplastic, or anti-angiogenic agent, a tyrosine kinase inhibitor, and/or radiation therapy. In some embodiments, the additional therapeutic treatment may comprise a different anti-cancer antibody.

Pharmaceutical articles comprising an anti-FLT3 antibody or antigen-binding portion thereof, antibody composition, or bi-specific binding molecule described herein and at least one other agent (e.g., a chemotherapeutic, antineoplastic, or anti-angiogenic agent) may be used as a combination treatment for simultaneous, separate or successive administration in cancer therapy. The other agent may be any agent suitable for treatment of the particular cancer in question, for example, an agent selected from the group consisting of alkylating agents, e.g., platinum derivatives such as cisplatin, carboplatin and/or oxaliplatin; plant alkoids, e.g., paclitaxel, docetaxel and/or irinotecan; antitumor antibiotics, e.g., doxorubicin (adriamycin), daunorubicin, epirubicin, idarubicin mitoxantrone, dactinomycin, bleomycin, actinomycin, luteomycin, and/or mitomycin; topoisomerase inhibitors such as topotecan; antimetabolites, e.g., fluorouracil and/or other fluoropyrimidines; FOLFOX; osimertinib; cyclophosphamide; anthracycline; dacarbazine; gemcitabine; or any combination thereof. In some embodiments, the anti-FLT3 antibody or antigen-binding portion thereof, antibody composition, or bi-specific binding molecule described herein reestablishes responsiveness to the other agent.

An anti-FLT3 antibody or antigen-binding portion thereof, antibody composition, or bi-specific binding molecule of the present disclosure may also be used in combination with other anti-cancer therapies such as vaccines, cytokines, enzyme inhibitors, immunostimulatory compounds, and T cell therapies. In the case of a vaccine, it may be, e.g., a protein, peptide or DNA vaccine containing one or more antigens which are relevant for the cancer being treated, or a vaccine comprising dendritic cells along with an antigen. Suitable cytokines include, for example, IL-2, IFN-gamma and GM-CSF. An example of a type of enzyme inhibitor that has anti-cancer activity is an indoleamine-2,3-dioxygenase (IDO) inhibitor, for example, 1-methyl-D-tryptophan (1-D-MT). Also contemplated is adoptive T cell therapy, which refers to various immunotherapy techniques that involve expanding or engineering patients' own T cells to recognize and attack their tumors.

It is also contemplated that an anti-FLT3 antibody or antigen-binding portion thereof, antibody composition, or bi-specific binding molecule of the present disclosure may be used in adjunctive therapy in connection with tyrosine kinase inhibitors. These are synthetic, mainly quinazoline-derived, low molecular weight molecules that interact with the intracellular tyrosine kinase domain of receptors and inhibit ligand-induced receptor phosphorylation, e.g., by competing for the intracellular Mg-ATP binding site.

In some embodiments, the antibody or antigen-binding portion thereof, antibody composition, or bi-specific binding molecule may be used in combination with a medication/drug that mediates immune system activation, including, but not limited to, an agent that modulates the expression or activity of A2AR, A1AR, A2BR, A3AR, ADA, ALP, AXL, BTLA, B7-H3, B7-H4, CTLA-4, CD116, CD123, CD27, CD28, CD39, CD40, CD47, CD55, CD73, CD122, CD137, CD160, CGEN-15049, CHK1, CHK2, CTLA-3, CEACAM (e.g., CEACAM-1 and/or CEACAM-5), EGFR, FLT3, FLT3L, GAL9, GITR, HVEM, LAG-3, LILRB1, LY108, LAIR1, ICOS, IDO, IL2R, IL4R, KIR, LAIR1, MET, NKG2A, PAP, PD-1/PD-L1/PD-L2, OX40, STING, TIGIT, TIM-3, TGFR-beta, TLR1, TLR2, TLR3, TLR4, TLR5, TLR6, TLR7, TLR8, TLR9 and TLR10, TNFR2, VEGF, VEGFR, VISTA, LILRB2, CMTM6 and/or 2B4. In some embodiments, the agent enhances the activity, differentiation, proliferation, or mobilization of dendritic cells. In certain embodiments, the agent is a small molecule inhibitor. In certain embodiments, the agent is an antibody or an antigen-binding fragment thereof that binds to one of the above molecules. It is also contemplated that an anti-FLT3 antibody or antigen-binding portion thereof, antibody composition, or bi-specific binding molecule of the present disclosure may be used in combination with a cytokine (e.g., IL-1, IL-2, IL-12, IL-15 or IL-21), an EGFR inhibitor, a VEGF inhibitor, etc.

In particular embodiments, the antibody or antigen-binding portion thereof, antibody composition, or bi-specific binding molecule may be used in combination with an agent that modulates the expression or activity of FLT3L, CD40, AXL, a TLR, or PD-1.

The present disclosure also contemplates the use of sequences (e.g., the six CDR or VH and VL sequences) of an anti-FLT3 antibody or antigen-binding portion described herein in the preparation of a chimeric antigen receptor, which may be for use in CAR-T technology.

It is understood that the antibodies and antigen-binding portions thereof, antibody compositions, and bi-specific binding molecules of the present disclosure may be used in a method of treatment as described herein, may be for use in a treatment as described herein, and/or may be for use in the manufacture of a medicament for a treatment as described herein.

Dose and Route of Administration

The antibodies or antigen-binding portions thereof, antibody compositions, or bi-specific binding molecules of the present disclosure may be administered in an effective amount for treatment of the condition in question, i.e., at dosages and for periods of time necessary to achieve a desired result. A therapeutically effective amount may vary according to factors such as the particular condition being treated, the age, sex and weight of the patient, and whether the antibodies are being administered as a stand-alone treatment or in combination with one or more additional anti-cancer treatments.

Dosage regimens may be adjusted to provide the optimum desired response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form, as used herein, refers to physically discrete units suited as unitary dosages for the patients/subjects to be treated; each unit containing a predetermined quantity of active compound calculated to produce the desired therapeutic effect in association with the required pharmaceutical carrier. The specification for the dosage unit forms of the present disclosure are generally dictated by and directly dependent on (a) the unique characteristics of the therapeutic agent and the particular therapeutic or prophylactic effect to be achieved, and (b) the limitations inherent in the art of compounding such an active compound for the treatment of sensitivity in individuals.

Thus, the skilled artisan would appreciate, based upon the disclosure provided herein, that the dose and dosing regimen are adjusted in accordance with methods well-known in the therapeutic arts. That is, the maximum tolerable dose can be readily established, and the effective amount providing a detectable therapeutic benefit to a patient may also be determined, as can the temporal requirements for administering each agent to provide a detectable therapeutic benefit to the patient. Accordingly, while certain dose and administration regimens are exemplified herein, these examples in no way limit the dose and administration regimen that may be provided to a patient in practicing the present disclosure.

It is to be noted that dosage values may vary with the type and severity of the condition to be alleviated, and may include single or multiple doses. It is to be further understood that for any particular subject, specific dosage regimens should be adjusted over time according to the individual need and the professional judgment of the person administering or supervising the administration of the compositions, and that dosage ranges set forth herein are exemplary only and are not intended to limit the scope or practice of the embodied composition. Further, the dosage regimen with the compositions of the present disclosure may be based on a variety of factors, including the type of disease, the age, weight, sex, medical condition of the patient, the severity of the condition, the route of administration, and the particular antibody employed. Thus, the dosage regimen can vary widely, but can be determined routinely using standard methods. For example, doses may be adjusted based on pharmacokinetic or pharmacodynamic parameters, which may include clinical effects such as toxic effects and/or laboratory values. Thus, the present disclosure encompasses intra-patient dose-escalation as determined by the skilled artisan. Determining of appropriate dosages and regimens is well-known in the relevant art and would be understood to be encompassed by the skilled artisan once provided the teachings disclosed herein.

An effective amount for tumor therapy may be measured by its ability to stabilize disease progression and/or ameliorate symptoms in a patient, and preferably to reverse disease progression, e.g., by reducing tumor size. The ability of an antibody, antigen-binding portion, antibody composition, or bi-specific binding molecule of the present disclosure to inhibit cancer may be evaluated by in vitro assays, e.g., as described in the examples, as well as in suitable animal models that are predictive of the efficacy in human tumors. Suitable dosage regimens will be selected in order to provide an optimum therapeutic response in each particular situation, for example, administered as a single bolus or as a continuous infusion, and with possible adjustment of the dosage as indicated by the exigencies of each case.

The antibodies or antigen-binding portions thereof, antibody compositions, or bi-specific binding molecules of the present disclosure may be administered by any method for administering peptides, proteins or antibodies accepted in the art, and are typically suitable for parenteral administration. As used herein, "parenteral administration" includes any route of administration characterized by physical breaching of a tissue of a subject and administration through the breach in the tissue, thus generally resulting in the direct administration into the blood stream, into muscle, or into an internal organ. Parenteral administration thus includes, but is not limited to, administration by injection, by application through a surgical incision, by application through a tissue-penetrating non-surgical wound, and the like. In particular, parenteral administration is contemplated to include, but is not limited to, subcutaneous, intraperitoneal, intramuscular, intrasternal, intracisternal, intravenous, intraarterial, intrathecal, intraurethral, intracranial, intratumoral, and intrasynovial injection or infusions. Particular embodiments include the intravenous and the subcutaneous routes.

Diagnostic Uses and Compositions

The antibodies and antigen-binding portions of the present disclosure also are useful in diagnostic processes (e.g., in vitro or ex vivo). For example, the antibodies and antigen-binding portions can be used to detect and/or measure the level of FLT3 in a sample from a patient (e.g., a tissue sample, or a body fluid sample such as an inflammatory exudate, blood, serum, bowel fluid, saliva, or urine). Suitable detection and measurement methods include immunological methods such as flow cytometry, enzyme-linked immunosorbent assays (ELISA), chemiluminescence assays, radioimmunoassays, and immunohistology. The present disclosure further encompasses kits (e.g., diagnostic kits) comprising the antibodies and antigen-binding portions described herein.

Articles of Manufacture and Kits

The present disclosure also provides articles of manufacture, e.g., kits, comprising one or more containers (e.g., single-use or multi-use containers) containing a pharmaceutical composition of an anti-FLT3 antibody or antigen-binding portion thereof, composition, or bi-specific binding molecule described herein, optionally an additional biologically active molecule (e.g., another therapeutic agent), and instructions for use. The antibody or antigen-binding portion, composition, or bi-specific binding molecule, and optional additional biologically active molecule, can be packaged separately in suitable packing such as a vial or ampule made from non-reactive glass or plastic. In certain embodiments, the vial or ampule holds a concentrated stock (e.g., 2×, 5×, 10× or more) of the antibody or antigen-binding portion, composition, or bi-specific binding molecule and optionally the biologically active molecule. In certain embodiments, the articles of manufacture such as kits include a medical device for administering the antibody or antigen-binding portion, composition, or bi-specific binding molecule and/or biologically active molecule (e.g., a syringe and a needle); and/or an appropriate diluent (e.g., sterile water and normal saline). The present disclosure also includes methods for manufacturing said articles.

Unless otherwise defined herein, scientific and technical terms used in connection with the present disclosure shall have the meanings that are commonly understood by those of ordinary skill in the art. Exemplary methods and materials are described below, although methods and materials similar or equivalent to those described herein can also be used in the practice or testing of the present disclosure. In case of conflict, the present specification, including definitions, will control.

Generally, nomenclature used in connection with, and techniques of, cell and tissue culture, molecular biology, immunology, microbiology, genetics, analytical chemistry, synthetic organic chemistry, medicinal and pharmaceutical chemistry, and protein and nucleic acid chemistry and hybridization described herein are those well-known and commonly used in the art. Enzymatic reactions and purification techniques are performed according to manufacturer's specifications, as commonly accomplished in the art or as described herein.

Further, unless otherwise required by context, singular terms shall include pluralities and plural terms shall include the singular. Throughout this specification and embodiments, the words "have" and "comprise," or variations such as "has," "having," "comprises," or "comprising," will be understood to imply the inclusion of a stated integer or group of integers but not the exclusion of any other integer or group of integers.

All publications and other references mentioned herein are incorporated by reference in their entirety. Although a number of documents are cited herein, this citation does not constitute an admission that any of these documents forms part of the common general knowledge in the art.

In order that the present disclosure may be better understood, the following examples are set forth. These examples are for purposes of illustration only and are not to be construed as limiting the scope of the present disclosure in any manner.

EXAMPLES

Example 1. Cloning of Anti-FLT3 Antibodies from Rat B Cells

Materials and Methods

Antibodies against human FLT3 were isolated from an antibody repertoire derived from OmniRat® rats (Osborn et al., *J Immunol.* 190(4):1481-90 (2013)), a transgenic rat strain from Ligand Pharmaceuticals Inc. that produces antibodies with fully human idiotypes. Cloning of rat-derived antibody genes from single-cell sorted antibody-secreting B cells (ASC) was performed by means of Symplex™ antibody discovery technology (Meijer et al., *J Mol Biol* 358 (3):764-72 (2006)).

Antibody repertoire constructs encoding fully human immunoglobulins in IgG$_1$-LALA format (see below) were transfected into HEK293 cells. Cell supernatants were screened for binding to FLT3 expressed on the surface of CHO cells using flow cytometry in a high-throughput format. FLT3 reactive clones were analyzed by DNA sequencing and antibody-encoding DNA sequences were extracted. Selected antibody clones were expressed and tested functionally as described below.

Missense mutations in the amino termini of heavy and light chains that were introduced by the use of degenerate primers in the Symplex™ cloning of the antibody-encoding cDNA fragments were corrected back to germline sequence. Table 1 shows the heavy and light chain variable domain nucleotide sequences of the germlined antibodies designated 17566, 17526, 17667, 17679, 17494, 17543, and 17497. The correction process involves amino terminal sequence correction to germline as well as codon usage optimization. The targets for matching to human germline sequences were identified by blast homology searches for the heavy chain and the light chain variable regions. Table 1 also includes the heavy and light chain variable domain sequences for a version of antibody 17667 that did not undergo germline correction (17667.0).

Protein sequences of the variable domains, the constant regions and the complementarity determining regions (CDRs) of antibodies 17566, 17526, 17667, 17667-0, 17679, 17494, 17543, and 17497 are shown in Table 2, Table 3, and Table 4, respectively.

Results

Table 1 shows nucleotide sequences encoding the variable domains of antibodies 17566, 17526, 17667, 17667-0, 17679, 17494, 17543, and 17497.

TABLE 1

Variable domain nucleotide sequences of antibodies
17566, 17526, 17667, 17667-0, 17679, 17494, 17543, and 17497

| Ab | Sequence (5' to 3') | SEQ |
|---|---|---|
| 17566 VH | CAAGTGACACTGAAGGAGTCCGGCCCAGTGCTGGTGAAGCCCACCGAGACAC<br>TGACCCTGACATGCACCGTGTCTGGCTTCTCCTTTAACAATGCCAGGATGGG<br>AGTGAACTGGATCAGGCAGCCACCTGGCAAGGCCCTGGAGTGGCTGGCTCAC<br>ATCTTCAGCAATGACGAGAAGTCCTACAGCACATCTCTGAAGAGCAGGCTGA<br>CCATCTCTAAGGATATCTCCAAGAGCCAGGTGGTGCTGACAATGACCAACAT<br>GGACCCCGTGGATACAGCCACCTACTATTGTGCTAGAATCGTGGGATACGGA<br>TCTGGATGGAGGCTGCTGGGCGACTATTGGGGACAGGGCACACTGGTGACCG<br>TCTCGAGT | 1 |
| 17526 VH | CAAGTGACACTGAAGGAGTCTGGCCCAGTGCTGGTGAAGCCCACCGAGACAC<br>TGACCCTGACATGCACCATCTCTGGCTTCTCCCTGGGCAACGCCAGGATGGG<br>CGTGTCCTGGATCAGGCAGCCACCTGGCAAGGCCCTGGAGTGGCTGGCTCAC<br>ATCTTTAGCAATGACGAGAAGTCCTACAGCACCTCTCTGAAGAGCAGACTGA<br>CAATCTCTAAGGATACCTCCAAGAGCCAGGTGGTGCTGACAATGACCAACAT<br>GGACCCTGTGGATACAGCCACCTACTATTGTGCTCGCATCGTGGGCTACGTG<br>GACTGGCTGCTGCCATTCGATTATTGGGGCAGGGCACACTGGTGACCGTCT<br>CGAGT | 11 |
| 17667 VH | CAAGTGACACTGAAGGAGTCTGGCCCAGTGCTGGTGAAGCCCACCGAGACAC<br>TGACCCTGACATGCACCGTGTCCGGCTTCTCCCTGAGCAACGCCAGGATGGG<br>CGTGAGCTGGATCAGGCAGCCACCTGGCAAGGCCCTGGAGTGGCTGGCTCAC<br>ATCTTTTCCAATGACGAGAGATCTTACTCCCCCAGCCTGAAGAGCCGCCTGA<br>CAATCTCTAAGGGCACCTCTAAGTCCCAGGTGGTGCTGACAATGACCAACAT<br>GGACCCTGTGGATACAGCCACCTACTATTGTGCTAGGATCGTGGGCTACGTG<br>GACTGGCTGCTGCCATTCGATTATTGGGGCCAGGGCACACTGGTGACCGTCT<br>CGAGT | 21 |
| 17679 VH | CAAGTGCAGCTGCAGGAGTCCGGACCAGGACTGGTGAAGCCTTCTCAGACCC<br>TGTCCCTGACCTGCACAGTGAGCGGAGGATCTATCTCCAGCGGAGGATACTA<br>TTGGTCCTGGATCAGACAGCACCCAGGCAAGGGCCTGGAGTGGATCGGCTAC<br>ATCTACTATAGCGGCAGGACAAACTATAATCCCTCCCTGAAGAGCCGGGTGA<br>CCATCAGCGAGGACACATCTAAGAACCAGTTCTCTCTGAAGGTGTCTTCCGT<br>GACCGCCGCTGATACAGCCGTGTACTATTGTGCTCGCGACCAGGATGGCTCC<br>GGCTGGTACTTTGACTATTGGGGCCAGGGCGCCCTGGTGACCGTCTCGAGT | 31 |
| 17494 VH | CAAGTGCAGCTGCAGGAGAGCGGACCAGGACTGGTGAAGCCTAGCCAGACCC<br>TGTCTCTGACCTGCACTGTGTCCGGAGGAAGCATCTCCAGCGGAGGATACTA<br>TTGGTCTTGGATCAGGCAGCACCCAGGCAAGGGCCTGGAGTGGATCGGCTAC<br>ATCTACTATAGCGGCTCATACATACTATAACCCCTCTCTGAAGTCCCGGGTGA<br>CCATCTCCGTGGACACAAGCAAGAATCAGTTCTCTCTGAAGCTGTCTTCCGT<br>GACCGCCGCTGATACAGCCGTGTACTATTGTGCTAGGGACCTGGATGGCTCC<br>GGCTGGTACTTTGACTATTGGGGCCAGGGCACCCTGGTGACAGTCTCGAGT | 41 |
| 17543 VH | CAAGTGACCCTGAAGGAGTCCGGCCCAGTGCTGGTGAAGCCCACCGAGACAC<br>TGACCCTGACATGCACCGTGTCTGGCTTCTCCCTGATCAACGCCAGAATGGG<br>AGTGACATGGATCAGGCAGCCACCTGGCAAGGCCCTGGAGTGGCTGGCTCAC<br>ATCTTTAGCAATGACGAGAAGTCCTACAGCACCTCTCTGAAGAGCAGGCTGA<br>CAATCTCTAAGGATACCTCCAAGAGCCAGGTGGTGCTGACAATGACCAACAT<br>GGACCCTGTGGATACAGCCACCTACTATTGTGCTAGGATCCCAGGCTATTCT<br>CGGGGCTGGGACTACTATTACTATGGCATGGACGTGTGGGGCCAGGGCACAA<br>TGGTGACCGTCTCGAGT | 51 |
| 17497 VH | CAAGTGCAGCTGCAGGAGTCTGGACCAGGACTGGTGAAGCCATCTGGCACCC<br>TGTCCCTGACATGCGCCGTGAGCGGAGGATCTATCTCCAGCACCAACTGGTG<br>GTCCTGGGTGAGACAGCCACCTGGCAAGGGACTGGAGTGGATCGGCGAGATC<br>AGCCACAGGGGCTCTACCAACTACAATCCTTCCCTGAAGAGCCGGGTGACAA<br>TCTCCGTGGACAAGAGCAAGAATCAGTTCTCCCTGAAGCTGTCTTCCGTGAC<br>CGCCGCTGACACAGCCGTGTACTATTGTGCTCGCGATCCAGAGATGACCCTG<br>TACTATTACTATGGCATGGACGTGTGGGGCCAGGGCACCACAGTGACAGTCT<br>CGAGT | 61 |
| 17667-0 VH | CAGGTGCAGCTACAGGAGTCTGGTCCTGTGCTGGTGAAACCCACAGAGACCC<br>TCACGCTGACCTGCACCGTCTCTGGGTTCTCACTCAGCAATGCTAGAATGGG<br>TGTTAGCTGGATCCGTCAGCCCCCAGGGAAGGCCCTGGAGTGGCTTGCACAC<br>ATTTTTTTCAAATGACGAAAGATCCTACAGTCCATCTCTGAAGAGCAGGCTCA<br>CCATCTCCAAGGGCACCTCCAAAAGCCAGGTGGTCCTTACCATGACCAACAT<br>GGACCCTGTGGACACAGCCACATATTACTGTGCACGGATAGTAGGATATGTT<br>GACTGGTTATACCCTTTGACTACTGGGGCCAGGGAACCCTGGTCACGGTCT<br>CGAGT | 71 |
| 17566 VL | GCCATCCAGATGACCCAGAGCCCTTCCAGCCTGTCCGCCTCCGTGGGCGACA<br>GGGTGACCATCACATGCCGGGCCTCTCAGGGCATCACAAACGATCTGGGCTG<br>GTACCAGCAGAAGCCCGGCAAGGCTCCTAAGCTGCTGATCTATGCCGCTTCT<br>TCCCTGCAATCTGGCGTGCCATCCAGGTTCTCTGGATCCGGAAGCGGAACCG | 2 |

TABLE 1-continued

Variable domain nucleotide sequences of antibodies 17566, 17526, 17667, 17667-0, 17679, 17494, 17543, and 17497

| Ab | Sequence (5' to 3') | SEQ |
|---|---|---|
| | ACTTTACCCTGACAATCAGCTCTCTGCAACCAGAGGACTTCGCCACATACTA TTGTCTGCAAGATTACAATTATCCCTGGACCTTTGGCCAGGGCACAAAGGTG GAGATCAAG | |
| 17526 VL | GAGATCGTGATGACCCAGTCTCCAGCCACACTGAGCGTGTCTCCAGGAGAGA GGGCCACCCTGTCCTGCAGAGCTTCCCAGAGCGTGTCCAGCAACCTGGCTTG GTACCAGCAGAAGCCAGGACAGGCTCCTAGGCTGCTGATCTATGGCGCCAGC AccAGAGcTAcAGGAATcccTGcTcGcTTcTcTGGATccGGAAGcGGcAcAG AGTTTACCCTGACAATCTCTTCCCTGCAATCTGAGGACTTCGCCGTGTACTA TTGTCAGCAATACAATCACTGGCCAATGTATACCTTTGGCCAGGGCACAAAG CTGGAGATCAAG | 12 |
| 17667 VL | GAGATCGTGATGACCCAGTCTCCAGCCACACTGAGCGTGTCTCCAGGAGAGA GGGCCACCCTGTCCTGCAGAGCTTCCCAGAGCGTGTCCAGCAACCTGGCTTG GTACCAGCAGAAGCCAGGACAGGCTCCTAGGCTGCTGATCTATGGCGCCAGC AccAGAGcTAcAGGAATcccTGcTcGcTTcTcTGGATccGGAAGcGGcAcAG AGTTTACCCTGACAATCTCTTCCCTGCAATCTGAGGACTTCGCCGTGTACTA TTGTCAGCAGTACAACAATTGGCCAATGTATACCTTTGGCCAGGGCACAAAG CTGGAGATCAAG | 22 |
| 17679 VL | GAGATCGTGCTGACCCAGTCCCCAGCCACACTGTCTCTGTCCCCCGGAGAGA GGGCCACCCTGAGCTGCAGGGCCTCCCAGTCCGTGTCCTCCTACCTGGCCTG GTATCAGCAGAAGCCCGGCCAGGCTCCTAGGCTGCTGATCTACGACGCCAGC AACAGAGCTACCGGAATCCCTGCTCGCTTCTCCGGAAGCGGATCTGGCACAG ACTTTACCCTGACAATCAGGTCTCTGGAGCCAGAGGATTTCGCCGTGTACTA TTGTCAGCAGAGATCCAATTGGTGGACCTTTGGCCAGGGCACAAAGGTGGAG ATCAAG | 32 |
| 17494 VL | GAGATCGTGCTGACCCAGTCTCCTGCCACACTGAGCCTGTCTCCAGGAGAGA GGGccAcccTGTccTGcAGAGcTTcccAGAGcGTGTccAGcTAccTGGccTG GTATCAGCAAAAGCCAGGCCAGGCTCCCAGGCTGCTGATCTACGACGCCAGC AACAGAGCTACCGGAATCCCAGCTCGCTTCTCTGGATCCGGAAGCGGCACAG ACTTTACCCTGACAATCTCTTCCCTGGAGCCTGAGGATTTCGCCGTGTACTA TTGTCAGCAGAGATCTAATTGGCCCCCTCTGACCTTTGGCGGCGGCACAAAG GTGGAGATCAAG | 42 |
| 17543 VL | GACATCCAGATGACACAGTCCCCTTCCAGCCTGAGCGCCTCTGTGGGCGACA GGGTGACCATCACATGCCGGGCCTCCCAGGGCATCAGAAACGATCTGGGCTG GTACCAGCAGAAGCCCGGCAAGGCCCCTAAGCGCCTGATCTATGCTGCTTCC AcccTGcAGAGcGGAGTGccATcTAGGTTcTccGGcAGcGGcTcTGGcAcAG AGTTTACCCTGACAATCTCTTCCCTGCAGCCAGAGGATTTCGCTACCTACTA TTGTCTGCAGCACAATTCTTACCCCTGGACCTTTGGCCAGGGCACAAAGGTG GAGATCAAG | 52 |
| 17497 VL | GACATCCAGATGACCCAGAGCCCTTCCAGCCTGTCCGCCAGCGTGGGCGACA GAGTGACCATCACATGCAGGGCTTCTCGGGGCATCAGAAACGATCTGGGCTG GTACCAGCAGAAGCCCGGCAAGGCCCCTAAGCGCCTGATCTATGCCGCTTCT TCCCTGCAATCTGGCGTGCCATCCAGATTCTCTGGATCCGGAAGCGGAACCG AGTTTACCCTGACAATCAGCTCTCTGCAGCCAGAGGATTTCGCTACATACTA TTGTCTGCAGCACAATTCCTACCCCCTGACCTTTGGCGGCGGCACAAAGGTG GAGATCAAG | 62 |
| 17667-0 VL | GAAACGACACTCACGCAGTCTCCAGCCACCCTGTCTGTGTCTCCAGGGGAAA GAGCCACCCTCTCCTGCAGGGCCAGTCAGAGCGTTAGCAGCAACTTAGCCTG GTACCAGCAGAAACCTGGCCAGGCTCCCAGGCTCCTCATCTATGGTGCATCC ACCAGGGCCACTGGTATCCCAGCCAGGTTCAGTGGCAGTGGGTCTGGGACAG AGTTCACTCTCACCATCAGCAGCCTGCAGTCTGAAGATTTTGCAGTTTATTA CTGTCAGCAGTATAATAACTGGCCCATGTACACTTTTGGCCAGGGGACCAAG CTGGAGATTAAG | 72 |

SEQ: SEQ ID NO.

Table 2 shows the deduced amino acid sequences of antibodies 17566, 17526, 17667, 17667-0, 17679, 17494, 17543, and 17497. CDRs are in bold/underlined.

TABLE 2

Variable domain amino acid sequences of antibodies 17566, 17526, 17667, 17679, 17494, 17543, and 17497

| Ab | Sequence (N-terminal to C-terminal) | SEQ |
|---|---|---|
| 17566 VH | QVTLKESGPVLVKPTETLTLTCTVSGFSFNNARMGVNWIRQPPGKALEWLAHIFSNDEKSYSTSLKSRLTISKDISKSQVVLTMTNMDPVDTATYYCARIVGYGSGWRLLGDYWGQGTLVTVSS | 3 |
| 17526 VH | QVTLKESGPVLVKPTETLTLTCTISGFSLGNARMGVSWIRQPPGKALEWLAHIFSNDEKSYSTSLKSRLTISKDTSKSQVVLTMTNMDPVDTATYYCARIVGYVDWLLPFDYWGQGTLVTVSS | 13 |
| 17667 VH | QVTLKESGPVLVKPTETLTLTCTVSGFSLSNARMGVSWIRQPPGKALEWLAHIFSNDERSYSPSLKSRLTISKGTSKSQVVLTMTNMDPVDTATYYCARIVGYVDWLLPFDYWGQGTLVTVSS | 23 |
| 17679 VH | QVQLQESGPGLVKPSQTLSLTCTVSGGSISSGGYYWSWIRQHPGKGLEWIGYIYYSGRTNYNPSLKSRVTISEDTSKNQFSLKVSSVTAADTAVYYCARDQDGSGWYFDYWGQGALVTVSS | 33 |
| 17494 VH | QVQLQESGPGLVKPSQTLSLTCTVSGGSISSGGYYWSWIRQHPGKGLEWIGYIYYSGSTYYNPSLKSRVTISVDTSKNQFSLKLSSVTAADTAVYYCARDLDGSGWYFDYWGQGTLVTVSS | 43 |
| 17543 VH | QVTLKESGPVLVKPTETLTLTCTVSGFSLINARMGVTWIRQPPGKALEWLAHIFSNDEKSYSTSLKSRLTISKDTSKSQVVLTMTNMDPVDTATYYCARIPGYSRGWDYYYYGMDVWGQGTMVTVSS | 53 |
| 17497 VH | QVQLQESGPGLVKPSGTLSLTCAVSGGSISSTNWWSWVRQPPGKGLEWIGEISHRGSTNYNPSLKSRVTISVDKSKNQFSLKLSSVTAADTAVYYCARDPEMTLYYYYGMDVWGQGTTVTVSS | 63 |
| 17667-0 VH | QVQLQESGPVLVKPTETLTLTCTVSGFSLSNARMGVSWIRQPPGKALEWLAHIFSNDERSYSPSLKSRLTISKGTSKSQVVLTMTNMDPVDTATYYCARIVGYVDWLLPFDYWGQGTLVTVSS | 73 |
| 17566 VL | AIQMTQSPSSLSASVGDRVTITCRASQGITNDLGWYQQKPGKAPKLLIYAASSLQSGVPSRFSGSGSGTDFTLTISSLQPEDFATYYCLQDYNYPWTFGQGTKVEIK | 4 |
| 17526 VL | EIVMTQSPATLSVSPGERATLSCRASQSVSSNLAWYQQKPGQAPRLLIYGASTRATGIPARFSGSGSGTEFTLTISSLQSEDFAVYYCQQYNHWPMYTFGQGTKLEIK | 14 |
| 17667 VL | EIVMTQSPATLSVSPGERATLSCRASQSVSSNLAWYQQKPGQAPRLLIYGASTRATGIPARFSGSGSGTEFTLTISSLQSEDFAVYYCQQYNNWPMYTFGQGTKLEIK | 24 |
| 17679 VL | EIVLTQSPATLSLSPGERATLSCRASQSVSSYLAWYQQKPGQAPRLLIYDASNRATGIPARFSGSGSGTDFTLTIRSLEpEDFAVYYCQQRSNWWTFGQGTKVEIK | 34 |
| 17494 VL | EIVLTQSPATLSLSPGERATLSCRASQSVSSYLAWYQQKPGQAPRLLIYDASNRATGIPARFSGSGSGTDFTLTISSLEPEDFAVYYCQQRSNWPPLTFGGGTKVEIK | 44 |
| 17543 VL | DIQMTQSPSSLSASVGDRVTITCRASQGIRNDLGWYQQKPGKAPKRLIYAASTLQSGVPSRFSGSGSGTEFTLTISSLQPEDFATYYCLQHNSYPWTFGQGTKVEIK | 54 |
| 17497 VL | DIQMTQSPSSLSASVGDRVTITCRASRGIRNDLGWYQQKPGKAPKRLIYAASSLQSGVPSRFSGSGSGTEFTLTISSLQPEDFATYYCLQHNSYPLTFGGGTKVEIK | 64 |
| 17667-0 VL | VLETTLTQSPATLSVSPGERATLSCRASQSVSSNLAWYQQKPGQAPRLLIYGASTRATGIPARFSGSGSGTEFTLTISSLQSEDFAVYYCQQYNNWPMYTFGQGTKLEIK | 74 |

SEQ: SEQ ID NO.

Table 3 shows heavy and light chain constant region amino acid sequences (CH and CL, respectively). "IgG$_1$-LALA" refers to the presence of "LALA" mutations in the heavy chain (L234A/L235A, numbered according to the IMGT® numbering scheme) that are known to reduce effector function of the Fc region of IgG$_1$ antibodies (Hezareh et al., *J Virol.* (2001) 75(24):12161-8; Hessell et al., *Nature* (2007) 449(7158):101-4).

TABLE 3

Constant region amino acid sequences of antibodies 17566, 17526, 17667, 17667-0, 17679, 17494, 17543, and 17497

| Fragment | Sequence (N-terminal to C-terminal) | SEQ |
|---|---|---|
| IgG$_1$-LALA CH added to the VH | ASTKGPSVFPLAPSSKSTSGGTAALGCLVKDYFPEPVTVSWNSGALTS GVHTFPAVLQSSGLYSLSSVVTVPSSSLGTQTYICNVNHKPSNTKVDK RVEPKSCDKTHTCPPCPAPEAAGGPSVFLFPPKPKDTLMISRTPEVTC VVVDVSHEDPEVKFNWYVDGVEVHNAKTKPREEQYNSTYRVVSVLTVL HQDWLNGKEYKCKVSNKALPAPIEKTISKAKGQPREPQVYTLPPSREE MTKNQVSLTCLVKGFYPSDIAVEWESNGQPENNYKTTPPVLDSDGSFF LYSKLTVDKSRWQQGNVFSCSVMHEALHNHYTQKSLSLSPGK | 75 |
| Kappa CL added to the VL | RTVAAPSVFIFPPSDEQLKSGTASVVCLLNNFYPREAKVQWKVDNALQ SGNSQESVTEQDSKDSTYSLSSTLTLSKADYEKHKVYACEVTHQGLSS PVTKSFNRGEC | 76 |

SEQ: SEQ ID NO.

Table 4 shows heavy and light chain CDR amino acid sequences of antibodies 17566, 17526, 17667, 17667-0, 17679, 17494, 17543, and 17497, wherein the CDRs are defined according to the IMGT® system.

TABLE 4

CDR amino acid sequences of antibodies 17566, 17526, 17667, 17667-0, 17679, 17494, 17543, and 17497

| | Sequence (N-terminal to C-terminal) | | | | | |
|---|---|---|---|---|---|---|
| Ab | H-CDR1 | H-CDR2 | H-CDR3 | L-CDR1 | L-CDR2 | L-CDR3 |
| 17566 | GFSFNNARMG SEQ: 5 | IFSNDEK SEQ: 6 | CARIVGYGSGWRLLGDYW SEQ: 7 | QGITND SEQ: 8 | AAS SEQ: 9 | CLQDYNYPWTF SEQ: 10 |
| 17526 | GFSLGNARMG SEQ: 15 | IFSNDEK SEQ: 16 | CARIVGYVDWLLPFDYW SEQ: 17 | QSVSSN SEQ: 18 | GAS SEQ: 19 | CQQYNHWPMYTF SEQ: 20 |
| 17667, 17667-0 | GFSLSNARMG SEQ: 25 | IFSNDER SEQ: 26 | CARIVGYVDWLLPFDYW SEQ: 27 | QSVSSN SEQ: 28 | GAS SEQ: 29 | CQQYNNWPMYTF SEQ: 30 |
| 17679 | GGSISSGGYY SEQ: 35 | IYYSGRT SEQ: 36 | CARDQDGSGWYFDYW SEQ: 37 | QSVSSY SEQ: 38 | DAS SEQ: 39 | CQQRSNWWTF SEQ: 40 |
| 17494 | GGSISSGGYY SEQ: 45 | IYYSGST SEQ: 46 | CARDLDGSGWYFDYW SEQ: 47 | QSVSSY SEQ: 48 | DAS SEQ: 49 | CQQRSNWPPLTF SEQ: 50 |
| 17543 | GFSLINARMG SEQ: 55 | IFSNDEK SEQ: 56 | CARIPGYSRGWDYYYYGMD VW SEQ: 57 | QGIRND SEQ: 58 | AAS SEQ: 59 | CLQHNSYPWTF SEQ: 60 |
| 17497 | GGSISSTNW SEQ: 65 | ISHRGST SEQ: 66 | CARDPEMTLYYYYGMDVW SEQ: 67 | RGIRND SEQ: 68 | AAS SEQ: 69 | CLQHNSYPLTF SEQ: 70 |

SEQ: SEQ ID NO:

Table 5 shows SEQ ID NO information for antibodies 17566, 17526, 17667, 17667-0, 17679, 17494, 17543, and 174978. Unless otherwise stated, the sequences are amino acid sequences.

TABLE 5

SEQ ID NOs for antibodies 17566, 17526, 17667, 17667-0, 17679, 17494, 17543, and 17497

| Name | VH nt | VL nt | VH aa | VL aa | H-CDR1 | H-CDR2 | H-CDR3 | L-CDR1 | L-CDR2 | L-CDR3 |
|---|---|---|---|---|---|---|---|---|---|---|
| 17566 | 1 | 2 | 3 | 4 | 5 | 6 | 7 | 8 | 9 | 10 |
| 17526 | 11 | 12 | 13 | 14 | 15 | 16 | 17 | 18 | 19 | 20 |
| 17667 | 21 | 22 | 23 | 24 | 25 | 26 | 27 | 28 | 29 | 30 |
| 17679 | 31 | 32 | 33 | 34 | 35 | 36 | 37 | 38 | 39 | 40 |
| 17494 | 41 | 42 | 43 | 44 | 45 | 46 | 47 | 48 | 49 | 50 |
| 17543 | 51 | 52 | 53 | 54 | 55 | 56 | 57 | 58 | 59 | 60 |
| 17497 | 61 | 62 | 63 | 64 | 65 | 66 | 67 | 68 | 69 | 70 |
| 17667-0 | 71 | 72 | 73 | 74 | 25 | 26 | 27 | 28 | 29 | 30 | nt: nucleotide
aa: amino acid

Example 2. In Vitro Functional Screening of Anti-FLT3 Antibodies in EOL-1 Proliferation Assay This example describes in vitro functional evaluation of a panel of anti-FLT3 monoclonal antibodies with the purpose of identifying lead candidates with agonistic activity. The antibodies were evaluated for their ability to stimulate proliferation of the FLT3 expressing cancer cell line EOL-1.

Materials and Methods

A panel of anti-FLT3 antibodies were evaluated in vitro for their ability to induce proliferation of the FLT3 expressing cancer cell line EOL-1. The EOL-1 cells were seeded in RPMI 1640 Glutamax media supplemented with 0.5% FBS and 1% P/S and incubated for 5 days with the indicated antibodies at a final concentration of 25 µg/mL. Cell proliferation was quantified using WST-1 cell proliferation reagent (Roche) as per manufacturer's instructions.

Results

The proliferation of EOL-1 cells after treatment with anti-FLT3 antibodies is shown in FIG. 1. The ability to induce proliferation of EOL-1 cells varied greatly between the tested antibodies. Some antibodies showed no effect in this assay, while other antibodies had a stimulatory capacity as shown by their ability to induce proliferation of the EOL-1 cells.

Example 3. Cloning of Anti-FLT3 Reference Antibody Analogues

Materials and Methods

The amino acid sequences encoding the heavy and light chain variable domains of the antibody analogue in Table 6 were obtained from the listed patent application. The protein sequences were reverse translated to DNA sequences with human codon usage. The corresponding DNA sequences were gene synthesized and cloned into expression vectors containing human heavy or light chain constant regions, resulting in expression of full-length antibody chains. The human antibody isotype selected for expression is listed in the antibody format column. CHO cells were transfected with the resulting expression plasmids using a standard protein expression system. The corresponding antibody supernatants were purified using standard protein A purification column chromatography.

TABLE 6

Listing of gene-synthesized antibody analogues and the corresponding antibody format

| Antibody | Antibody format | Source |
|---|---|---|
| IMC-EB10 analogue | IgG$_1$/kappa | U.S. Patent Application 2011/0091470 A1 (SEQ ID NOs: 25 and 28) |

Example 4. Direct Binding of Anti-FLT3 Antibodies to CHO-S Cells Transfected with Human, Cynomolgus or Mouse FLT3 Protein This example demonstrates the binding of anti-FLT3 antibodies to human, mouse and cynomolgus FLT3 protein transiently expressed on cells.

Materials and Methods

The binding of seven anti-FLT3 antibodies to human, cynomolgus or mouse FLT3 protein expressed on CHO-S cells was evaluated and compared to that of an IMC-EB10 analogue.

The anti-FLT3 antibodies were incubated with the hamster CHO-S cell line transiently expressing human, cynomolgus or mouse FLT3 for 30 minutes at 4° C. The cells were washed twice and subsequently incubated for an additional 20 minutes with AF647-conjugated secondary anti-human IgG (H+L) antibody. After the washing step, antibody binding was detected using the high-throughput flow cytometer iQue Screener PLUS (Sartorius) measuring the GeoMean of AF647 signal in each well. Every concentration was assayed in triplicate and a 12-point titration curve was generated for each antibody.

Results

Figure 2:
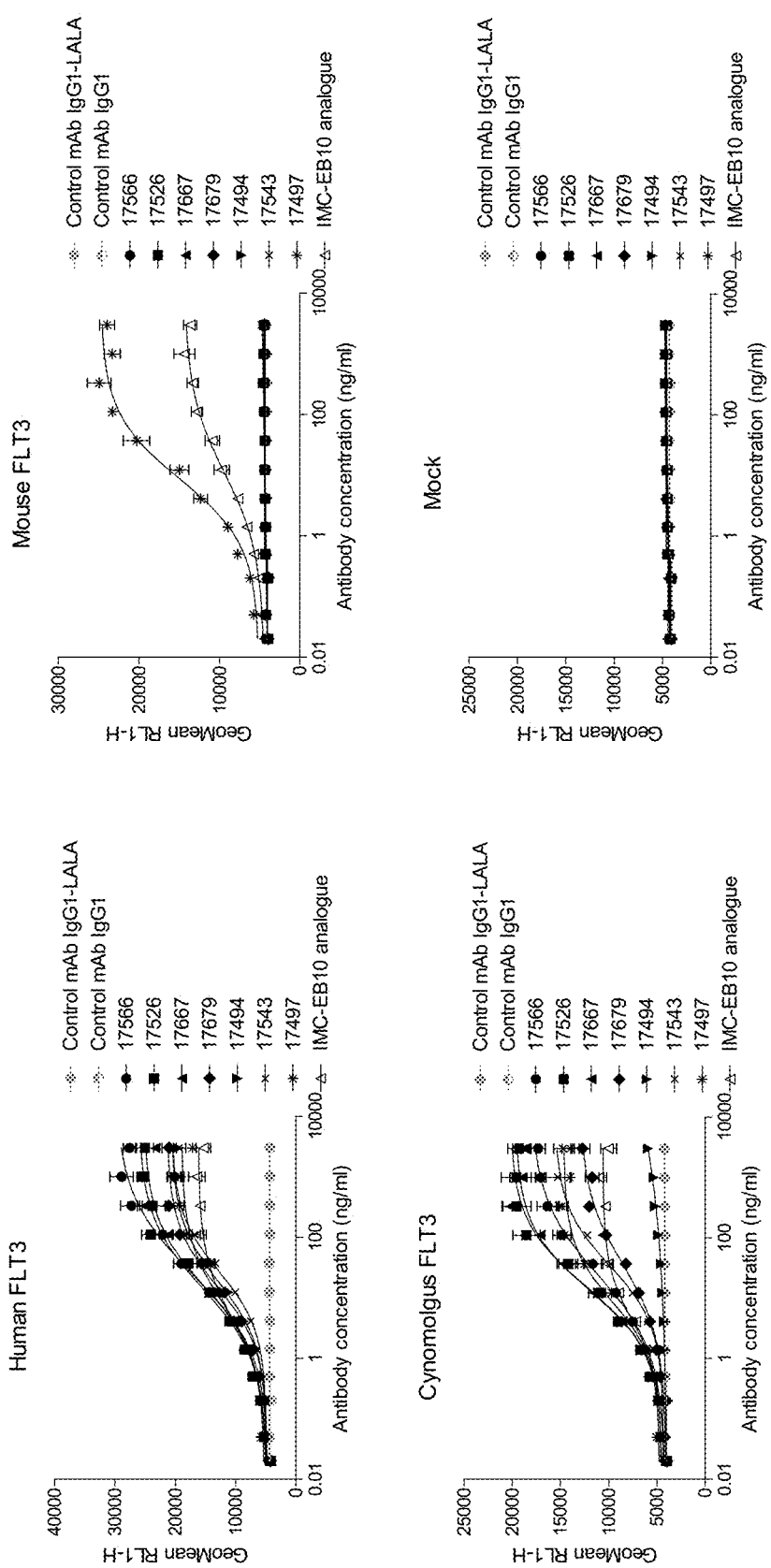
FIG. 2 is a set of graphs showing the binding of the indicated anti-FLT3 antibodies or controls to human (top left), cynomolgus (bottom left) or mouse (top right) FLT3 expressed on CHO-S cells. Mock transfected CHO-S cells (bottom right) were used as a negative control. Data are presented as mean±SEM.

The binding curves of the antibodies to human, cynomolgus or mouse FLT3 expressed on cells are shown in FIG. 2. The assayed antibodies bind to cell-displayed human, cynomolgus or mouse FLT3 protein with different potency and efficacy.

Example 5. Blocking of FLT3 Ligand Binding to Human FLT3 by Seven Anti-FLT3 Antibodies Materials and Methods Binding of anti-FLT3 antibodies to recombinant human FLT3 ECD his-tagged fusion receptor (Sino Biological) and their blocking/non-blocking of FLT3L were measured by Bio-layer Interferometry (BLI) on an Octet QK384 instrument (ForteBio). His-tagged FLT3 was immobilized on pre-equilibrated Anti-Penta-HIS (HIS1 K) Biosensor (ForteBio) for 600 s, followed by 600 s association of 500 nM anti-FLT3 antibodies, and 300 s association of 100 nM FLT3L and 500 nM mAbs. Total FLT3L binding response to immobilized FLT3 was measured in parallel. Data was analysed in the ForteBio Data Analysis (8.2) program.

Results

Figure 3:
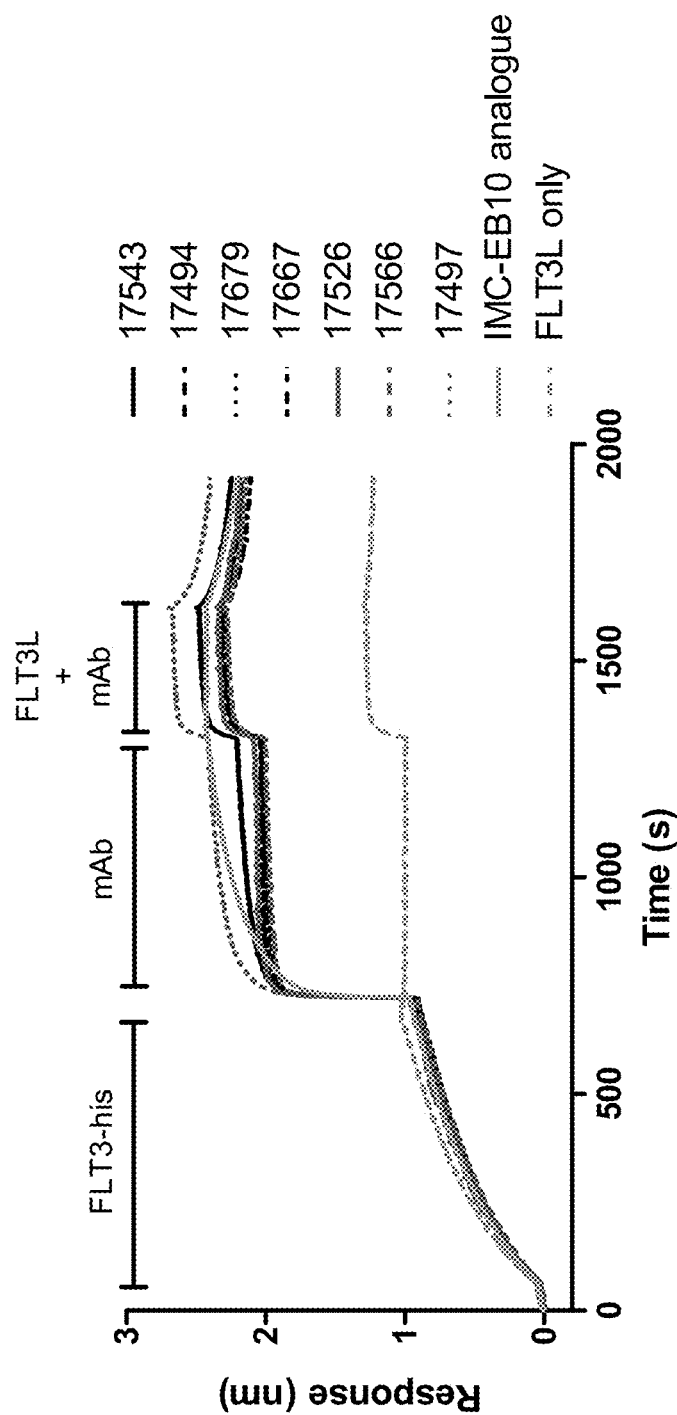
FIG. 3 is a sensorgram showing the FLT3L blocking properties of the indicated anti-FLT3 antibodies. His-tagged FLT3 (FLT3-his) was immobilized on a penta-his biosensor ("penta-his" disclosed as SEQ ID NO: 79) and anti-FLT3 antibodies (mAb) were associated before binding of FLT3L and antibodies (FLT3L+mAb). Total FLT3L binding to FLT3 was measured in parallel (FLT3L only).

The blocking profiles of antibodies 17543, 17494, 17679, 17667, 17526, 17566, 17497, and control mAb are shown in FIG. 3. None of the anti-FLT3 mAbs blocked FLT3L binding to FLT3 at saturating conditions except the IMC-EB10 analogue, which blocked binding of the ligand to FLT3 completely.

Example 6. Blocking of FLT3 Ligand-Fc Binding to CHO-S Cells Transfected with Human, Cynomolgus or Mouse FLT3 Protein by Seven Anti-FLT3 Antibodies This example describes the blocking of FLT3 ligand-Fc protein binding to human, cynomolgus or mouse FLT3 protein expressed on CHO-S cells by anti-FLT3 antibodies.

Materials and Methods

The binding of seven anti-FLT3 antibodies to human, cynomolgus or mouse FLT3 protein expressed on CHO-S cells was evaluated and compared to that of an IMC-EB10 analogue in the presence of FLT3 ligand-Fc protein.

The anti-FLT3 antibodies were incubated with the hamster CHO-S cell line transiently expressing human, cynomolgus or mouse FLT3 for 30 minutes at 4° C. The cells were washed twice and subsequently incubated for an additional 20 minutes with AF647-conjugated FLT3 ligand-Fc. After the washing step, the residual binding of AF647-conjugated FLT3 ligand-Fc protein was detected using the high-throughput flow cytometer iQue Screener PLUS (Sartorius) measuring the GeoMean of AF647 signal in each well. Every concentration was assayed in triplicate and a 12-point titration curve was generated for each antibody.

Results

Figure 4:
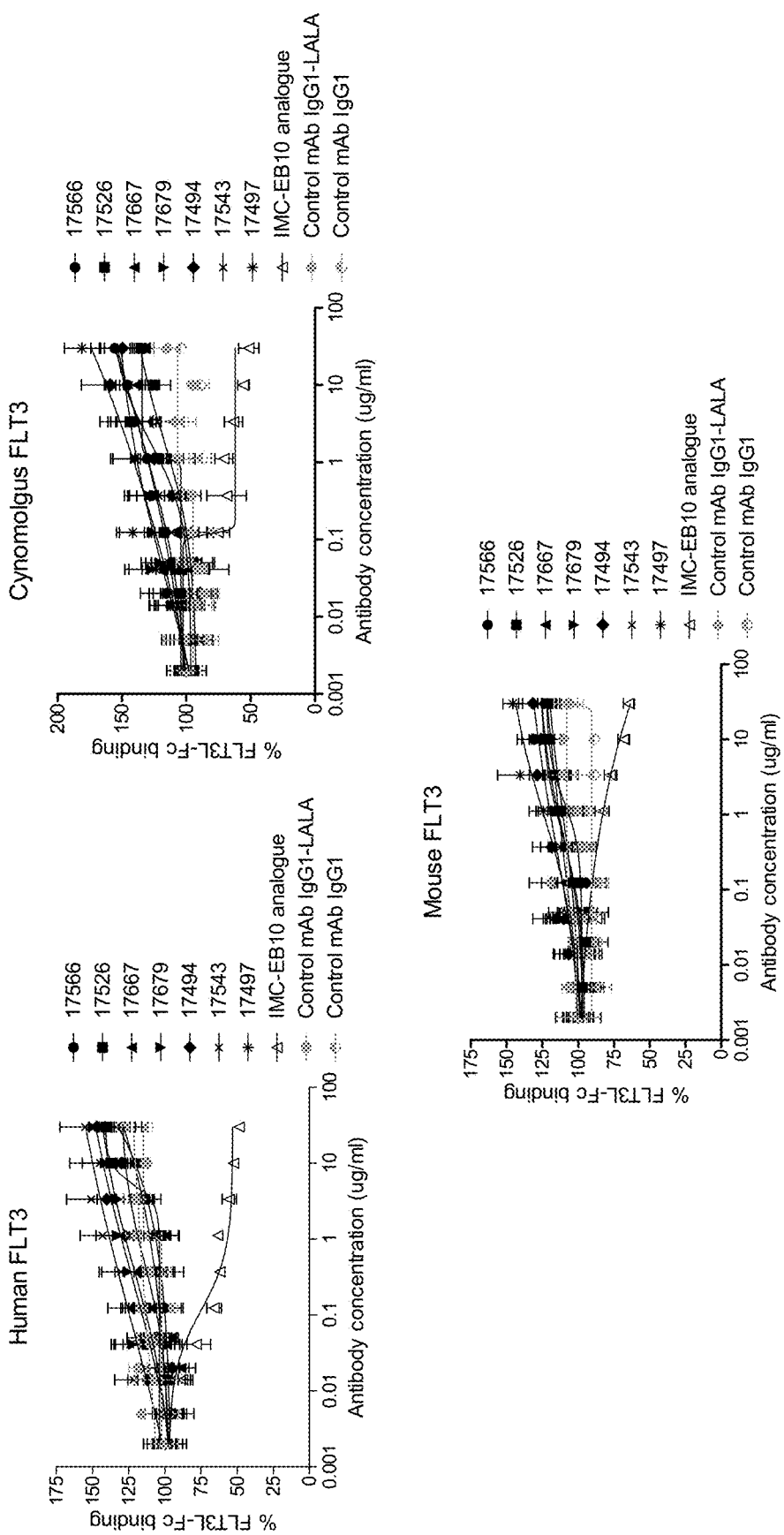
FIG. 4 is a set of graphs showing the ability of the indicated anti-FLT3 antibodies to block binding of FLT3L-Fc to human (top left), cynomolgus (top right) or mouse (bottom) FLT3 expressed on CHO-S cells. Data are presented as mean±SEM.

The blocking curves of the antibodies to human, cynomolgus or mouse FLT3 expressed on cells are shown in FIG. 4. The assayed antibodies did not block binding of AF647-conjugated FLT3L-Fc protein to cell-displayed human, cynomolgus or mouse FLT3 protein at any concentration tested. The IMC-EB10 analogue antibody partially blocked binding of AF647-conjugated FLT3 ligand-Fc protein to cell-displayed human, cynomolgus or mouse FLT3 protein.

Example 7. In Vitro Functional Activity of Anti-FLT3 Antibodies in EOL-1 Proliferation Assay This example describes in vitro functional evaluation of seven anti-FLT3 monoclonal antibodies with the purpose of demonstrating dose-dependent agonistic activity. The antibodies were evaluated for their ability to stimulate proliferation of the FLT3 expressing cancer cell line EOL-1. FLT3 ligand was included for comparison.

Materials and Methods

Seven anti-FLT3 antibodies were evaluated in further detail in vitro for their ability to induce proliferation of the FLT3 expressing cancer cell line EOL-1. The EOL-1 cells were seeded in RPMI 1640 Glutamax media supplemented with 0.5% FBS and 1% P/S and incubated for 5 days with a two-fold titration of the indicated antibodies starting from 25 μg/mL. A two-fold titration of FLT3 ligand starting from 1 μg/mL was included for comparison. Cell proliferation was quantified using WST-1 cell proliferation reagent (Roche) as per manufacturer's instructions.

Results

Figure 5:
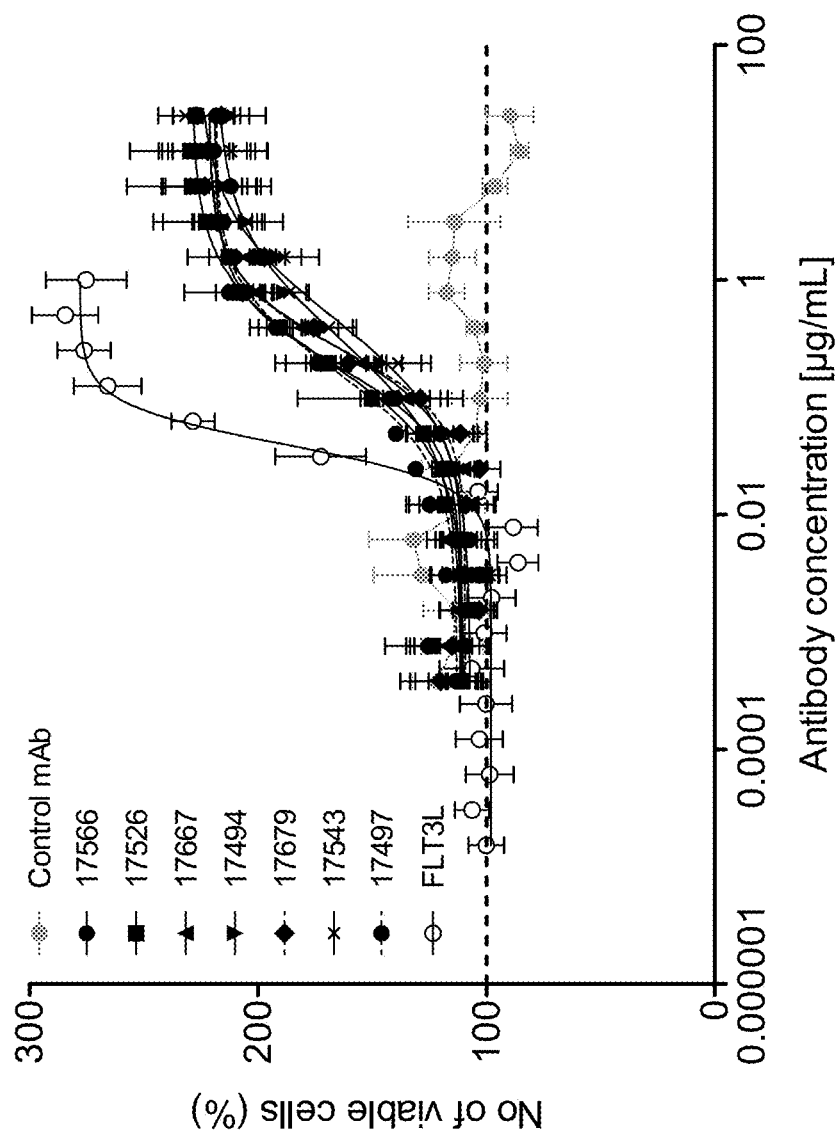
FIG. 5 is a graph showing the proliferation of EOL-1 cells treated with the indicated antibodies or FLT3 ligand. "Control mAb" is an antibody against an irrelevant protein in $IgG_1$-LALA format. Data are normalized to untreated control and each data point on the curves represents mean±SEM (n=3).

The proliferation of EOL-1 cells after treatment with anti-FLT3 antibodies is shown in FIG. 5. All seven antibodies tested demonstrated a dose-dependent stimulatory capacity as shown by their ability to induce proliferation of the EOL-1 cells.

Example 8. In Vitro Functional Activity of Anti-FLT3 Antibodies in Different IgG Formats in a Cell Proliferation Assay This example describes in vitro functional evaluation of anti-FLT3 monoclonal antibodies in either $IgG_1$-LALA or $IgG_2$ format with the purpose of demonstrating a dose-dependent agonistic activity. The antibodies were evaluated for their ability to stimulate proliferation of the FLT3 expressing cancer cell lines EOL-1 and OCI-AML5.

Materials and Methods

EOL-1 and OCI-AML5 cells were seeded in RPMI 1640 Glutamax media supplemented with 0.5% FBS and 1% P/S, and incubated for 5 days with a two-fold titration of the indicated antibodies starting from 25 μg/mL. Cell proliferation was quantified using WST-1 cell proliferation reagent (Roche) as per the manufacturer's instructions.

Results

Figure 6A:
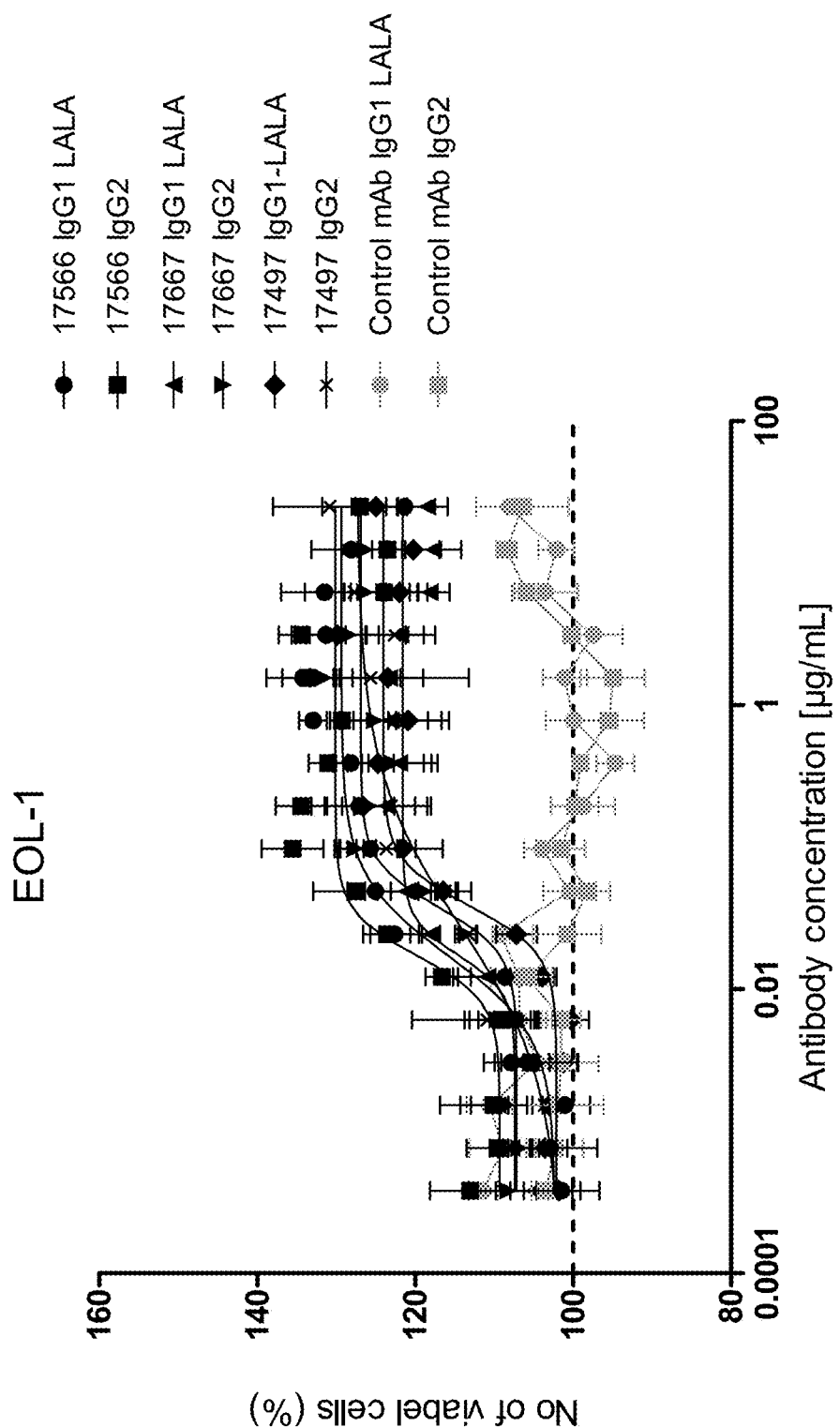
FIGS. 6A and 6B are graphs showing the proliferation of EOL-1 cells (FIG. 6A) or OCI-AML5 cells (FIG. 6B) treated with the indicated antibodies. Data are normalized to untreated control and each data point on the curves represents mean±SEM (n=3).
Figure 6B:
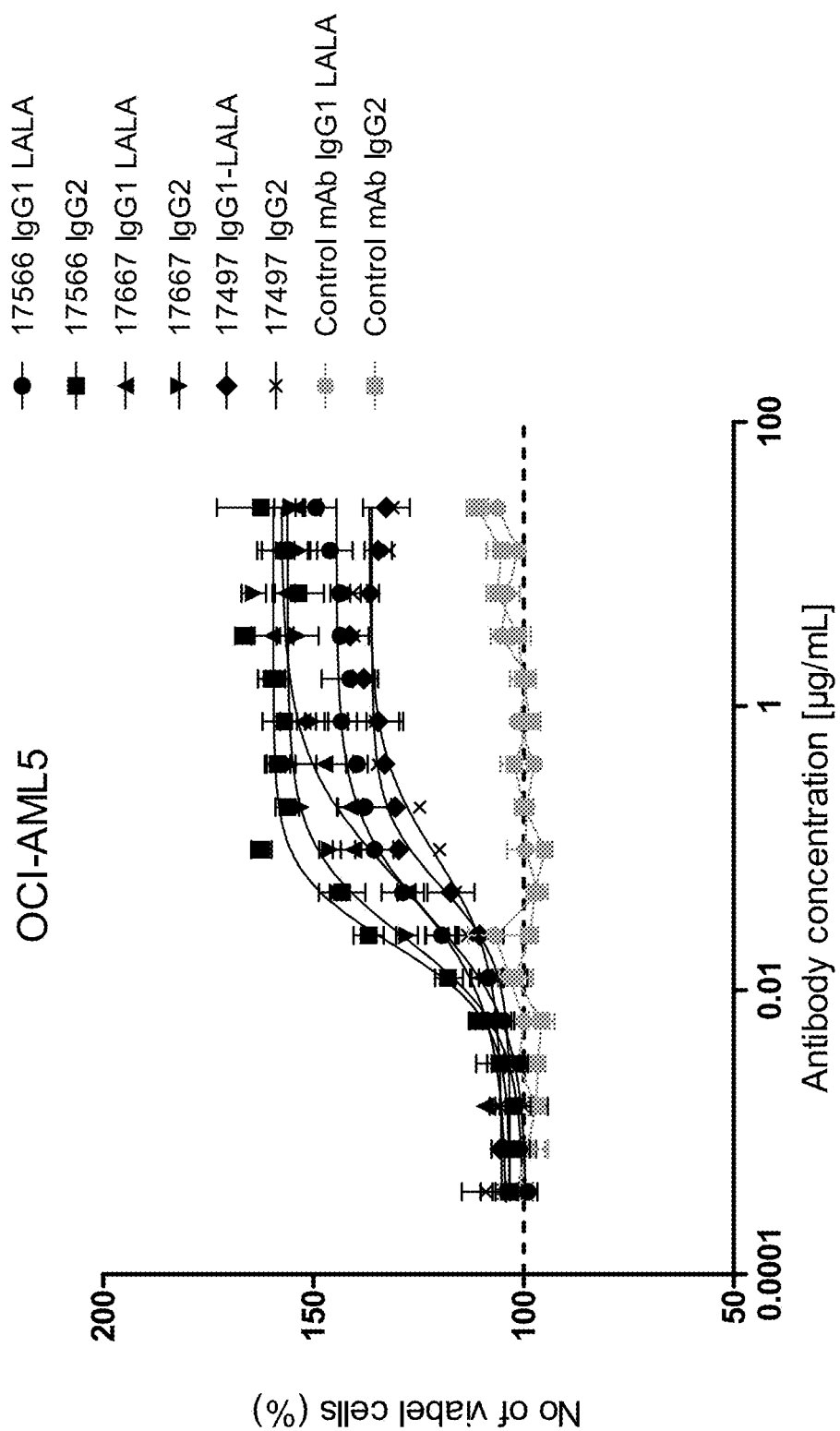
Figure 7:
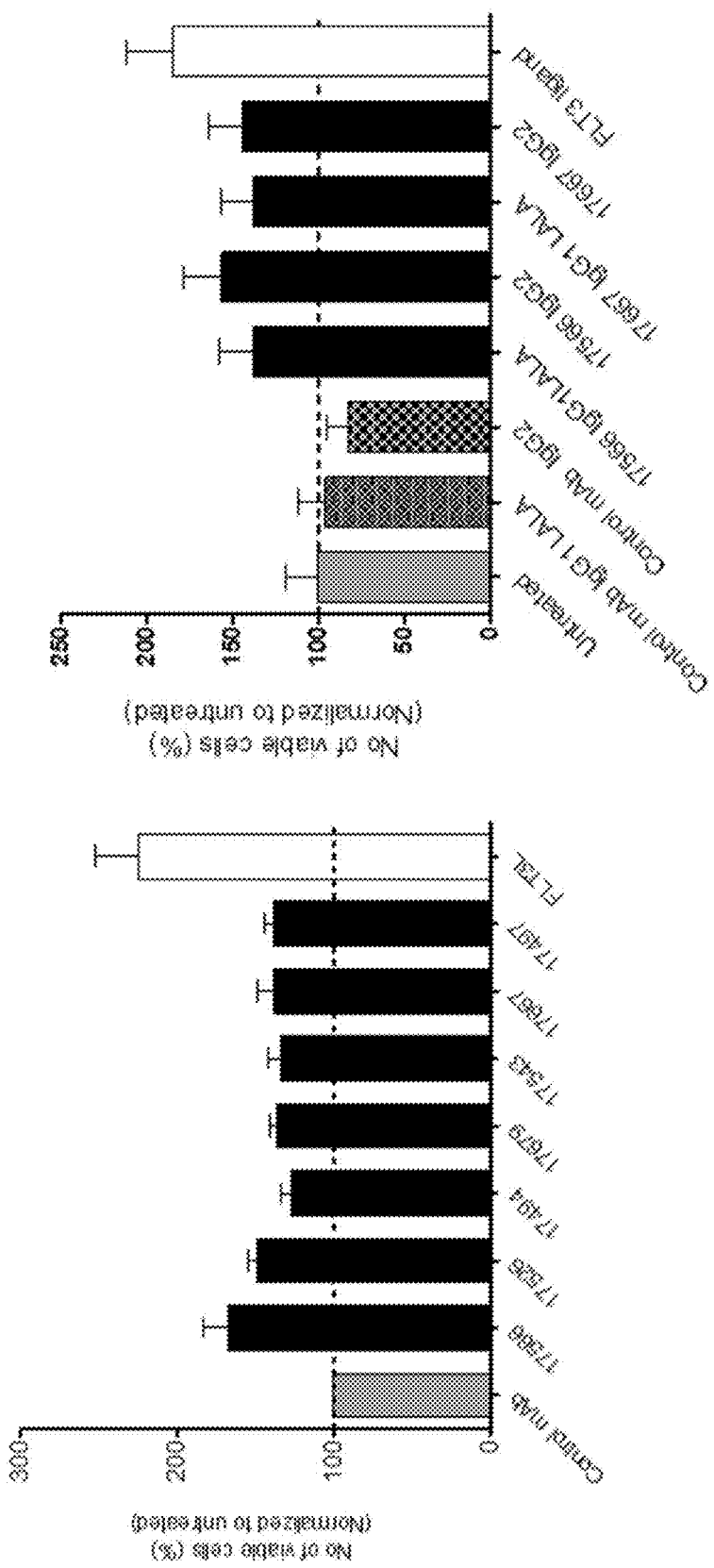
FIG. 7 is a graph showing the proliferation of human primary CD34$^+$ stem cells treated with the indicated antibodies or FLT3 ligand. The left panel shows the effect of the indicated antibodies in $IgG_1$-LALA format and the right panel shows the effect of the indicated antibodies in $IgG_1$-LALA or $IgG_2$ format. "Control mAb" is an antibody against an irrelevant protein in $IgG_1$-LALA format. Data are presented as mean±SEM (n=4).

The proliferation of EOL-1 cells and OCI-AML5 cells after treatment with anti-FLT3 antibodies is shown in FIGS. 6A and 6B, respectively. Both the $IgG_1$-LALA and $IgG_2$ isotypes of the selected antibodies demonstrated a dose-dependent stimulatory capacity, as shown by their ability to induce proliferation of both the EOL-1 and OCI-AML5 cell lines.

Example 9. Effect of Anti-FLT3 Antibodies on Proliferation of Primary Human $CD34^+$ Stem Cells This example describes in vitro functional evaluation of seven anti-FLT3 monoclonal antibodies, as well as selected antibodies in $IgG_1$-LALA or $IgG_2$ format, with the purpose of validating agonistic activity in primary human $CD34^+$ stem cells. The antibodies were evaluated for their ability to stimulate proliferation of primary human $CD34^+$ stem cells. FLT3 ligand was included for comparison.

Materials and Methods

Primary human bone marrow derived $CD34^+$ stem cells were obtained from the American Type Culture Collection (ATCC). The $CD34^+$ stem cells were seeded in Hematopoietic Progenitor Cell (HPC) expansion medium DXF (PromoCell) supplemented with 50 ng/mL thrombopoietin (TPO) and 25 ng/mL IL-3 and incubated for 7 days with the indicated antibodies (25 μg/mL) or FLT3 ligand (250 ng/mL). Cell proliferation was quantified using WST-1 cell proliferation reagent (Roche) as per manufacturer's instructions.

Results

The proliferation of primary human $CD34^+$ stem cells after treatment with anti-FLT3 antibodies is shown in FIG.

7. It is evident that all seven tested anti-FLT3 antibodies induced proliferation of primary human CD34+ stem cells, confirming their stimulatory capacity (left panel). The selected antibodies in IgG$_1$-LALA and IgG$_2$ format also induced proliferation of primary human CD34+ stem cells (right panel). FLT3 ligand was included as a positive control.

Example 10. Effect of Anti-FLT3 Antibodies on Differentiation of Human Primary CD34+ Stem Cells This example describes in vitro functional evaluation of two anti-FLT3 monoclonal antibodies in IgG$_1$-LALA and IgG$_2$ format for the purpose of validating agonistic activity in primary human CD34+ stem cells. The antibodies were evaluated for their ability to induce differentiation of primary human CD34+ stem cells. FLT3 ligand was included for comparison.

Materials and Methods

Primary human bone marrow derived CD34+ stem cells were obtained from the American Type Culture Collection (ATCC). The CD34+ stem cells were seeded in IMDM medium containing 10% FBS, 1% PenStrep, 10 mM HEPES, 20 µM 2-mercaptoethanol, 20 ng/mL IL-3, 20 ng/mL GM-CSF, and 20 ng/mL IL-4. Subsequently, anti-FLT3 antibody (25 µg/mL) or FLT3 Ligand (250 ng/mL) was added to the culture and the cells were incubated for two weeks. Fresh medium containing supplements and anti-FLT3 antibody or FLT3 ligand was added twice during two weeks of culture. The cells were collected and expression of CD14 and CD1c was analyzed by flow cytometry. In brief, the cells were washed twice in PBS and stained with Human BD Fc Block and Zombie Aqua Fixable Viability dye (dead cell marker) for 20 minutes at 4° C. Subsequently, the cells were washed and stained with antibodies against cell surface markers (anti-CD14-FITC, anti-CD1c-PE-CF594, anti-CD11c-BV421, anti-CD123-PE, anti-CD141-PerCPCy5.5) for 30 minutes at 4° C. in the dark. After two final washes, the cells were analyzed using a BD FACSCelesta flow cytometer and FacsDiva Software. Data analyses were performed using GraphPad Prism 5.0.

Results

Figure 8A:
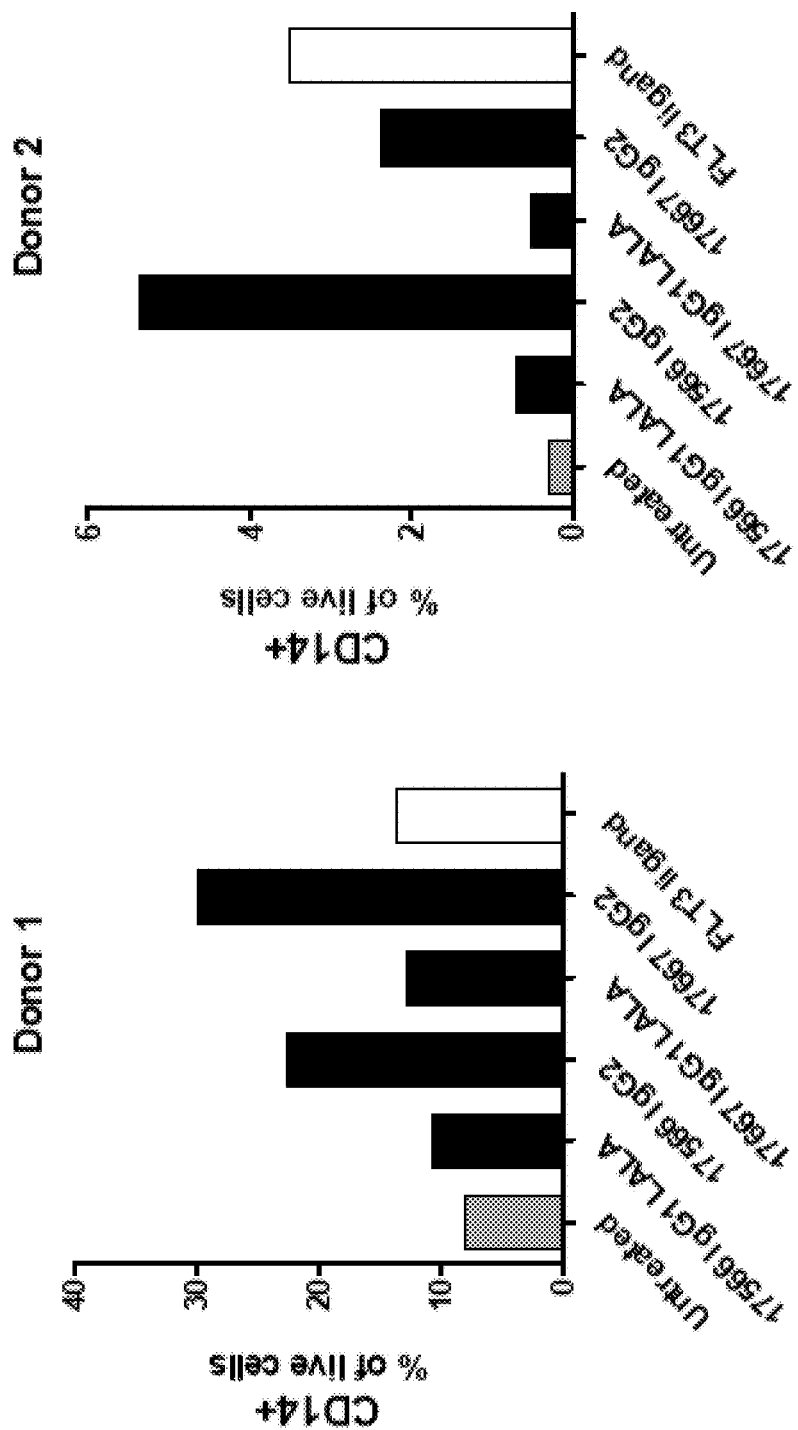
FIGS. 8A-8C are a set of graphs showing the differentiation of human primary CD34$^+$ stem cells from two donors treated with the indicated antibodies or FLT3 ligand. Data are presented as frequency of CD14$^+$ (FIG. 8A) and CD1c$^+$ (FIG. 8B) cells and dendritic cell subpopulations (FIG. 8C) as compared to untreated control.
Figure 8B:
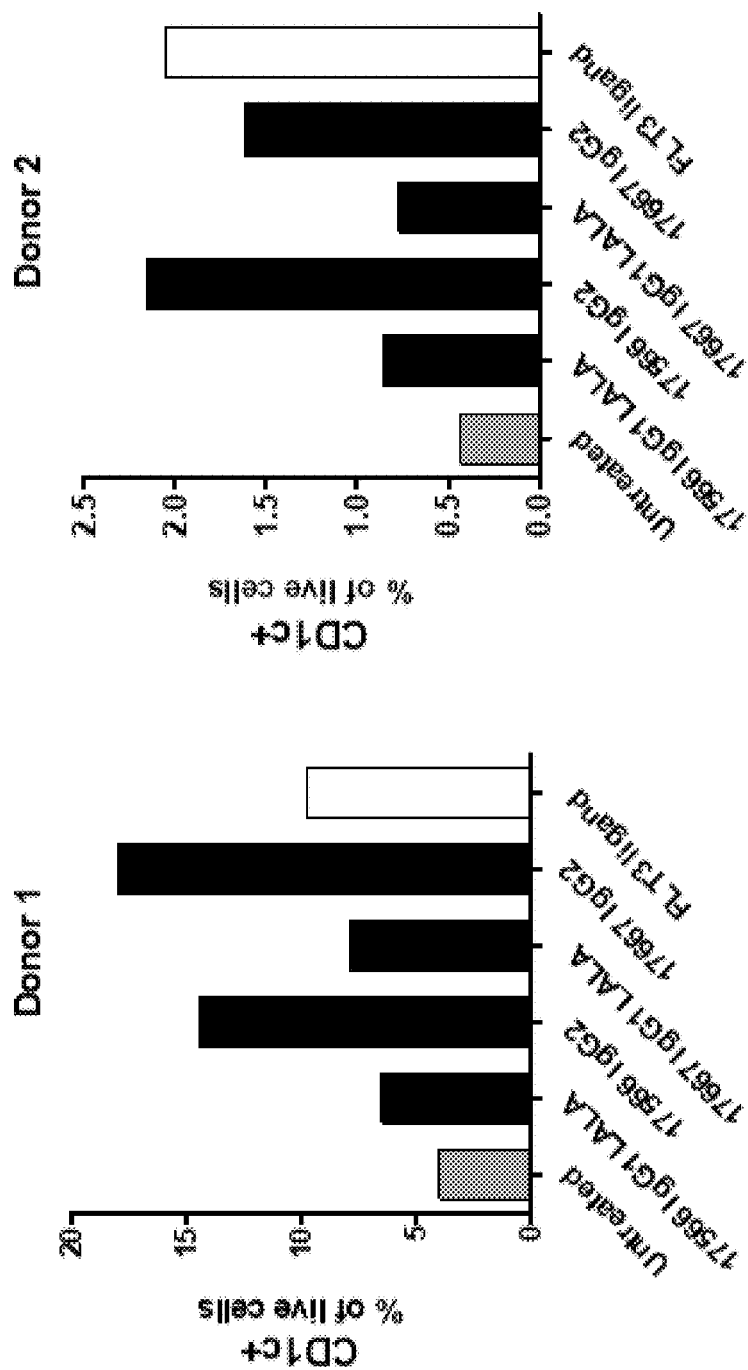
Figure 8C:
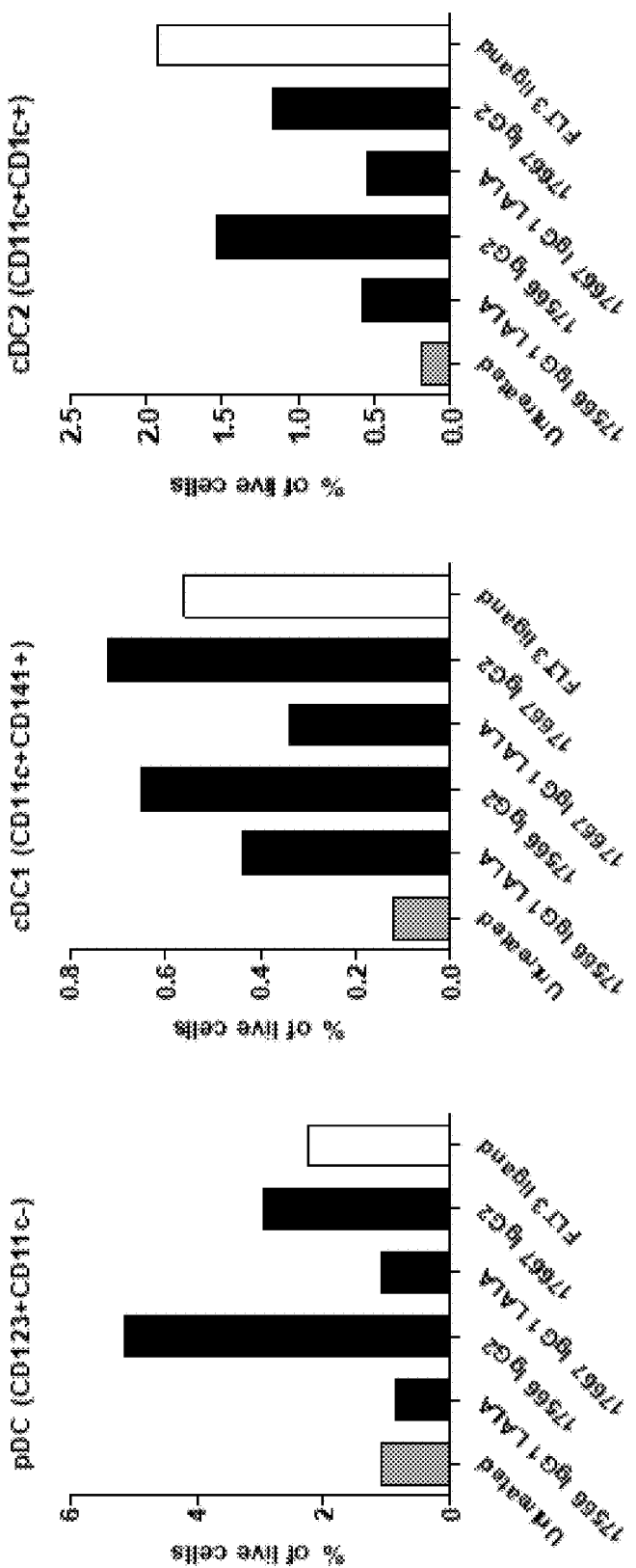

The agonistic activity of two anti-FLT3 antibodies was evaluated through their ability to induce differentiation of primary human CD34+ stem cells. Both of the tested anti-FLT3 antibodies were able to induce differentiation of the primary human CD34+ stem cells, as shown by their ability to increase the frequency of CD14+ (FIG. 8A) and CD1c− (FIG. 8B) cells, as well as dendritic cell subpopulations (pDC, cDC1, and cDC2) (FIG. 8C), compared to untreated control. FLT3 ligand was included as a positive control.

Example 11. In Vivo Functional Activity of Anti-FLT3 Antibody in Balb/c Mice

This example describes in vivo functional evaluation of an anti-FLT3 monoclonal antibody in IgG$_1$-LALA or IgG$_2$ format with the purpose of validating its ability to induce dendritic cell expansion and mobilization in immunocompetent mice. FLT3 ligand was included for comparison.

Materials and Methods

Forty female Balb/c mice were divided into eight treatment groups with five animals in each. Treatment was initiated on day 0 and terminated on day 13. The mice received intraperitoneal injection of vehicle; anti-FLT3 antibody at 0.1 mg/kg, 1 mg/kg, or 10 mg/kg twice weekly; or intraperitoneal injection of 10 µg of FLT3L five times weekly. At termination, spleens from all mice were harvested and analyzed by flow cytometry. Cells were stained with anti-CD3-FITC, anti-CD370-PE, anti-CD8-PerCP-Cy5.5, anti-CD11b-PE-Cy7, anti-I-A/I-E-APC-Cy, anti-CD11c-BV421, anti-Ly6C-FITC, anti-CD3-PerCP-Cy5.5 and anti-CD45R-APC antibodies. Zombie Aqua was used for live/dead cell discrimination. Cells were analyzed using a BD FACSVerse flow cytometer and FacsDiva Software. Data analyses were performed using GraphPad Prism 5.0.

Results

Figure 9A:
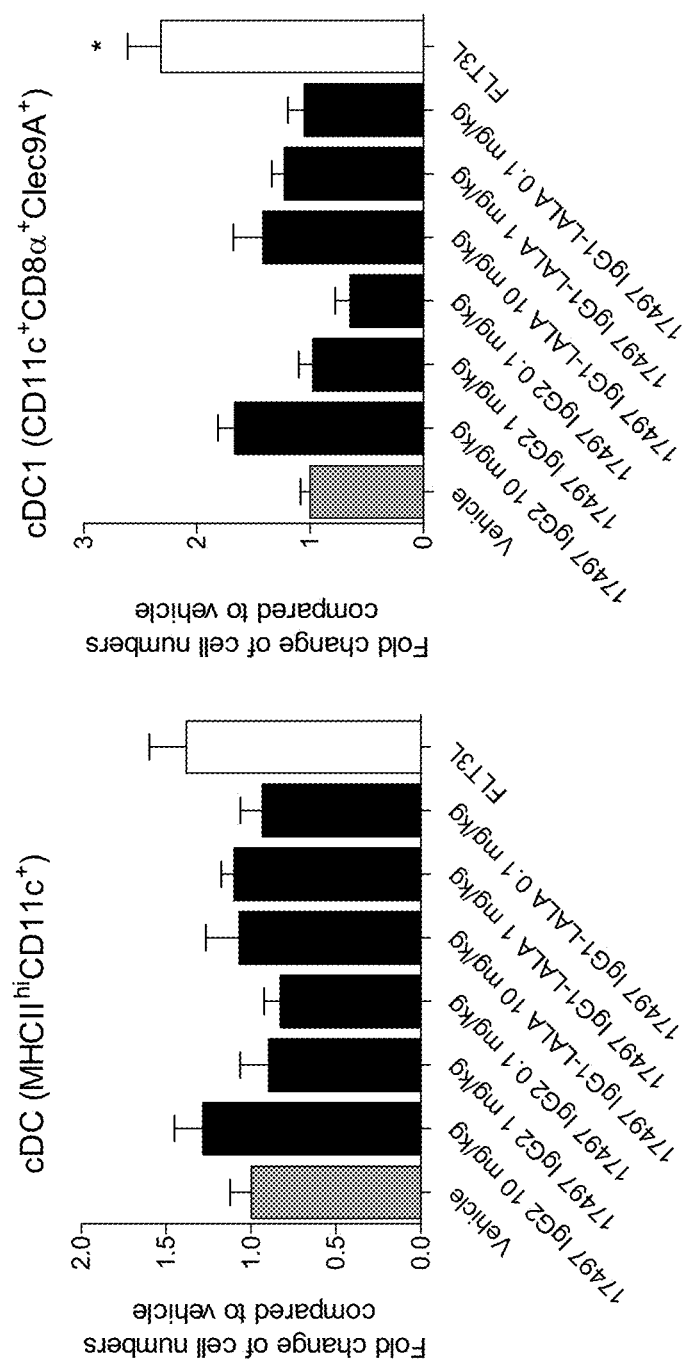
FIGS. 9A and 9B are a set of graphs showing fold increase in absolute cell numbers of splenic dendritic cell subsets in Balb/c mice after treatment with an indicated antibody or FLT3L, compared to vehicle.
Figure 9B:
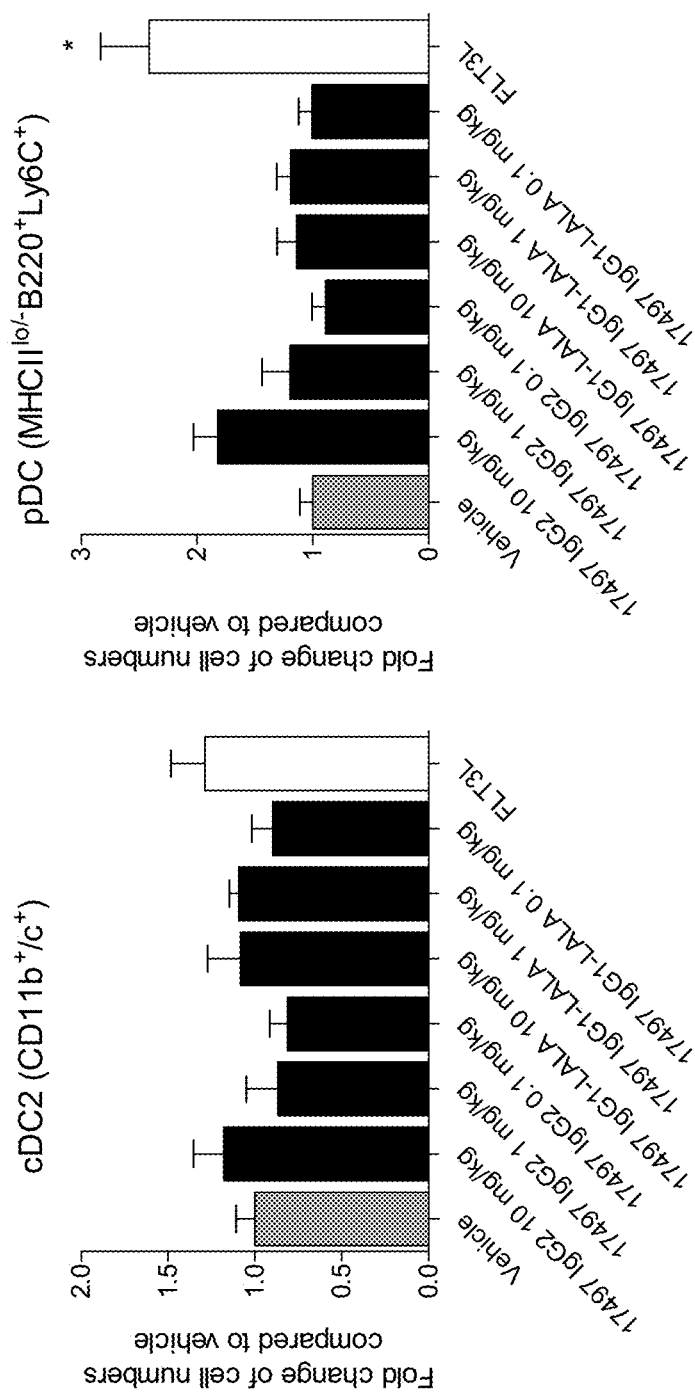

The in vivo agonistic activity of an anti-FLT3 antibody in IgG$_1$-LALA or IgG$_2$ format was evaluated in terms of its ability to induce dendritic cell (DC) mobilization in immunocompetent mice at three different doses. The most efficient dose of anti-FLT3 antibody in IgG$_1$-LALA and IgG$_2$ format for inducing DC mobilization of most of the subpopulations was 10 mg/kg, as demonstrated by fold increase in cell numbers compared to vehicle (FIGS. 9A and 9B). FLT3 ligand was included as a positive control.

Example 12. In Vivo Functional Activity of Anti-FLT3 Antibody in CD34 Humanized Mice This example describes in vivo functional evaluation of an anti-FLT3 monoclonal antibody with the purpose of validating its ability to induce dendritic cell mobilization in immunocompromised mice reconstituted with human CD34+ stem cells ("CD34 humanized mice"). FLT3 ligand was included for comparison.

Materials and Methods

Thirty-six female NOD/Shi-SCID/IL-2Rγnull (NCG) mice were humanized using hematopoietic stem cells (CD34+) isolated from human cord blood. Only mice with a humanization rate (hCD45/total CD45) above 25% were used for the study. Mice were randomized into six treatment groups with six animals in each group based on humanization rate and CD34 donor. Treatment was initiated on day 0 and terminated on day 11. The mice received intraperitoneal injections of vehicle, anti-FLT3 antibody at 1 or 10 mg/kg twice weekly, or intraperitoneal injections of 10 µg of FLT3L five times weekly. At termination, spleen and bone marrow from all mice were harvested and analyzed by flow cytometry. Cells were stained with anti-CD1c-BV421, anti-CD11c-BV510, anti-CD14-BV650, anti-CD123-FITC, anti-CD3-PerCPVio700, anti-CD20-PerCPVio700, anti-CD56-PerCPVio700, anti-CD301-PE, anti-CD141-PE-Vio615, anti-hCD45-PE-Vio770, anti-CD370-APC, and anti-HLA-DR-APC-Cy7 antibodies. Fixable Yellow was used for live/dead cell discrimination. Cells were analyzed using an Attune NxT flow cytometer and FacsDiva Software. Data analyses were performed using GraphPad Prism 5.0.

Results

Figure 10A:
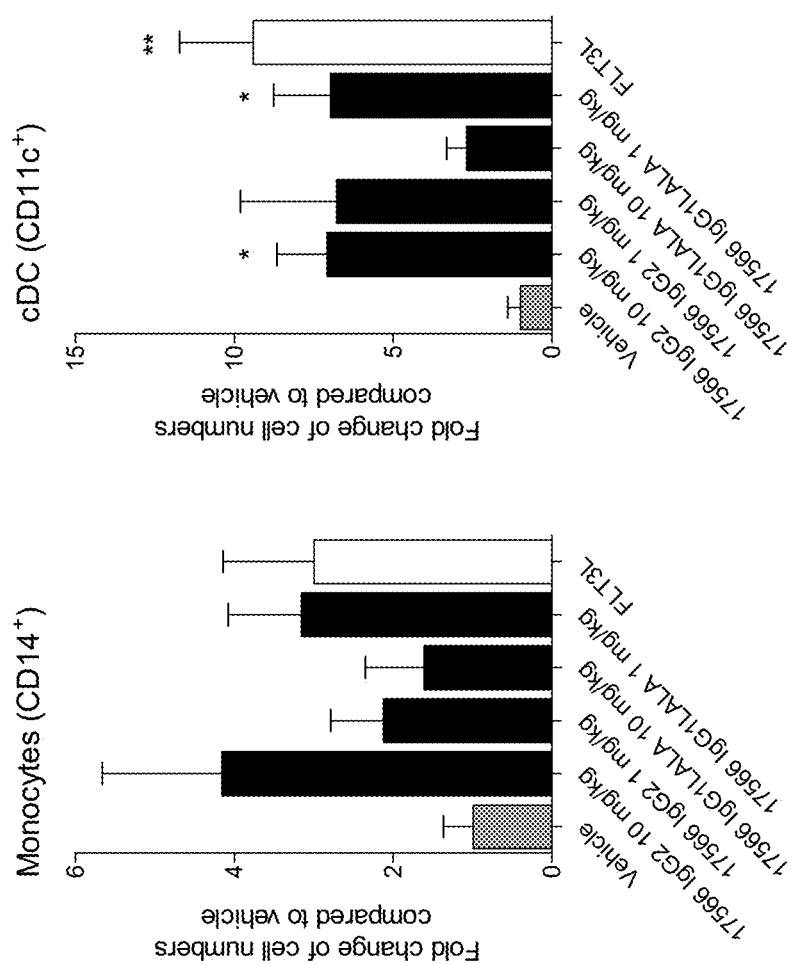
FIGS. 10A-10D are sets of graphs showing the effect on splenic (FIGS. 10A and 10B) and bone marrow (FIGS. 10C and 10D) DC subsets as fold increase in absolute cell numbers after treatment with an anti-FLT3 antibody in $IgG_1$-LALA or $IgG_2$ format or FLT3L, as compared to vehicle, in CD34 humanized NCG mice. The antibody treatments were administered at a dose of 1 mg/kg or 10 mg/kg for each antibody (n=5-6/group).
Figure 10B:
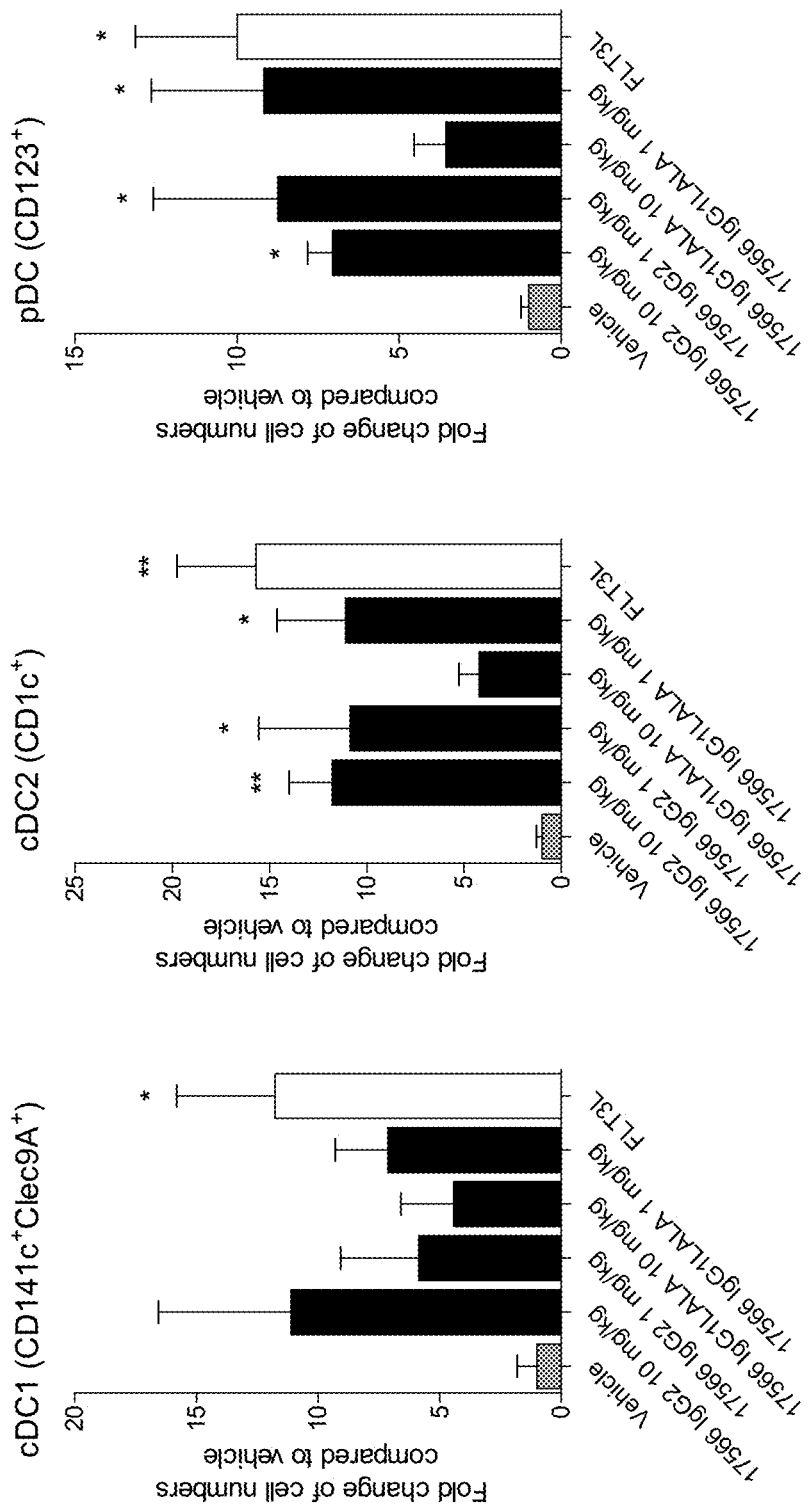
Figure 10C:
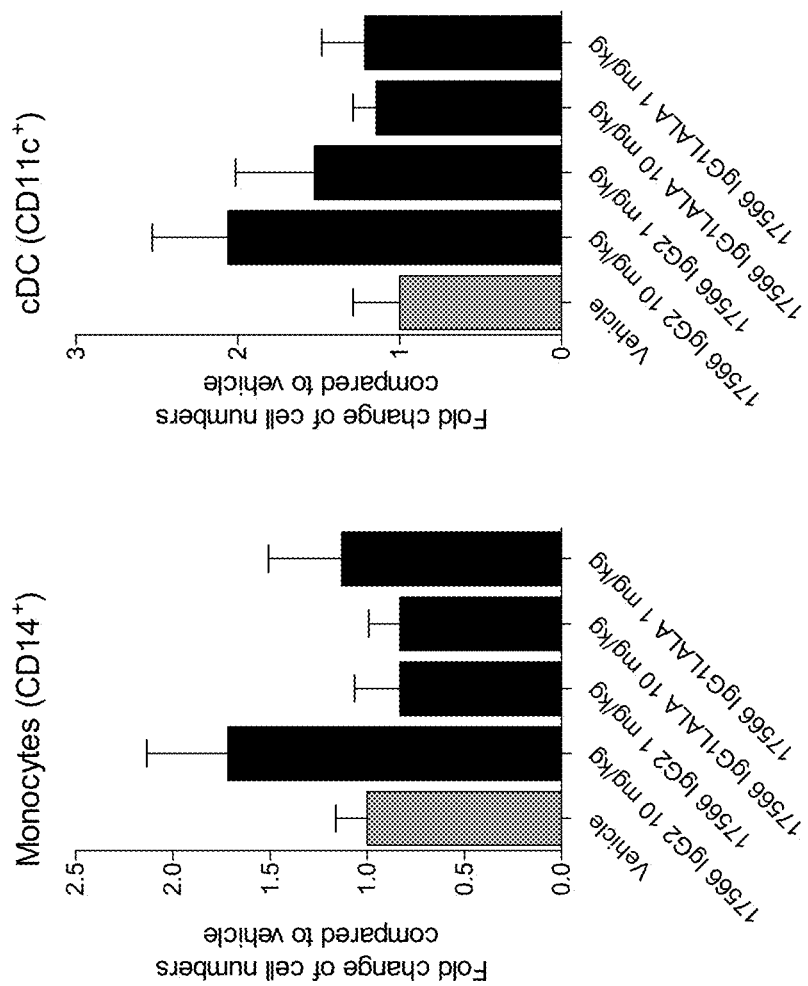
Figure 10D:
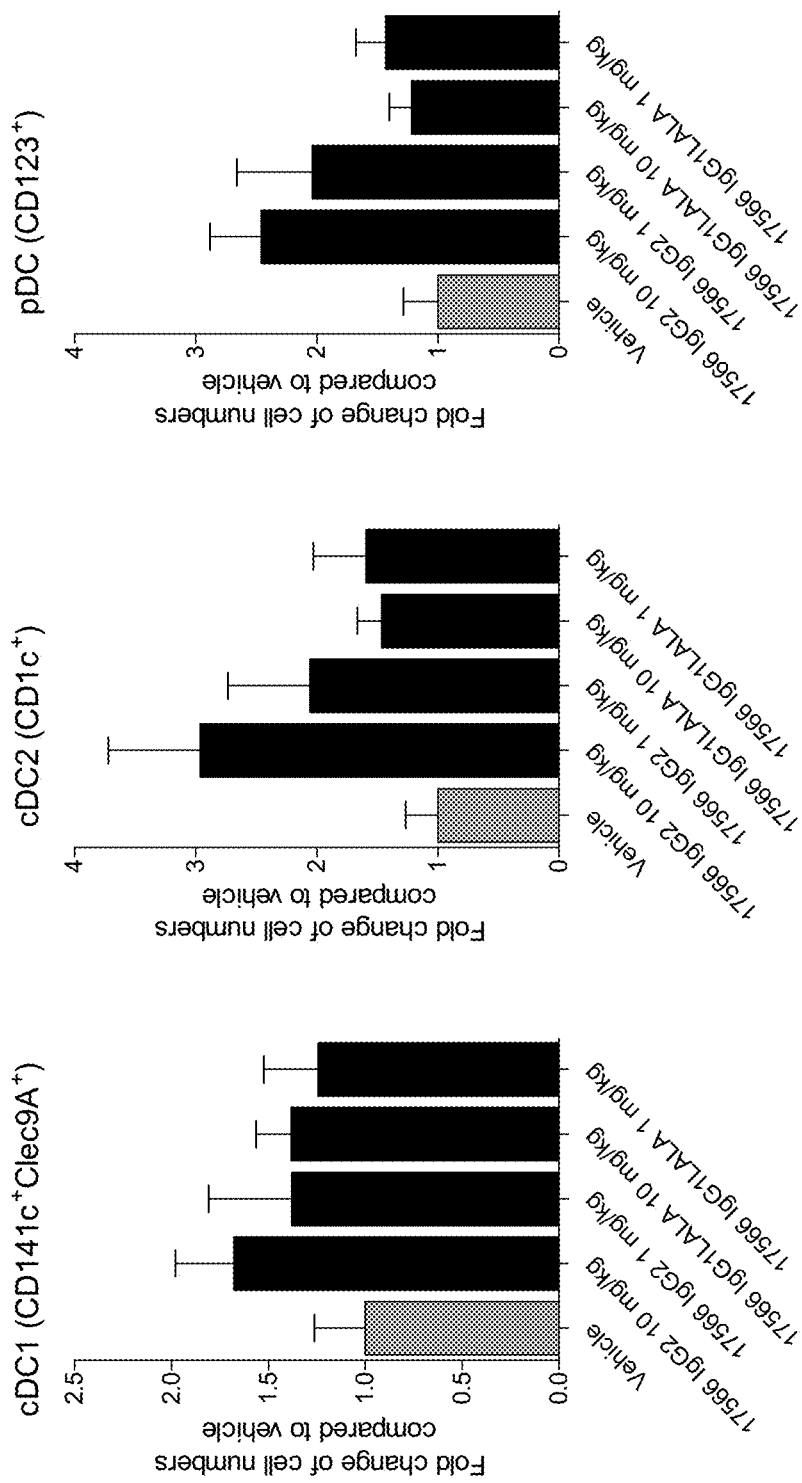

The in vivo agonistic activity of an anti-FLT3 antibody in IgG$_1$-LALA or IgG$_2$ format was evaluated in terms of its ability to induce DC mobilization in CD34 humanized mice at two different doses. In both formats at both doses, the antibody was able to induce DC mobilization of most of the subsets in spleen (FIGS. 10A and 10B) and bone marrow (FIGS. 10C and 10D) as demonstrated in fold increase compared to vehicle. FLT3 ligand was included as a positive control.

Example 13. Effect of Anti-FLT3 Antibody and FLT3 Ligand on Gene Expression in Human Primary CD34+ Stem Cells This example demonstrates that in vitro stimulation of human primary CD34+ stem cells with an agonistic anti-FLT3 antibody induces similar changes in gene expression as the FLT3 ligand, providing evidence of similar stimulation pathways.

Materials and Methods

Primary human bone marrow derived CD34+ stem cells were obtained from the American Type Culture Collection (ATCC). The CD34+ stem cells were seeded in IMDM medium containing 10% FBS, 1% PenStrep, 10 mM HEPES, 20 μM 2-mercaptoethanol, 20 ng/ml IL-3, 20 ng/ml GM-CSF and 20 ng/ml IL-4. Subsequently, anti-FLT3 antibody (25 μg/ml) or FLT3 Ligand (250 ng/ml) was added to the culture and the cells were incubated for two weeks. Fresh medium containing supplements and anti-FLT3 antibody or FLT3 ligand was added twice during two weeks of culture. The cells were collected, and RNA was extracted using the RNeasy Micro kit (Qiagen) as per the manufacturer's instructions. 100 ng RNA was used as input for gene expression analysis on the nCounter SPRINT Profiler. Gene expression was analyzed using nCounter Myeloid Innate Immunity Panel (XT_PGX_huV2_Myeloid, NanoString Technologies), and the nSolver Analysis software was used for data quality control, normalization, and analysis of differential gene expression. Spearman's rank correlation was used to analyze the association between the studied genes.

Results

Figure 11:
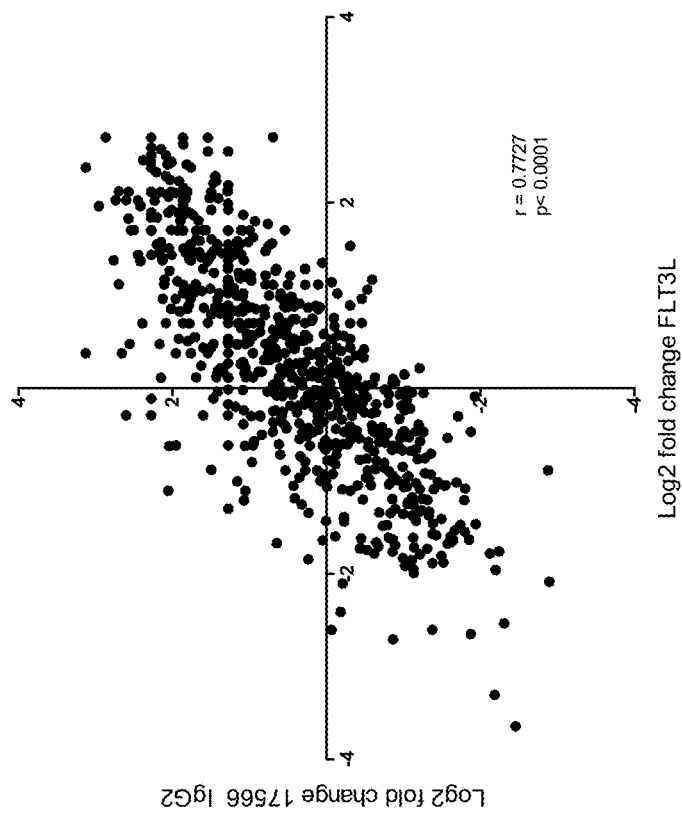
FIG. 11 is a pair of graphs showing the correlation between changes in gene expression in human primary CD34$^+$ stem cells treated with the indicated antibody in $IgG_1$-LALA format (left panel) or $IgG_2$ format (right panel), or FLT3 ligand. Data are presented as log 2 fold change in gene expression compared to negative control antibody.
Figure 11:
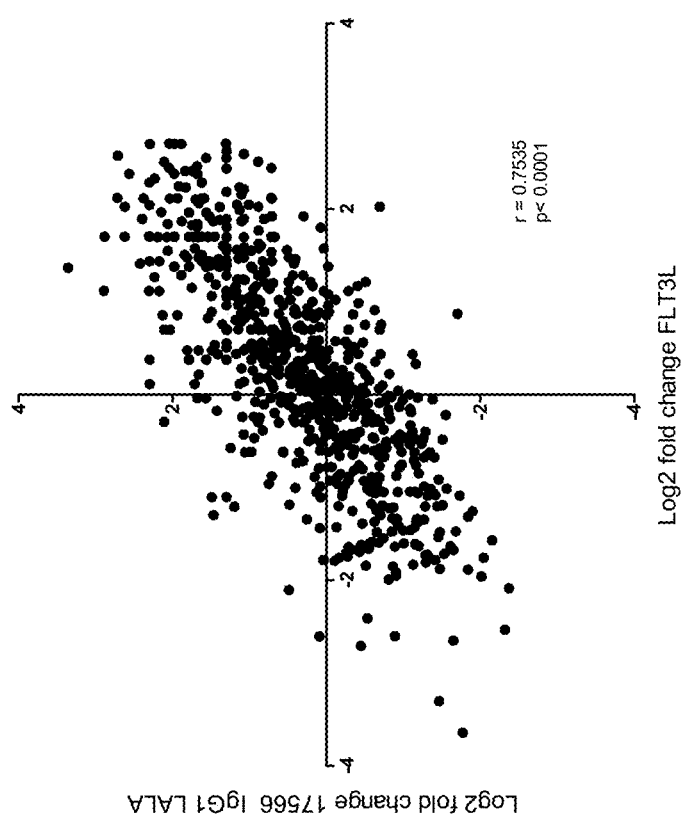

As shown in FIG. 11, the tested antibody in both $IgG_1$-LALA (left panel) and $IgG_2$ (right panel) formats induced similar changes in gene expression as the FLT3 ligand. The strong correlation between the observed changes in gene expression induced by agonistic anti-FLT3 antibodies and FLT3 ligand indicates that they stimulate human primary CD34+ stem cells in a similar way.

Example 14. Binding Kinetics of Anti-FLT3 Fab Fragments to Human FLT3

This example assesses the binding of anti-FLT3 Fab fragments to human FLT3 domain 1 as measured by surface plasmon resonance (SPR).

Materials and Methods

The cDNA (UniProt Accession No. P36888) coding for human FLT3 domain 1 was synthesized and cloned into a vector containing CMV promoter and human Ig Fc sequence (residues P101-K330), resulting in fusion of Ig Fc to the C-terminus, and expressed transiently in an ExpiCHO™ expression system. After harvesting, supernatants were tested for binding to anti-FLT3 Fabs by surface plasmon resonance (SPR) using Carterra LSA. An HC200M (Carterra) chip was functionalized by goat anti-human Ig Fc (Southern Biotech) using amine-coupling. The chip was activated by freshly prepared 0.4 M EDC, 0.1 M sulfo-NHS, and 0.1 M MES, pH 5.5 (1:1:1 v/v/v) for 5 min, coupled with 75 μg/mL anti-human Ig Fc in 10 mM sodium acetate, pH 4.5, for 10 min, and excess reactive esters were quenched for 3 min by injection of 1 M ethanolamine, pH 8.5. The instrument was primed in running buffer (PBS pH 7.4, 0.01% Tween-20, 0.5 mg/ml BSA). After priming and washing, FLT3 fusion proteins in culture supernatants were captured onto individual spots of the chip for 12 minutes as duplicates. Fab analytes were each prepared in running buffer. Kinetic analysis was performed by applying kinetic titration series of monomeric Fabs at increasing concentrations. Fab association was performed for 5 minutes and antigen dissociation was recorded for 5 minutes. After each cycle of Fab injections, the surface was regenerated by 0.45% H3PO4 for 2×20 s and washed for 5 min in running buffer. Binding responses were processed and analyzed using Carterra's KIT software tool. Processed data was fitted to a simple Langmuir 1:1 binding model for calculation of the on-rate (kon or ka), off-rate (koff or kd) and affinity (KD) constants.

Results

Binding kinetics of Fab fragments of antibodies 17566, 17526, 17667, 17543, and 17497 to human FLT3 domain 1 are shown in Table 7 below. Data are presented as mean±SEM, n=4.

TABLE 7

Binding kinetics of anti-FLT3 Fab fragments to human FLT3 domain 1 as measured by SPR

| Fab | $k_{on}$ (×10$^5$M$^{-1}$ s$^{-1}$) | $k_{off}$ (×10$^{-3}$s$^{-1}$) | $K_D$ (nM) |
|---|---|---|---|
| 17566 | 8.9 ± 0.2 | 4.6 ± 0.3 | 5.2 ± 0.4 |
| 17526 | 11.5 ± 0.3 | 7.6 ± 0.3 | 6.6 ± 0.4 |
| 17667 | 16.5 ± 0.6 | 14.5 ± 0.4 | 8.9 ± 0.3 |
| 17543 | 5.2 ± 0.9 | 9.9 ± 0.6 | 19.3 ± 1.4 |
| 17497 | 9.8 ± 0.9 | 3 ± 0.3 | 3.1 ± 0.4 |

Example 15. Epitope Binning of Anti-FLT3 Antibodies

This example describes the grouping of anti-FLT3 antibodies into epitope bins based on paired competition patterns measured by Surface Plasmon Resonance (SPR). Antibodies belonging to different epitope bins recognize different epitopes on the FLT3 ECD.

Materials and Methods

Investigation of paired antibody competition was performed by SPR using an IBIS-MX96 instrument (IBIS, Netherlands). Anti-FLT3 antibodies were diluted to 3 μg/ml in PBS and spotted onto a G-a-hu-IgG Fc SensEye® by capturing for 15 minutes using a Continuous Flow Microspotter, followed by blocking of residual binding sites by Herceptin (trastuzumab) and chemical cross-linking by SensEye Fixlt kit (IBIS, Netherlands). After sensor preparation, antibody competition analysis was performed using a classical sandwich assay. Recombinant FLT3-his ECD antigen (Sino Biological Inc) was diluted in PBS, 0.05% Tween 20, 200 nM Herceptin running buffer and injected at a 100 nM concentration, and captured by the conjugated array of anti-FLT3 antibodies. Next, individual injections of each of the FLT3 antibodies diluted to 100 nM in running buffer were performed to establish antibody competition patterns. Recombinant FLT3 ligand (100 nM) was included as an analyte to characterize ligand blocking antibodies. Data was analyzed by Epitope Binning 2.0 (Wasatch, USA).

Results

Figure 12:
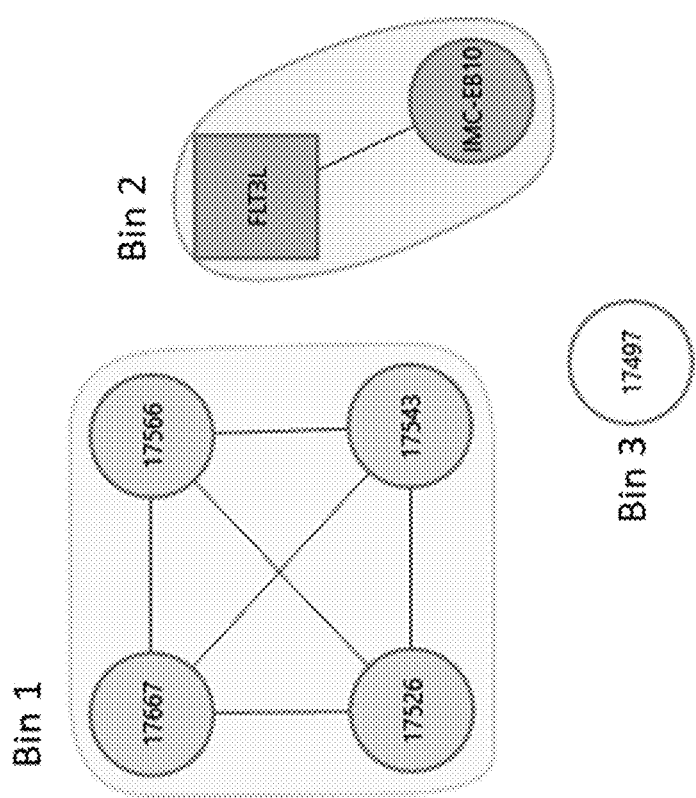
FIG. 12 is a schematic showing competition patterns and epitope bins for the indicated anti-FLT3 antibodies. Connecting black lines indicate cross-blocking activity. Circles represent antibodies tested in both directions, while squares represent testing in one direction. Antibodies are grouped according to competition patterns with other anti-FLT3 antibodies.

FIG. 12 shows a node plot of anti-FLT3 mAbs 17667, 17566, 17526, and 17543, the IMC-EB10 analogue, and the FLT3 ligand (FLT3L) as derived from the epitope binning analysis. The anti-FLT3 antibodies were distributed in three discrete groups, or bins. Bin 1 (light grey) included antibodies 17526, 17543, 17566, and 17667, which all cross-blocked each other indicating that these antibodies bind a similar epitope of the FLT3 extracellular domain. Bin 2 (grey) consisted of the IMC-EB10 analogue, which blocks FLT3L in agreement with published data (U.S. Patent Publication 2011/0091470). Bin 3 (white), consisted only of antibody 17497, showing that this antibody recognizes an epitope distinct from the other antibodies in the analysis.

In conclusion, none of the tested antibodies blocked FLT3L except the IMC-EB10 analogue. Antibodies 17526, 17543, 17566, and 17667 bind overlapping epitopes while 17497 binds a separate epitope.

Example 16. Epitope Mapping of Anti-FLT3 Antibodies by Mutagenesis and Surface Plasmon Resonance This example illustrates how the epitopes recognized by monoclonal anti-FLT3 antibodies 17566, 17526, 17667, 17543, and 17497 are distributed on the FLT3 extracellular domain (ECD). Linear and conformational epitopes were characterized by a mutagenesis approach and surface plasmon resonance (SPR).

Materials and Methods

The protein sequences of human and rat (*Rattus norvegicus*) FLT3 were downloaded from UniProt (Accession Nos. P36888 and A0A0G2JW59, respectively) and aligned. To map linear epitopes, Fc fusion proteins of domain 1 of human FLT3 ECD were generated having 10 amino acids sequentially exchanged by the corresponding rat FLT3 sequence in segments overlapping by 5 amino acids. Conformational epitopes were characterized by alanine-scanning mutagenesis of FLT3 domain 1.

The cDNA coding for human FLT3 domain 1 was synthesized and cloned into a vector containing CMV promoter and human Ig Fc sequence (residues P101-K330), resulting in fusion of Ig Fc to the C-terminus. Wild type (wt) and mutated human FLT3 domain 1 Fc fusion constructs were generated by standard gene synthesis techniques and proteins were expressed transiently in an ExpiCHO™ expression system. After harvesting, supernatants were tested for binding to anti-FLT3 Fabs by surface plasmon resonance (SPR) using Carterra LSA. An HC200M (Carterra, Inc) chip was functionalized by goat anti-human Ig Fc (Southern Biotech) using amine-coupling. The chip was activated by freshly prepared 0.4 M EDC, 0.1 M sulfo-NHS, and 0.1 M MES, pH 5.5 (1:1:1 v/v/v) for 5 min, coupled with 75 μg/mL anti-human Ig Fc in 10 mM sodium acetate, pH 4.5, for 10 min, and excess reactive esters were quenched for 3 min by injection of 1 M ethanolamine, pH 8.5. The instrument was primed in running buffer (PBS pH 7.4, 0.01% Tween-20, 0.5 mg/ml BSA). After priming and washing, FLT3 fusion proteins in culture supernatants were captured onto individual spots of the chip for 12 minutes as duplicates. Fab analytes were each prepared in running buffer. Kinetic analysis was performed by applying kinetic titration series of monomeric Fabs at increasing concentrations. Fab association was performed for 5 minutes and antigen dissociation was recorded for 5 minutes. After each cycle of Fab injections, the surface was regenerated by 0.45% $H_3PO_4$ for 2×20 s and washed for 5 min in running buffer. Binding responses were processed and analyzed using Carterra's KIT software tool. Processed data was fitted to a simple Langmuir 1:1 binding model for calculation of the on-rate ($k_{on}$ or $k_a$), off-rate ($k_{off}$ or $k_d$) and affinity ($K_D$) constants. Mutations generating inactive proteins common for all Fab fragments were deselected. To identify amino acids causing a significant loss of binding, a cutoff of at least a 5-fold decrease in binding affinity compared to wild type human FLT3 and/or having a z-score above 3 were used define the epitopes.

Results

The linear and conformational epitopes of anti-FLT3 antibodies 17566, 17526, 17667, 17543, and 17497 are shown in Table 8.

TABLE 8

Anti-FLT-3 Antibody Epitopes

| Antibody | Linear epitope | Contact Residues |
|---|---|---|
| 17566 | A78-A87 | A79, A80, V81, T157, R161 |
| 17526 | A78-A87 | A79, A80, V81, I89, T90, R161 |
| 17667 | A78-A87 | A79, V81 |
| 17543 | A78-A97 | A79, V81, V83, A87, I89, V125, T157 |
| 17497 | A138-S147 | N100, L104-V106, H109-S111, E140, L142, N151, T153 |

The extracellular domain of FLT3 consists of five immunoglobulin (Ig)-like domains (D1-D5). The anti-FLT3 antibodies in this example all bound FLT3 D1. As shown in Table 8, antibodies 17566, 17526, 17667, and 17543 bound similar epitopes while the mouse-cross reactive antibody, 17497, bound a separate epitope as predicted by epitope binning (Example 15).

Figure 13:
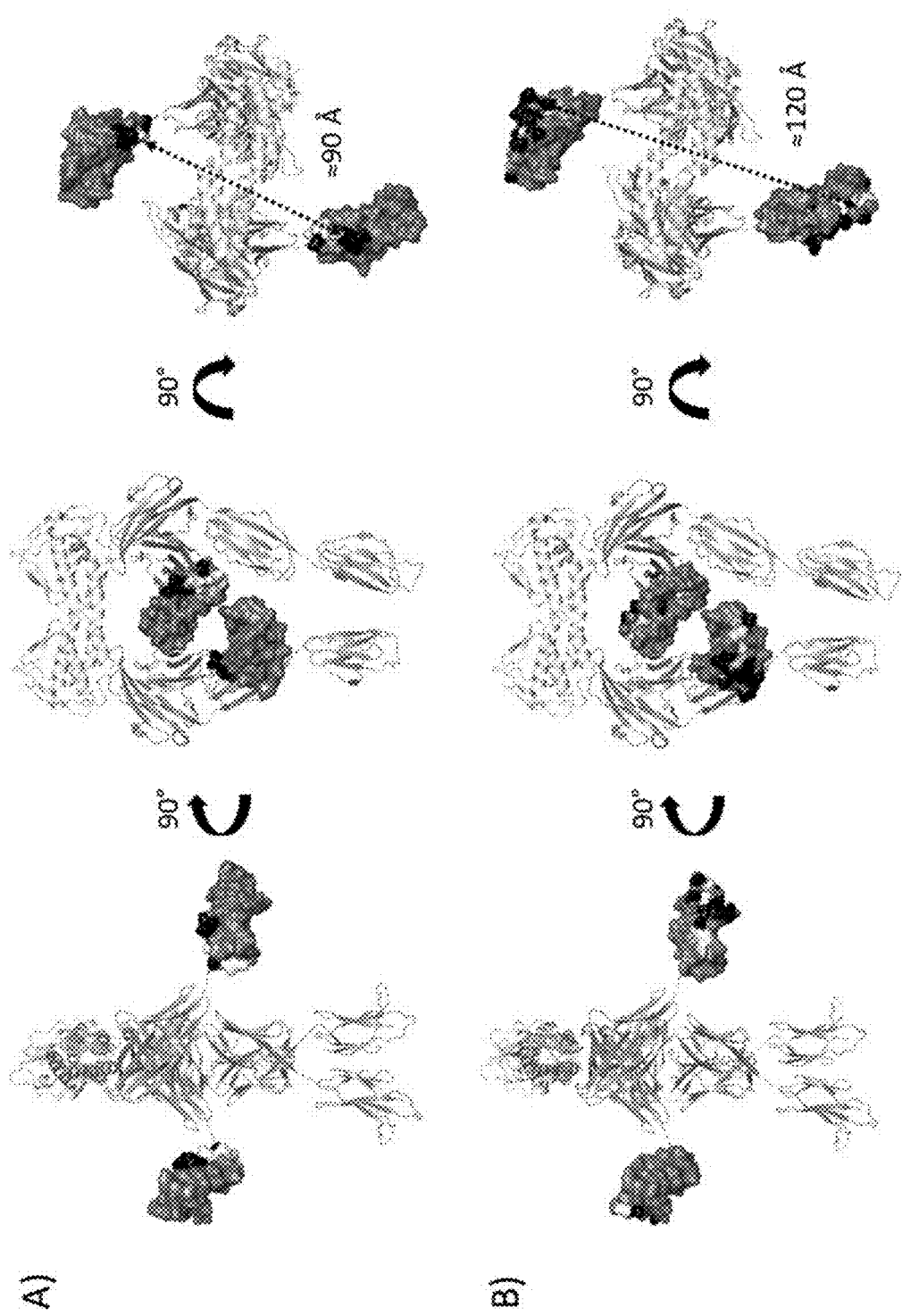
FIG. 13 is a series of structures showing the binding epitopes of antibodies 17566 (Panel A) and 17497 (Panel B) mapped onto the structure of the FLT3 ligand receptor complex (PDB entry: 3QS9). The two FLT3 receptors (light grey) and the FLT3 ligand (white) are represented as cartoon. Domain 1 of FLT3 is shown as a surface representation (dark grey). Linear epitopes are shown as white and contact residues as black. The structures are viewed in different orientations as indicated. Seen from the N-terminal top of the FLT3 receptors, the distances between the epitopes are approximately 90 Å (17566) and 120 Å (17497).

The epitopes were mapped onto the FLT3 ligand-receptor complex (PDB entry: 3QS9, FIG. 13). The crystal structure consists of two receptor molecules binding bivalently to the FLT3 ligand (FLT3L) with a binding interface at the tip of FLT3 D3. The complex forms an open ring-like structure in which the N-terminal D1 is highly flexible, having at least two different orientations around the linker region between D1 and D2, and no interactions with the rest of the protein complex (Verstrate et al., *Blood* (2011) 1:60-68).

The common section in the epitopes of 17566, 17526, 17667, and 17543 was located at the C-terminal end of D1 just before the start of D2. This shared section was located at the inner surface of D1 while the epitope of 17497 was located on the outer surface of D1 relative to FLT3L. The distance between the epitopes on each D1 in the ligand-receptor complex was approximately 90 Å to 120 Å for each of the epitopes (FIG. 13), which is within the optimal distance of an IgG molecule binding to two epitopes (Zhang et al., *Nature Communication* (2020) 11:3114 and Zhang et al., *Scientific Reports* (2015) 5:9803). Considering that D1 is highly flexible and can adapt to different orientations (Verstrate et al., supra) it is likely that antibodies binding these epitopes can dimerize FLT3 and activate receptor signaling independent of the FLT3 ligand In conclusion, the epitope mapping analysis showed that the epitopes of antibodies 17566, 17526, 17667, and 17543 share residues on the inner surface of FLT3 D1, while antibody 17497 bound a separate epitope on the outer surface of D1. The epitopes located on FLT3 D1 appear to be optimal for agonistic anti-FLT3 antibodies and receptor activation.

The invention claimed is:

1. An anti-FLT3 antibody or an antigen-binding portion thereof, wherein said antibody comprises the H-CDR1-3 amino acid sequences of SEQ ID NOs: 25-27, respectively, and the L-CDR1-3 amino acid sequences of SEQ ID NOs: 28-30, respectively.

2. The anti-FLT3 antibody or antigen-binding portion of claim 1, wherein said antibody comprises a heavy chain variable domain amino acid sequence and a light chain variable domain amino acid sequence that are at least 90% identical to
   a) SEQ ID NOs: 23 and 24, respectively; or
   b) SEQ ID NOs: 73 and 74, respectively.

3. The anti-FLT3 antibody or antigen-binding portion of claim 1, wherein said antibody comprises a heavy chain variable domain and a light chain variable domain comprising the amino acid sequences of
   a) SEQ ID NOs: 23 and 24, respectively; or
   b) SEQ ID NOs: 73 and 74, respectively.

4. The anti-FLT3 antibody of claim 1, wherein the antibody is an IgG1 and one or both of the heavy chain amino acid residues at positions 234 and 235 (Eu numbering) are mutated from Leu to Ala.

5. The anti-FLT3 antibody or antigen-binding portion of claim 1, wherein the antibody or antigen-binding portion has at least one property selected from:
   a) stimulates proliferation of EOL-1 cells in vitro;
   b) stimulates proliferation of OCI-AML5 cells in vitro;
   c) binds to human FLT3 with a $K_D$ of 20 nM or less;
   d) specifically binds to cynomolgus FLT3;
   e) specifically binds to mouse FLT3;
   f) does not block FLT3 ligand binding to human FLT3 in vitro;
   g) does not block binding of FLT3L-Fc to cell-displayed human, cynomolgus, or mouse FLT3 protein in vitro;
   h) stimulates proliferation of primary human CD34+ stem cells;
   i) stimulates differentiation of primary human CD34+ stem cells;
   j) induces dendritic cell mobilization in vivo in Balb/c mice; and
   k) induces dendritic cell mobilization in vivo in immunocompromised mice reconstituted with human CD34+ stem cells.

6. A pharmaceutical composition comprising the anti-FLT3 antibody or antigen-binding portion of claim 1 and a pharmaceutically acceptable excipient.

7. A bi-specific binding molecule comprising
   a) the antigen-binding portion of an anti-FLT3 antibody of claim 1, and
   b) the antigen-binding portion of a different FLT3 antibody or the antigen-binding portion of an antibody that does not bind to FLT3.

8. A method for increasing dendritic cell mobilization in a human patient in need thereof, comprising administering to said patient a therapeutically effective amount of the anti-FLT3 antibody or antigen-binding portion of claim 1.

9. The anti-FLT3 antibody or antigen-binding portion of claim 1, wherein said antibody comprises heavy and light chain variable domains comprising the amino acid sequences of SEQ ID NOs: 23 and 24, respectively.

10. An anti-FLT3 antibody that comprises:
    a) a heavy chain that comprises the heavy chain variable domain amino acid sequence of SEQ ID NO: 23 and the heavy chain constant region amino acid sequence of SEQ ID NO: 75 and a light chain that comprises the light chain variable domain amino acid sequence of SEQ ID NO: 24 and the light chain constant region amino acid sequence of SEQ ID NO: 76; or
    b) a heavy chain that comprises the heavy chain variable domain amino acid sequence of SEQ ID NO: 73 and the heavy chain constant region amino acid sequence of SEQ ID NO: 75 and a light chain that comprises the light chain variable domain amino acid sequence of SEQ ID NO: 74 and the light chain constant region amino acid sequence of SEQ ID NO: 76.

11. An anti-FLT3 antibody comprising a heavy chain that comprises the heavy chain variable domain amino acid sequence of SEQ ID NO: 23 and the heavy chain constant region amino acid sequence of SEQ ID NO: 75, and a light chain that comprises the light chain variable domain amino acid sequence of SEQ ID NO: 24 and the light chain constant region amino acid sequence of SEQ ID NO: 76.

12. A pharmaceutical composition comprising the anti-FLT3 antibody or antigen-binding portion of claim 11 and a pharmaceutically acceptable excipient.

13. A bi-specific binding molecule comprising
   a) the antigen-binding portion of an anti-FLT3 antibody of claim 11, and
   b) the antigen-binding portion of a different FLT3 antibody or the antigen-binding portion of an antibody that does not bind to FLT3.

14. A method for increasing dendritic cell mobilization in a human patient in need thereof, comprising administering to said patient a therapeutically effective amount of the anti-FLT3 antibody or antigen-binding portion of claim 11.

* * * * *

SEQUENCE LISTING

<160> NUMBER OF SEQ ID NOS: 79

<210> SEQ ID NO 1
<211> LENGTH: 372
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 1

```
caagtgacac tgaaggagtc cggcccagtg ctggtgaagc ccaccgagac actgaccctg      60
acatgcaccg tgtctggctt ctcctttaac aatgccagga tgggagtgaa ctggatcagg     120
cagccacctg gcaaggccct ggagtggctg gctcacatct tcagcaatga cgagaagtcc     180
tacagcacat ctctgaagag caggctgacc atctctaagg atatctccaa gagccaggtg     240
gtgctgacaa tgaccaacat ggaccccgtg gatacagcca cctactattg tgctagaatc     300
gtgggatacg gatctggatg gaggctgctg ggcgactatt ggggacaggg cacactggtg     360
accgtctcga gt                                                         372
```

<210> SEQ ID NO 2
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 2

```
gccatccaga tgacccagag ccccttccagc ctgtccgcct ccgtgggcga cagggtgacc     60
atcacatgcc gggcctctca gggcatcaca aacgatctgg ctggtacca gcagaagccc     120 ggcaaggctc ctaagctgct gatctatgcc gcttcttccc tgcaatctgg cgtgccatcc     180
aggttctctg gatccggaag cggaaccgac tttaccctga caatcagctc tctgcaacca     240
gaggacttcg ccacatacta ttgtctgcaa gattacaatt atccctggac ctttggccag     300
ggcacaaagg tggagatcaa g                                               321
```

<210> SEQ ID NO 3
<211> LENGTH: 124
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 3

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Phe Asn Asn Ala
            20                  25                  30

Arg Met Gly Val Asn Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Ile Ser Lys Ser Gln Val
65                  70                  75                  80

Val Leu Thr Met Thr Asn Met Asp Pro Val Asp Thr Ala Thr Tyr Tyr
                85                  90                  95
```

```
Cys Ala Arg Ile Val Gly Tyr Gly Ser Gly Trp Arg Leu Leu Gly Asp
                100                 105                 110

Tyr Trp Gly Gln Gly Thr Leu Val Thr Val Ser Ser
        115                 120

<210> SEQ ID NO 4
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 4

Ala Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Thr Asn Asp
            20                  25                  30

Leu Gly Trp Tyr Gln Gln Lys Pro Gly Lys Ala Pro Lys Leu Leu Ile
        35                  40                  45

Tyr Ala Ala Ser Ser Leu Gln Ser Gly Val Pro Ser Arg Phe Ser Gly
    50                  55                  60

Ser Gly Ser Gly Thr Asp Phe Thr Leu Thr Ile Ser Ser Leu Gln Pro
65                  70                  75                  80

Glu Asp Phe Ala Thr Tyr Tyr Cys Leu Gln Asp Tyr Asn Tyr Pro Trp
                85                  90                  95

Thr Phe Gly Gln Gly Thr Lys Val Glu Ile Lys
            100                 105

<210> SEQ ID NO 5
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 5

Gly Phe Ser Phe Asn Asn Ala Arg Met Gly
1               5                   10

<210> SEQ ID NO 6
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 6

Ile Phe Ser Asn Asp Glu Lys
1               5

<210> SEQ ID NO 7
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 7

Cys Ala Arg Ile Val Gly Tyr Gly Ser Gly Trp Arg Leu Leu Gly Asp
1               5                   10                  15
```

<210> SEQ ID NO 8
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 8

Gln Gly Ile Thr Asn Asp
1               5

<210> SEQ ID NO 9
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 9

Ala Ala Ser
1

<210> SEQ ID NO 10
<211> LENGTH: 11
<212> TYPE: PRT
<213> ORGANISM: Artificial Sequence
<220> FEATURE:
<223> OTHER INFORMATION: Description of Artificial Sequence: Synthetic peptide

<400> SEQUENCE: 10

Cys Leu Gln Asp Tyr Asn Tyr Pro Trp Thr Phe
1               5                   10

<210> SEQ ID NO 11
<211> LENGTH: 369
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 11

```
caagtgacac tgaaggagtc tggcccagtg ctggtgaagc ccaccgagac actgaccctg      60
acatgcacca tctctggctt ctccctgggc aacgccagga tgggcgtgtc ctggatcagg     120
cagccacctg gcaaggccct ggagtggctg gctcacatct ttagcaatga cgagaagtcc     180
tacagcacct ctctgaagag cagactgaca atctctaagg ataccctcca gagccaggtg     240
gtgctgacaa tgaccaacat ggaccctgtg atacagcca cctactattg tgctcgcatc     300
gtgggctacg tggactggct gctgccattc gattattggg gccagggcac actggtgacc     360
gtctcgagt                                                             369
```

<210> SEQ ID NO 12
<211> LENGTH: 324
<212> TYPE: DNA
<213> ORGANISM: Artificial Sequence
<220> FEATURE:
<223> OTHER INFORMATION: Description of Artificial Sequence: Synthetic polynucleotide -continued

```
<400> SEQUENCE: 12
gagatcgtga tgacccagtc tccagccaca ctgagcgtgt ctccaggaga gagggccacc      60
ctgtcctgca gagcttccca gagcgtgtcc agcaacctgg cttggtacca gcagaagcca     120
ggacaggctc ctaggctgct gatctatggc gccagcacca gagctacagg aatccctgct     180
cgcttctctg gatccggaag cggcacagag tttaccctga caatctcttc cctgcaatct     240
gaggacttcg ccgtgtacta ttgtcagcaa tacaatcact ggccaatgta tacctttggc     300
cagggcacaa agctggagat caag                                             324

<210> SEQ ID NO 13
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 13

Gln Val Thr Leu Lys Glu Ser Gly Pro Val Leu Val Lys Pro Thr Glu
1               5                   10                  15

Thr Leu Thr Leu Thr Cys Thr Ile Ser Gly Phe Ser Leu Gly Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Val Gly Tyr Val Asp Trp Leu Leu Pro Phe Asp Tyr
            100                 105                 110

Trp Gly Gln Gly Thr Leu Val Thr Val Ser Ser
        115                 120

<210> SEQ ID NO 14
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 14

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn His Trp Pro Met
                85                  90                  95

Tyr Thr Phe Gly Gln Gly Thr Lys Leu Glu Ile Lys
```

<210> SEQ ID NO 15
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 15

Gly Phe Ser Leu Gly Asn Ala Arg Met Gly
1               5                   10

<210> SEQ ID NO 16
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 16

Ile Phe Ser Asn Asp Glu Lys
1               5

<210> SEQ ID NO 17
<211> LENGTH: 17
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 17

Cys Ala Arg Ile Val Gly Tyr Val Asp Trp Leu Leu Pro Phe Asp Tyr
1               5                   10                  15

Trp

<210> SEQ ID NO 18
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 18

Gln Ser Val Ser Ser Asn
1               5

<210> SEQ ID NO 19
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 19

Gly Ala Ser
1

<210> SEQ ID NO 20
<211> LENGTH: 12
<212> TYPE: PRT
<213> ORGANISM: Artificial Sequence

```
<220> FEATURE:
<223> OTHER INFORMATION: Description of Artificial Sequence: Synthetic
      peptide

<400> SEQUENCE: 20

Cys Gln Gln Tyr Asn His Trp Pro Met Tyr Thr Phe
1               5                   10

<210> SEQ ID NO 21
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 21
caagtgacac tgaaggagtc tggcccagtg ctggtgaagc ccaccgagac actgaccctg      60
acatgcaccg tgtccggctt ctccctgagc aacgccagga tgggcgtgag ctggatcagg     120
cagccacctg gcaaggccct ggagtggctg gctcacatct tttccaatga cgagagatct     180
tactccccca gcctgaagag ccgcctgaca atctctaagg caccctctaa gtcccaggtg     240
gtgctgacaa tgaccaacat ggaccctgtg atacagcca cctactattg tgctaggatc      300
gtgggctacg tggactggct gctgccattc gattattggg ccagggcac actggtgacc      360 gtctcgagt                                                              369

<210> SEQ ID NO 22
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 22
gagatcgtga tgacccagtc tccagccaca ctgagcgtgt ctccaggaga gagggccacc      60
ctgtcctgca gcttccca gagcgtgtcc agcaacctgg cttggtacca gcagaagcca      120
ggacaggctc ctaggctgct gatctatggc gccagcacca gagctacagg aatccctgct     180
cgcttctctg gatccggaag cggcacagag tttaccctga caatctcttc cctgcaatct     240
gaggacttcg ccgtgtacta ttgtcagcag tacaacaatt ggccaatgta cacctttggc     300
cagggcacaa agctggagat caag                                            324

<210> SEQ ID NO 23
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 23

Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
                20                  25                  30

Arg Met Gly Val Ser Trp Ile Arg Gln Pro Pro Gly Lys Ala Leu Glu
            35                  40                  45

Trp Leu Ala His Ile Phe Ser Asn Asp Glu Arg Ser Tyr Ser Pro Ser
        50                  55                  60
```

```
Leu Lys Ser Arg Leu Thr Ile Ser Lys Gly Thr Ser Lys Ser Gln Val
 65                  70                  75                  80

Val Leu Thr Met Thr Asn Met Asp Pro Val Asp Thr Ala Thr Tyr Tyr
                 85                  90                  95

Cys Ala Arg Ile Val Gly Tyr Val Asp Trp Leu Leu Pro Phe Asp Tyr
            100                 105                 110

Trp Gly Gln Gly Thr Leu Val Thr Val Ser Ser
        115                 120

<210> SEQ ID NO 24
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 24

Glu Ile Val Met Thr Gln Ser Pro Ala Thr Leu Ser Val Ser Pro Gly
1               5                   10                  15

Glu Arg Ala Thr Leu Ser Cys Arg Ala Ser Gln Ser Val Ser Ser Asn
            20                  25                  30

Leu Ala Trp Tyr Gln Gln Lys Pro Gly Gln Ala Pro Arg Leu Leu Ile
        35                  40                  45

Tyr Gly Ala Ser Thr Arg Ala Thr Gly Ile Pro Ala Arg Phe Ser Gly
    50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Met
                85                  90                  95

Tyr Thr Phe Gly Gln Gly Thr Lys Leu Glu Ile Lys
            100                 105

<210> SEQ ID NO 25
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 25

Gly Phe Ser Leu Ser Asn Ala Arg Met Gly
1               5                   10

<210> SEQ ID NO 26
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 26

Ile Phe Ser Asn Asp Glu Arg
1               5

<210> SEQ ID NO 27
<211> LENGTH: 17
<212> TYPE: PRT
<213> ORGANISM: Artificial Sequence
<220> FEATURE:
```

```
<223> OTHER INFORMATION: Description of Artificial Sequence: Synthetic
      peptide

<400> SEQUENCE: 27

Cys Ala Arg Ile Val Gly Tyr Val Asp Trp Leu Leu Pro Phe Asp Tyr
1               5                   10                  15

Trp

<210> SEQ ID NO 28
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 28

Gln Ser Val Ser Ser Asn
1               5

<210> SEQ ID NO 29
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 29

Gly Ala Ser
1

<210> SEQ ID NO 30
<211> LENGTH: 12
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 30

Cys Gln Gln Tyr Asn Asn Trp Pro Met Tyr Thr Phe
1               5                   10

<210> SEQ ID NO 31
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 31
caagtgcagc tgcaggagtc cggaccagga ctggtgaagc cttctcagac cctgtccctg      60
acctgcacag tgagcggagg atctatctcc agcggaggat actattggtc ctggatcaga     120
cagcacccag gcaagggcct ggagtggatc ggctacatct actatagcgg caggacaaac     180
tataatccct ccctgaagag ccgggtgacc atcagcgagg acacatctaa gaaccagttc     240
tctctgaagg tgtcttccgt gaccgccgct gatacagccg tgtactattg tgctcgcgac     300
caggatggct ccggctggta ctttgactat tggggccagg cgcccctggt gaccgtctcg     360
agt                                                                   363

<210> SEQ ID NO 32
```

<211> LENGTH: 318
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 32

```
gagatcgtgc tgacccagtc cccagccaca ctgtctctgt cccccggaga gagggccacc      60
ctgagctgca gggcctccca gtccgtgtcc tcctacctgg cctggtatca gcagaagccc     120
ggccaggctc ctaggctgct gatctacgac gccagcaaca gagctaccgg aatccctgct     180
cgcttctccg gaagcggatc tggcacagac tttaccctga caatcaggtc tctggagcca     240
gaggatttcg ccgtgtacta ttgtcagcag agatccaatt ggtggacctt tggccagggc     300
acaaaggtgg agatcaag                                                   318
```

<210> SEQ ID NO 33
<211> LENGTH: 121
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 33

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
        35                  40                  45

Trp Ile Gly Tyr Ile Tyr Tyr Ser Gly Arg Thr Asn Tyr Asn Pro Ser
    50                  55                  60

Leu Lys Ser Arg Val Thr Ile Ser Glu Asp Thr Ser Lys Asn Gln Phe
65                  70                  75                  80

Ser Leu Lys Val Ser Ser Val Thr Ala Ala Asp Thr Ala Val Tyr Tyr
                85                  90                  95

Cys Ala Arg Asp Gln Asp Gly Ser Gly Trp Tyr Phe Asp Tyr Trp Gly
            100                 105                 110

Gln Gly Ala Leu Val Thr Val Ser Ser
        115                 120

<210> SEQ ID NO 34
<211> LENGTH: 106
<212> TYPE: PRT
<213> ORGANISM: Artificial Sequence
<220> FEATURE:
<223> OTHER INFORMATION: Description of Artificial Sequence: Synthetic polypeptide

<400> SEQUENCE: 34

Glu Ile Val Leu Thr Gln Ser Pro Ala Thr Leu Ser Leu Ser Pro Gly
1               5                   10                  15

Glu Arg Ala Thr Leu Ser Cys Arg Ala Ser Gln Ser Val Ser Ser Tyr
            20                  25                  30

Leu Ala Trp Tyr Gln Gln Lys Pro Gly Gln Ala Pro Arg Leu Leu Ile
        35                  40                  45

Tyr Asp Ala Ser Asn Arg Ala Thr Gly Ile Pro Ala Arg Phe Ser Gly
    50                  55                  60

```
Ser Gly Ser Gly Thr Asp Phe Thr Leu Thr Ile Arg Ser Leu Glu Pro
 65                  70                  75                  80

Glu Asp Phe Ala Val Tyr Tyr Cys Gln Gln Arg Ser Asn Trp Trp Thr
                 85                  90                  95

Phe Gly Gln Gly Thr Lys Val Glu Ile Lys
            100                 105
```

<210> SEQ ID NO 35
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 35

```
Gly Gly Ser Ile Ser Ser Gly Gly Tyr Tyr
1               5                   10
```

<210> SEQ ID NO 36
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 36

```
Ile Tyr Tyr Ser Gly Arg Thr
1               5
```

<210> SEQ ID NO 37
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 37

```
Cys Ala Arg Asp Gln Asp Gly Ser Gly Trp Tyr Phe Asp Tyr Trp
1               5                   10                  15
```

<210> SEQ ID NO 38
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 38

```
Gln Ser Val Ser Ser Tyr
1               5
```

<210> SEQ ID NO 39
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 39

```
Asp Ala Ser
1
```

<210> SEQ ID NO 40
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 40

Cys Gln Gln Arg Ser Asn Trp Trp Thr Phe
1               5                   10

<210> SEQ ID NO 41
<211> LENGTH: 363
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 41
caagtgcagc tgcaggagag cggaccagga ctggtgaagc ctagccagac cctgtctctg      60
acctgcactg tgtccggagg aagcatctcc agcggaggat actattggtc ttggatcagg     120
cagcacccag gcaagggcct ggagtggatc ggctacatct actatagcgg ctctacatac     180
tataacccct ctctgaagtc ccgggtgacc atctccgtgg acacaagcaa gaatcagttc     240
tctctgaagc tgtcttccgt gaccgccgct gatacagccg tgtactattg tctagggac     300 ctggatggct ccggctggta ctttgactat ggggccagg gcaccctggt gacagtctcg     360
agt                                                                  363

<210> SEQ ID NO 42
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 42
gagatcgtgc tgacccagtc tcctgccaca ctgagcctgt ctccaggaga gagggccacc      60
ctgtcctgca gcttccca gagcgtgtcc agctacctgg cctggtatca gcaaaagcca     120
ggccaggctc ccaggctgct gatctacgac gccagcaaca gagctaccgg aatcccagct     180
cgcttctctg gatccggaag cggcacagac tttaccctga caatctcttc cctggagcct     240
gaggatttcg ccgtgtacta ttgtcagcag agatctaatt ggccccctct gacctttggc     300
ggcggcacaa aggtggagat caag                                           324

<210> SEQ ID NO 43
<211> LENGTH: 121
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 43

Gln Val Gln Leu Gln Glu Ser Gly Pro Gly Leu Val Lys Pro Ser Gln
1               5                   10                  15

Thr Leu Ser Leu Thr Cys Thr Val Ser Gly Gly Ser Ile Ser Ser Gly
            20                  25                  30

Gly Tyr Tyr Trp Ser Trp Ile Arg Gln His Pro Gly Lys Gly Leu Glu
            35                  40                  45

Trp Ile Gly Tyr Ile Tyr Tyr Ser Gly Ser Thr Tyr Tyr Asn Pro Ser
 50                  55                  60

Leu Lys Ser Arg Val Thr Ile Ser Val Asp Thr Ser Lys Asn Gln Phe
 65                  70                  75                  80

Ser Leu Lys Leu Ser Ser Val Thr Ala Ala Asp Thr Ala Val Tyr Tyr
                 85                  90                  95

Cys Ala Arg Asp Leu Asp Gly Ser Gly Trp Tyr Phe Asp Tyr Trp Gly
            100                 105                 110

Gln Gly Thr Leu Val Thr Val Ser Ser
        115                 120

<210> SEQ ID NO 44
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 44

Glu Ile Val Leu Thr Gln Ser Pro Ala Thr Leu Ser Leu Ser Pro Gly
 1               5                  10                  15

Glu Arg Ala Thr Leu Ser Cys Arg Ala Ser Gln Ser Val Ser Ser Tyr
             20                  25                  30

Leu Ala Trp Tyr Gln Gln Lys Pro Gly Gln Ala Pro Arg Leu Leu Ile
            35                  40                  45

Tyr Asp Ala Ser Asn Arg Ala Thr Gly Ile Pro Ala Arg Phe Ser Gly
 50                  55                  60

Ser Gly Ser Gly Thr Asp Phe Thr Leu Thr Ile Ser Ser Leu Glu Pro
 65                  70                  75                  80

Glu Asp Phe Ala Val Tyr Tyr Cys Gln Gln Arg Ser Asn Trp Pro Pro
                 85                  90                  95

Leu Thr Phe Gly Gly Gly Thr Lys Val Glu Ile Lys
            100                 105

<210> SEQ ID NO 45
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 45

Gly Gly Ser Ile Ser Ser Gly Gly Tyr Tyr
 1               5                  10

<210> SEQ ID NO 46
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 46

Ile Tyr Tyr Ser Gly Ser Thr
 1               5

<210> SEQ ID NO 47
<211> LENGTH: 15
<212> TYPE: PRT
<213> ORGANISM: Artificial Sequence
<220> FEATURE:
<223> OTHER INFORMATION: Description of Artificial Sequence: Synthetic peptide

<400> SEQUENCE: 47

Cys Ala Arg Asp Leu Asp Gly Ser Gly Trp Tyr Phe Asp Tyr Trp
1               5                   10                  15

<210> SEQ ID NO 48
<211> LENGTH: 6
<212> TYPE: PRT
<213> ORGANISM: Artificial Sequence
<220> FEATURE:
<223> OTHER INFORMATION: Description of Artificial Sequence: Synthetic peptide

<400> SEQUENCE: 48

Gln Ser Val Ser Ser Tyr
1               5

<210> SEQ ID NO 49
<211> LENGTH: 3
<212> TYPE: PRT
<213> ORGANISM: Artificial Sequence
<220> FEATURE:
<223> OTHER INFORMATION: Description of Artificial Sequence: Synthetic peptide

<400> SEQUENCE: 49

Asp Ala Ser
1

<210> SEQ ID NO 50
<211> LENGTH: 12
<212> TYPE: PRT
<213> ORGANISM: Artificial Sequence
<220> FEATURE:
<223> OTHER INFORMATION: Description of Artificial Sequence: Synthetic peptide

<400> SEQUENCE: 50

Cys Gln Gln Arg Ser Asn Trp Pro Pro Leu Thr Phe
1               5                   10

<210> SEQ ID NO 51
<211> LENGTH: 381
<212> TYPE: DNA
<213> ORGANISM: Artificial Sequence
<220> FEATURE:
<223> OTHER INFORMATION: Description of Artificial Sequence: Synthetic polynucleotide

<400> SEQUENCE: 51
caagtgaccc tgaaggagtc cggcccagtg ctggtgaagc ccaccgagac actgaccctg      60
acatgcaccg tgtctggctt ctccctgatc aacgccagaa tgggagtgac atggatcagg     120
cagccacctg gcaaggccct ggagtggctg gctcacatct ttagcaatga cgagaagtcc     180
tacagcacct ctctgaagag caggctgaca atctctaagg atacctccaa gagccaggtg     240
gtgctgacaa tgaccaacat ggaccctgtg gatacagcca cctactattg tgctaggatc     300
ccaggctatt ctcggggctg ggactactat tactatggca tggacgtgtg gggccagggc     360
acaatggtga ccgtctcgag t                                               381

<210> SEQ ID NO 52
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 52

```
gacatccaga tgacacagtc cccttccagc ctgagcgcct ctgtgggcga cagggtgacc    60
atcacatgcc gggcctccca gggcatcaga acgatctggg ctggtacca gcagaagccc   120 ggcaaggccc ctaagcgcct gatctatgct gcttccaccc tgcagagcgg agtgccatct   180
aggttctccg gcagcggctc tggcacagag tttaccctga caatctcttc cctgcagcca   240
gaggatttcg ctacctacta ttgtctgcag cacaattctt accctggac ctttggccag    300 ggcacaaagg tggagatcaa g                                              321
```

<210> SEQ ID NO 53
<211> LENGTH: 127
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 53

```
Gln Val Thr Leu Lys Glu Ser Gly Pro Val Leu Val Lys Pro Thr Glu
1               5                   10                  15

Thr Leu Thr Leu Thr Cys Thr Val Ser Gly Phe Ser Leu Ile Asn Ala
            20                  25                  30

Arg Met Gly Val Thr Trp Ile Arg Gln Pro Pro Gly Lys Ala Leu Glu
        35                  40                  45

Trp Leu Ala His Ile Phe Ser Asn Asp Glu Lys Ser Tyr Ser Thr Ser
    50                  55                  60

Leu Lys Ser Arg Leu Thr Ile Ser Lys Asp Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Pro Gly Tyr Ser Arg Gly Trp Asp Tyr Tyr Tyr Tyr
            100                 105                 110

Gly Met Asp Val Trp Gly Gln Gly Thr Met Val Thr Val Ser Ser
        115                 120                 125
```

<210> SEQ ID NO 54
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 54

```
Asp Ile Gln Met Thr Gln Ser Pro Ser Ser Leu Ser Ala Ser Val Gly
1               5                   10                  15

Asp Arg Val Thr Ile Thr Cys Arg Ala Ser Gln Gly Ile Arg Asn Asp
            20                  25                  30

Leu Gly Trp Tyr Gln Gln Lys Pro Gly Lys Ala Pro Lys Arg Leu Ile
        35                  40                  45
```

```
Tyr Ala Ala Ser Thr Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
 65                  70                  75                  80

Glu Asp Phe Ala Thr Tyr Tyr Cys Leu Gln His Asn Ser Tyr Pro Trp
                 85                  90                  95

Thr Phe Gly Gln Gly Thr Lys Val Glu Ile Lys
                100                 105

<210> SEQ ID NO 55
<211> LENGTH: 10
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 55

Gly Phe Ser Leu Ile Asn Ala Arg Met Gly
 1               5                  10

<210> SEQ ID NO 56
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 56

Ile Phe Ser Asn Asp Glu Lys
 1               5

<210> SEQ ID NO 57
<211> LENGTH: 21
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 57

Cys Ala Arg Ile Pro Gly Tyr Ser Arg Gly Trp Asp Tyr Tyr Tyr
 1               5                  10                  15

Gly Met Asp Val Trp
                20

<210> SEQ ID NO 58
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 58

Gln Gly Ile Arg Asn Asp
 1               5

<210> SEQ ID NO 59
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide
```

<400> SEQUENCE: 59

Ala Ala Ser
1

<210> SEQ ID NO 60
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 60

Cys Leu Gln His Asn Ser Tyr Pro Trp Thr Phe
1               5                   10

<210> SEQ ID NO 61
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 61
caagtgcagc tgcaggagtc tggaccagga ctggtgaagc catctggcac cctgtccctg      60
acatgcgccg tgagcggagg atctatctcc agcaccaact ggtggtcctg ggtgagacag     120
ccacctggca agggactgga gtggatcggc gagatcagcc acaggggctc taccaactac     180
aatccttccc tgaagagccg ggtgacaatc tccgtggaca agagcaagaa tcagttctcc     240
ctgaagctgt cttccgtgac cgccgctgac acagccgtgt actattgtgc tcgcgatcca     300
gagatgaccc tgtactatta ctatggcatg gacgtgtggg gccagggcac cacagtgaca     360
gtctcgagt                                                             369

<210> SEQ ID NO 62
<211> LENGTH: 321
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 62
gacatccaga tgacccagag ccctcccagc ctgtccgcca gcgtgggcga cagagtgacc      60
atcacatgca gggcttctcg gggcatcaga aacgatctgg gctggtacca gcagaagccc     120
ggcaaggccc ctaagcgcct gatctatgcc gcttcttccc tgcaatctgg cgtgccatcc     180
agattctctg gatccggaag cggaaccgag tttaccctga caatcagctc tctgcagcca     240
gaggatttcg ctacatacta ttgtctgcag cacaattcct accccctgac ctttggcggc     300
ggcacaaagg tggagatcaa g                                               321

<210> SEQ ID NO 63
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 63

Gln Val Gln Leu Gln Glu Ser Gly Pro Gly Leu Val Lys Pro Ser Gly
1               5                   10                  15

Thr Leu Ser Leu Thr Cys Ala Val Ser Gly Gly Ser Ile Ser Ser Thr
            20                  25                  30

Asn Trp Trp Ser Trp Val Arg Gln Pro Pro Gly Lys Gly Leu Glu Trp
            35                  40                  45

Ile Gly Glu Ile Ser His Arg Gly Ser Thr Asn Tyr Asn Pro Ser Leu
        50                  55                  60

Lys Ser Arg Val Thr Ile Ser Val Asp Lys Ser Lys Asn Gln Phe Ser
65                  70                  75                  80

Leu Lys Leu Ser Ser Val Thr Ala Ala Asp Thr Ala Val Tyr Tyr Cys
                85                  90                  95

Ala Arg Asp Pro Glu Met Thr Leu Tyr Tyr Tyr Gly Met Asp Val
                100                 105                 110

Trp Gly Gln Gly Thr Thr Val Thr Val Ser Ser
        115                 120

<210> SEQ ID NO 64
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 64

Asp Ile Gln Met Thr Gln Ser Pro Ser Ser Leu Ser Ala Ser Val Gly
1               5                   10                  15

Asp Arg Val Thr Ile Thr Cys Arg Ala Ser Arg Gly Ile Arg Asn Asp
            20                  25                  30

Leu Gly Trp Tyr Gln Gln Lys Pro Gly Lys Ala Pro Lys Arg Leu Ile
            35                  40                  45

Tyr Ala Ala Ser Ser Leu Gln Ser Gly Val Pro Ser Arg Phe Ser Gly
        50                  55                  60

Ser Gly Ser Gly Thr Glu Phe Thr Leu Thr Ile Ser Ser Leu Gln Pro
65                  70                  75                  80

Glu Asp Phe Ala Thr Tyr Tyr Cys Leu Gln His Asn Ser Tyr Pro Leu
                85                  90                  95

Thr Phe Gly Gly Gly Thr Lys Val Glu Ile Lys
                100                 105

<210> SEQ ID NO 65
<211> LENGTH: 9
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 65

Gly Gly Ser Ile Ser Ser Thr Asn Trp
1               5

<210> SEQ ID NO 66
<211> LENGTH: 7
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 66

Ile Ser His Arg Gly Ser Thr
1               5

<210> SEQ ID NO 67
<211> LENGTH: 18
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 67

Cys Ala Arg Asp Pro Glu Met Thr Leu Tyr Tyr Tyr Gly Met Asp
1               5                   10                  15

Val Trp

<210> SEQ ID NO 68
<211> LENGTH: 6
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 68

Arg Gly Ile Arg Asn Asp
1               5

<210> SEQ ID NO 69
<211> LENGTH: 3
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 69

Ala Ala Ser
1

<210> SEQ ID NO 70
<211> LENGTH: 11
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 70

Cys Leu Gln His Asn Ser Tyr Pro Leu Thr Phe
1               5                   10

<210> SEQ ID NO 71
<211> LENGTH: 369
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 71
caggtgcagc tacaggagtc tggtcctgtg ctggtgaaac ccacagagac cctcacgctg      60
acctgcaccg tctctgggtt ctcactcagc aatgctagaa tgggtgttag ctggatccgt     120
cagcccccag ggaaggccct ggagtggctt gcacacattt tttcaaatga cgaaagatcc     180

```
tacagtccat ctctgaagag caggctcacc atctccaagg gcacctccaa aagccaggtg    240
gtccttacca tgaccaacat ggaccctgtg acacagcca catattactg tgcacggata    300
gtaggatatg ttgactggtt attacccttt gactactggg gccagggaac cctggtcacg    360
gtctcgagt                                                             369
```

<210> SEQ ID NO 72
<211> LENGTH: 324
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 72

```
gaaacgacac tcacgcagtc tccagccacc ctgtctgtgt ctccagggga aagagccacc    60
ctctcctgca gggccagtca gagcgttagc agcaacttag cctggtacca gcagaaacct   120
ggccaggctc ccaggctcct catctatggt gcatccacca gggccactgg tatcccagcc   180
aggttcagtg gcagtgggtc tgggacagag ttcactctca ccatcagcag cctgcagtct   240
gaagattttg cagtttatta ctgtcagcag tataataact ggcccatgta cacttttggc   300
caggggacca agctggagat taag                                           324
```

<210> SEQ ID NO 73
<211> LENGTH: 123
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 73

```
Gln Val Gln Leu Gln Glu Ser Gly Pro Val Leu Val Lys Pro Thr Glu
1               5                   10                  15

Thr Leu Thr Leu Thr Cys Thr Val Ser Gly Phe Ser Leu Ser Asn Ala
            20                  25                  30

Arg Met Gly Val Ser Trp Ile Arg Gln Pro Pro Gly Lys Ala Leu Glu
        35                  40                  45

Trp Leu Ala His Ile Phe Ser Asn Asp Glu Arg Ser Tyr Ser Pro Ser
    50                  55                  60

Leu Lys Ser Arg Leu Thr Ile Ser Lys Gly Thr Ser Lys Ser Gln Val
65                  70                  75                  80

Val Leu Thr Met Thr Asn Met Asp Pro Val Asp Thr Ala Thr Tyr Tyr
                85                  90                  95

Cys Ala Arg Ile Val Gly Tyr Val Asp Trp Leu Leu Pro Phe Asp Tyr
            100                 105                 110

Trp Gly Gln Gly Thr Leu Val Thr Val Ser Ser
        115                 120
```

<210> SEQ ID NO 74
<211> LENGTH: 108
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 74

```
Glu Thr Thr Leu Thr Gln Ser Pro Ala Thr Leu Ser Val Ser Pro Gly
```

```
                1               5                  10                  15
Glu Arg Ala Thr Leu Ser Cys Arg Ala Ser Gln Ser Val Ser Ser Asn
                20                  25                  30

Leu Ala Trp Tyr Gln Gln Lys Pro Gly Gln Ala Pro Arg Leu Leu Ile
                35                  40                  45

Tyr Gly Ala Ser Thr Arg Ala Thr Gly Ile Pro Ala Arg Phe Ser Gly
                50                  55                  60

Ser Gly Ser Gly Thr Glu Phe Thr Leu Thr Ile Ser Ser Leu Gln Ser
65                  70                  75                  80

Glu Asp Phe Ala Val Tyr Tyr Cys Gln Gln Tyr Asn Asn Trp Pro Met
                    85                  90                  95

Tyr Thr Phe Gly Gln Gly Thr Lys Leu Glu Ile Lys
                    100                 105

<210> SEQ ID NO 75
<211> LENGTH: 330
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 75

Ala Ser Thr Lys Gly Pro Ser Val Phe Pro Leu Ala Pro Ser Ser Lys
1               5                   10                  15

Ser Thr Ser Gly Gly Thr Ala Ala Leu Gly Cys Leu Val Lys Asp Tyr
                20                  25                  30

Phe Pro Glu Pro Val Thr Val Ser Trp Asn Ser Gly Ala Leu Thr Ser
                35                  40                  45

Gly Val His Thr Phe Pro Ala Val Leu Gln Ser Ser Gly Leu Tyr Ser
                50                  55                  60

Leu Ser Ser Val Val Thr Val Pro Ser Ser Ser Leu Gly Thr Gln Thr
65                  70                  75                  80

Tyr Ile Cys Asn Val Asn His Lys Pro Ser Asn Thr Lys Val Asp Lys
                    85                  90                  95

Arg Val Glu Pro Lys Ser Cys Asp Lys Thr His Thr Cys Pro Pro Cys
                100                 105                 110

Pro Ala Pro Glu Ala Ala Gly Gly Pro Ser Val Phe Leu Phe Pro Pro
                115                 120                 125

Lys Pro Lys Asp Thr Leu Met Ile Ser Arg Thr Pro Glu Val Thr Cys
        130                 135                 140

Val Val Val Asp Val Ser His Glu Asp Pro Glu Val Lys Phe Asn Trp
145                 150                 155                 160

Tyr Val Asp Gly Val Glu Val His Asn Ala Lys Thr Lys Pro Arg Glu
                    165                 170                 175

Glu Gln Tyr Asn Ser Thr Tyr Arg Val Val Ser Val Leu Thr Val Leu
                180                 185                 190

His Gln Asp Trp Leu Asn Gly Lys Glu Tyr Lys Cys Lys Val Ser Asn
            195                 200                 205

Lys Ala Leu Pro Ala Pro Ile Glu Lys Thr Ile Ser Lys Ala Lys Gly
        210                 215                 220

Gln Pro Arg Glu Pro Gln Val Tyr Thr Leu Pro Pro Ser Arg Glu Glu
225                 230                 235                 240

Met Thr Lys Asn Gln Val Ser Leu Thr Cys Leu Val Lys Gly Phe Tyr
                    245                 250                 255
```

```
Pro Ser Asp Ile Ala Val Glu Trp Glu Ser Asn Gly Gln Pro Glu Asn
            260                 265                 270

Asn Tyr Lys Thr Thr Pro Pro Val Leu Asp Ser Asp Gly Ser Phe Phe
        275                 280                 285

Leu Tyr Ser Lys Leu Thr Val Asp Lys Ser Arg Trp Gln Gln Gly Asn
    290                 295                 300

Val Phe Ser Cys Ser Val Met His Glu Ala Leu His Asn His Tyr Thr
305                 310                 315                 320

Gln Lys Ser Leu Ser Leu Ser Pro Gly Lys
                325                 330

<210> SEQ ID NO 76
<211> LENGTH: 107
<212> TYPE: PRT
<213> ORGANISM: Artificial Sequence
<220> FEATURE:
<223> OTHER INFORMATION: Description of Artificial Sequence: Synthetic
      polypeptide

<400> SEQUENCE: 76

Arg Thr Val Ala Ala Pro Ser Val Phe Ile Phe Pro Pro Ser Asp Glu
1               5                   10                  15

Gln Leu Lys Ser Gly Thr Ala Ser Val Val Cys Leu Leu Asn Asn Phe
            20                  25                  30

Tyr Pro Arg Glu Ala Lys Val Gln Trp Lys Val Asp Asn Ala Leu Gln
        35                  40                  45

Ser Gly Asn Ser Gln Glu Ser Val Thr Glu Gln Asp Ser Lys Asp Ser
    50                  55                  60

Thr Tyr Ser Leu Ser Ser Thr Leu Thr Leu Ser Lys Ala Asp Tyr Glu
65                  70                  75                  80

Lys His Lys Val Tyr Ala Cys Glu Val Thr His Gln Gly Leu Ser Ser
                85                  90                  95

Pro Val Thr Lys Ser Phe Asn Arg Gly Glu Cys
            100                 105

<210> SEQ ID NO 77
<211> LENGTH: 993
<212> TYPE: PRT
<213> ORGANISM: Homo sapiens

<400> SEQUENCE: 77

Met Pro Ala Leu Ala Arg Asp Gly Gly Gln Leu Pro Leu Leu Val Val
1               5                   10                  15

Phe Ser Ala Met Ile Phe Gly Thr Ile Thr Asn Gln Asp Leu Pro Val
            20                  25                  30

Ile Lys Cys Val Leu Ile Asn His Lys Asn Asn Asp Ser Ser Val Gly
        35                  40                  45

Lys Ser Ser Ser Tyr Pro Met Val Ser Glu Ser Pro Glu Asp Leu Gly
    50                  55                  60

Cys Ala Leu Arg Pro Gln Ser Ser Gly Thr Val Tyr Glu Ala Ala Ala
65                  70                  75                  80

Val Glu Val Asp Val Ser Ala Ser Ile Thr Leu Gln Val Leu Val Asp
                85                  90                  95

Ala Pro Gly Asn Ile Ser Cys Leu Trp Val Phe Lys His Ser Ser Leu
            100                 105                 110

Asn Cys Gln Pro His Phe Asp Leu Gln Asn Arg Gly Val Val Ser Met
        115                 120                 125
```

```
Val Ile Leu Lys Met Thr Glu Thr Gln Ala Gly Glu Tyr Leu Leu Phe
            130                 135                 140

Ile Gln Ser Glu Ala Thr Asn Tyr Thr Ile Leu Phe Thr Val Ser Ile
145                 150                 155                 160

Arg Asn Thr Leu Leu Tyr Thr Leu Arg Arg Pro Tyr Phe Arg Lys Met
                165                 170                 175

Glu Asn Gln Asp Ala Leu Val Cys Ile Ser Glu Ser Val Pro Glu Pro
            180                 185                 190

Ile Val Glu Trp Val Leu Cys Asp Ser Gln Gly Glu Ser Cys Lys Glu
            195                 200                 205

Glu Ser Pro Ala Val Val Lys Lys Glu Glu Lys Val Leu His Glu Leu
210                 215                 220

Phe Gly Thr Asp Ile Arg Cys Cys Ala Arg Asn Glu Leu Gly Arg Glu
225                 230                 235                 240

Cys Thr Arg Leu Phe Thr Ile Asp Leu Asn Gln Thr Pro Gln Thr Thr
                245                 250                 255

Leu Pro Gln Leu Phe Leu Lys Val Gly Glu Pro Leu Trp Ile Arg Cys
            260                 265                 270

Lys Ala Val His Val Asn His Gly Phe Gly Leu Thr Trp Glu Leu Glu
            275                 280                 285

Asn Lys Ala Leu Glu Glu Gly Asn Tyr Phe Glu Met Ser Thr Tyr Ser
290                 295                 300

Thr Asn Arg Thr Met Ile Arg Ile Leu Phe Ala Phe Val Ser Ser Val
305                 310                 315                 320

Ala Arg Asn Asp Thr Gly Tyr Tyr Thr Cys Ser Ser Ser Lys His Pro
                325                 330                 335

Ser Gln Ser Ala Leu Val Thr Ile Val Glu Lys Gly Phe Ile Asn Ala
            340                 345                 350

Thr Asn Ser Ser Glu Asp Tyr Glu Ile Asp Gln Tyr Glu Glu Phe Cys
            355                 360                 365

Phe Ser Val Arg Phe Lys Ala Tyr Pro Gln Ile Arg Cys Thr Trp Thr
370                 375                 380

Phe Ser Arg Lys Ser Phe Pro Cys Glu Gln Lys Gly Leu Asp Asn Gly
385                 390                 395                 400

Tyr Ser Ile Ser Lys Phe Cys Asn His Lys His Gln Pro Gly Glu Tyr
                405                 410                 415

Ile Phe His Ala Glu Asn Asp Asp Ala Gln Phe Thr Lys Met Phe Thr
            420                 425                 430

Leu Asn Ile Arg Arg Lys Pro Gln Val Leu Ala Glu Ala Ser Ala Ser
            435                 440                 445

Gln Ala Ser Cys Phe Ser Asp Gly Tyr Pro Leu Pro Ser Trp Thr Trp
450                 455                 460

Lys Lys Cys Ser Asp Lys Ser Pro Asn Cys Thr Glu Glu Ile Thr Glu
465                 470                 475                 480

Gly Val Trp Asn Arg Lys Ala Asn Arg Lys Val Phe Gly Gln Trp Val
                485                 490                 495

Ser Ser Ser Thr Leu Asn Met Ser Glu Ala Ile Lys Gly Phe Leu Val
            500                 505                 510

Lys Cys Cys Ala Tyr Asn Ser Leu Gly Thr Ser Cys Glu Thr Ile Leu
            515                 520                 525

Leu Asn Ser Pro Gly Pro Phe Pro Phe Ile Gln Asp Asn Ile Ser Phe
530                 535                 540

Tyr Ala Thr Ile Gly Val Cys Leu Leu Phe Ile Val Val Leu Thr Leu
```

```
                545                 550                 555                 560
Leu Ile Cys His Lys Tyr Lys Lys Gln Phe Arg Tyr Glu Ser Gln Leu
                565                 570                 575

Gln Met Val Gln Val Thr Gly Ser Ser Asp Asn Glu Tyr Phe Tyr Val
                580                 585                 590

Asp Phe Arg Glu Tyr Glu Tyr Asp Leu Lys Trp Glu Phe Pro Arg Glu
                595                 600                 605

Asn Leu Glu Phe Gly Lys Val Leu Gly Ser Gly Ala Phe Gly Lys Val
            610                 615                 620

Met Asn Ala Thr Ala Tyr Gly Ile Ser Lys Thr Gly Val Ser Ile Gln
625                 630                 635                 640

Val Ala Val Lys Met Leu Lys Glu Lys Ala Asp Ser Ser Glu Arg Glu
                645                 650                 655

Ala Leu Met Ser Glu Leu Lys Met Met Thr Gln Leu Gly Ser His Glu
            660                 665                 670

Asn Ile Val Asn Leu Leu Gly Ala Cys Thr Leu Ser Gly Pro Ile Tyr
            675                 680                 685

Leu Ile Phe Glu Tyr Cys Cys Tyr Gly Asp Leu Leu Asn Tyr Leu Arg
        690                 695                 700

Ser Lys Arg Glu Lys Phe His Arg Thr Trp Thr Glu Ile Phe Lys Glu
705                 710                 715                 720

His Asn Phe Ser Phe Tyr Pro Thr Phe Gln Ser His Pro Asn Ser Ser
                725                 730                 735

Met Pro Gly Ser Arg Glu Val Gln Ile His Pro Asp Ser Asp Gln Ile
            740                 745                 750

Ser Gly Leu His Gly Asn Ser Phe His Ser Glu Asp Glu Ile Glu Tyr
        755                 760                 765

Glu Asn Gln Lys Arg Leu Glu Glu Glu Asp Leu Asn Val Leu Thr
        770                 775                 780

Phe Glu Asp Leu Leu Cys Phe Ala Tyr Gln Val Ala Lys Gly Met Glu
785                 790                 795                 800

Phe Leu Glu Phe Lys Ser Cys Val His Arg Asp Leu Ala Ala Arg Asn
                805                 810                 815

Val Leu Val Thr His Gly Lys Val Val Lys Ile Cys Asp Phe Gly Leu
            820                 825                 830

Ala Arg Asp Ile Met Ser Asp Ser Asn Tyr Val Val Arg Gly Asn Ala
        835                 840                 845

Arg Leu Pro Val Lys Trp Met Ala Pro Glu Ser Leu Phe Glu Gly Ile
        850                 855                 860

Tyr Thr Ile Lys Ser Asp Val Trp Ser Tyr Gly Ile Leu Leu Trp Glu
865                 870                 875                 880

Ile Phe Ser Leu Gly Val Asn Pro Tyr Pro Gly Ile Pro Val Asp Ala
                885                 890                 895

Asn Phe Tyr Lys Leu Ile Gln Asn Gly Phe Lys Met Asp Gln Pro Phe
            900                 905                 910

Tyr Ala Thr Glu Glu Ile Tyr Ile Ile Met Gln Ser Cys Trp Ala Phe
        915                 920                 925

Asp Ser Arg Lys Arg Pro Ser Phe Pro Asn Leu Thr Ser Phe Leu Gly
        930                 935                 940

Cys Gln Leu Ala Asp Ala Glu Glu Ala Met Tyr Gln Asn Val Asp Gly
945                 950                 955                 960

Arg Val Ser Glu Cys Pro His Thr Tyr Gln Asn Arg Arg Pro Phe Ser
                965                 970                 975
```

-continued

```
Arg Glu Met Asp Leu Gly Leu Leu Ser Pro Gln Ala Gln Val Glu Asp
            980                 985                 990
Ser

<210> SEQ ID NO 78
<211> LENGTH: 15
<212> TYPE: PRT
<213> ORGANISM: Artificial Sequence
<220> FEATURE:
<223> OTHER INFORMATION: Description of Artificial Sequence: Synthetic
      peptide

<400> SEQUENCE: 78

Gly Gly Gly Gly Ser Gly Gly Gly Gly Ser Gly Gly Gly Gly Ser
1               5                   10                  15

<210> SEQ ID NO 79
<211> LENGTH: 5
<212> TYPE: PRT
<213> ORGANISM: Artificial Sequence
<220> FEATURE:
<223> OTHER INFORMATION: Description of Artificial Sequence: Synthetic
      5xHis tag

<400> SEQUENCE: 79

His His His His His
1               5
```